(12) United States Patent
Wrazel et al.

(10) Patent No.: US 8,801,922 B2
(45) Date of Patent: Aug. 12, 2014

(54) DIALYSIS SYSTEM

(75) Inventors: Julie S. Wrazel, Corvallis, OR (US);
James R. Curtis, Portland, OR (US);
Ladislaus Nonn, Portland, OR (US);
Richard B. Peterson, Corvallis, OR (US); Hailei Wang, Corvallis, OR (US);
Robbie Ingram-Goble, Corvallis, OR (US); Luke W. Fisher, Denver, CO (US); Anna E. Garrison, Philomath, OR (US); M. Kevin Drost, Corvallis, OR (US); Goran Jovanovic, Corvallis, OR (US); Richard Todd Miller, Corvallis, OR (US); Bruce W. Johnson, Corvallis, OR (US); Alana Warner-Tuhy, Corvallis, OR (US); Eric K. Anderson, Corvallis, OR (US)

(73) Assignees: State of Oregon acting by and through the State Board of Higher Education on behalf of Oregon State University, Corvallis, OR (US); Home Dialysis Plus, ltd., Portland, OR (US)

( * ) Notice: Subject to any disclaimer, the term of this patent is extended or adjusted under 35 U.S.C. 154(b) by 1065 days.

(21) Appl. No.: 12/795,444

(22) Filed: Jun. 7, 2010

(65) Prior Publication Data

US 2010/0326916 A1    Dec. 30, 2010

Related U.S. Application Data

(60) Provisional application No. 61/220,117, filed on Jun. 24, 2009, provisional application No. 61/267,043, filed on Dec. 5, 2009.

(51) Int. Cl.
| | | |
|---|---|---|
| B01D 61/32 | (2006.01) |
| B01D 61/28 | (2006.01) |
| B01D 61/30 | (2006.01) |
| A61M 1/16 | (2006.01) |
| A61M 1/14 | (2006.01) |
| C02F 1/02 | (2006.01) |
| C02F 1/44 | (2006.01) |
| C02F 103/02 | (2006.01) |
| F28D 21/00 | (2006.01) |

(52) U.S. Cl.
CPC . *A61M 1/16* (2013.01); *A61M 1/14* (2013.01); *A61M 1/1656* (2013.01); *F28F 2260/02* (2013.01); *C02F 1/02* (2013.01); *C02F 1/44* (2013.01); *C02F 2303/04* (2013.01); *C02F 2103/026* (2013.01); *F28D 2021/005* (2013.01)
USPC ........... 210/137; 210/181; 210/177; 210/205; 210/321.6

(58) Field of Classification Search
None
See application file for complete search history.

(56) References Cited

U.S. PATENT DOCUMENTS

| | | |
|---|---|---|
| 3,356,360 A | 12/1967 | Ward |
| 3,762,032 A | 10/1973 | Bowling et al. |

(Continued)

FOREIGN PATENT DOCUMENTS

| | | |
|---|---|---|
| EP | 0 324 922 | 7/1989 |
| GB | 1 289 738 | 9/1972 |

(Continued)

OTHER PUBLICATIONS

Allis and Spencer, "16: Nanostructural Architectures from Molecular Building Blocks," *Handbook of Nanoscience, Engineering, and Technology*, pp. 16-1 to 16-32, 2003.

(Continued)

*Primary Examiner* — Terry Cecil
(74) *Attorney, Agent, or Firm* — Klarquist Sparkman, LLP

(57) ABSTRACT

A dialysis system includes a filtration system capable of filtering a water stream, a water purification system capable of purifying said water stream in a non-batch process, a mixing system capable of producing a stream of dialysate from mixing one or more dialysate components with the water stream in a non-batch process, and a dialyzer system. The dialyzer may be a microfluidic dialyzer capable of being fluidly coupled to the stream of dialysate and a blood stream.

17 Claims, 36 Drawing Sheets

(56) References Cited

U.S. PATENT DOCUMENTS

| | | | |
|---|---|---|---|
| 3,809,309 A | 5/1974 | Batista |
| 3,965,008 A | 6/1976 | Dawson |
| 4,080,295 A | 3/1978 | Riede |
| 4,089,456 A | 5/1978 | Toppen et al. |
| 4,100,068 A | 7/1978 | Jordan et al. |
| 4,115,273 A | 9/1978 | Winstead |
| 4,155,157 A | 5/1979 | Gersbacher |
| 4,204,628 A | 5/1980 | Houston et al. |
| 4,310,416 A | 1/1982 | Tanaka et al. |
| 4,647,748 A | 3/1987 | Glassman |
| 4,689,108 A | 8/1987 | Barry, Jr. et al. |
| 4,869,421 A | 9/1989 | Norris et al. |
| 4,875,619 A | 10/1989 | Anderson et al. |
| 5,087,930 A | 2/1992 | Roy et al. |
| 5,094,749 A | 3/1992 | Seita et al. |
| 5,147,605 A | 9/1992 | Tatsuno et al. |
| 5,232,145 A | 8/1993 | Alley et al. |
| 5,313,023 A | 5/1994 | Johnson |
| 5,316,676 A | 5/1994 | Drori |
| 5,385,623 A | 1/1995 | Diaz |
| 5,469,264 A | 11/1995 | Shigemori |
| 5,534,328 A | 7/1996 | Ashmead et al. |
| 5,571,754 A | 11/1996 | Bertin et al. |
| 5,580,523 A | 12/1996 | Bard |
| 5,595,712 A | 1/1997 | Harbster et al. |
| 5,610,645 A | 3/1997 | Moore et al. |
| 5,611,214 A | 3/1997 | Wegeng et al. |
| 5,648,684 A | 7/1997 | Bertin et al. |
| 5,689,966 A | 11/1997 | Zess et al. |
| 5,749,226 A | 5/1998 | Bowman et al. |
| 5,769,985 A | 6/1998 | Kawakami et al. |
| 5,779,833 A | 7/1998 | Cawley et al. |
| 5,811,062 A | 9/1998 | Wegeng et al. |
| 5,868,930 A | 2/1999 | Kopf |
| 5,885,456 A | 3/1999 | Charkoudian et al. |
| 5,921,678 A | 7/1999 | Desai et al. |
| 5,932,940 A | 8/1999 | Epstein et al. |
| 5,974,867 A | 11/1999 | Forster et al. |
| 5,985,068 A | 11/1999 | Kawakami et al. |
| 6,024,276 A | 2/2000 | Hirata et al. |
| 6,048,432 A | 4/2000 | Ecer |
| 6,082,891 A | 7/2000 | Schubert et al. |
| 6,100,463 A | 8/2000 | Ladd et al. |
| 6,109,994 A | 8/2000 | Cho et al. |
| 6,121,539 A | 9/2000 | Johnson et al. |
| 6,123,798 A | 9/2000 | Gandhi et al. |
| 6,126,723 A | 10/2000 | Drost et al. |
| 6,129,973 A | 10/2000 | Martin et al. |
| 6,143,247 A | 11/2000 | Sheppard et al. |
| 6,148,635 A | 11/2000 | Beebe et al. |
| 6,167,910 B1 | 1/2001 | Chow |
| 6,192,596 B1 | 2/2001 | Bennett et al. |
| 6,202,312 B1 | 3/2001 | Rando |
| 6,212,333 B1 | 4/2001 | Olk et al. |
| 6,225,497 B1 | 5/2001 | Becker et al. |
| 6,329,139 B1 | 12/2001 | Nova et al. |
| 6,334,301 B1 | 1/2002 | Otsap et al. |
| 6,357,332 B1 | 3/2002 | Vecchio |
| 6,375,871 B1 | 4/2002 | Bentsen et al. |
| 6,477,058 B1 | 11/2002 | Luebs et al. |
| 6,488,842 B2 | 12/2002 | Nagaoka |
| 6,514,412 B1 | 2/2003 | Insley et al. |
| 6,537,506 B1 | 3/2003 | Schwalbe et al. |
| 6,607,644 B1 | 8/2003 | Apffel, Jr. |
| 6,616,877 B2 | 9/2003 | Close et al. |
| 6,616,909 B1 | 9/2003 | Tonkovich et al. |
| 6,623,860 B2 | 9/2003 | Hu et al. |
| 6,635,226 B1 | 10/2003 | Tso et al. |
| 6,652,627 B1 | 11/2003 | Tonkovich et al. |
| 6,656,315 B2 | 12/2003 | Sallavanti et al. |
| 6,666,909 B1 | 12/2003 | TeGrotenhuis et al. |
| 6,672,502 B1 | 1/2004 | Paul et al. |
| 6,676,835 B2 | 1/2004 | O'Connor et al. |
| 6,688,381 B2 | 2/2004 | Pence et al. |
| 6,737,026 B1 | 5/2004 | Bergh et al. |
| 6,744,038 B2 | 6/2004 | Wang et al. |
| 6,749,814 B1 | 6/2004 | Bergh et al. |
| 6,793,831 B1 | 9/2004 | Paul et al. |
| 6,838,156 B1 | 1/2005 | Neyer et al. |
| 6,852,231 B2 | 2/2005 | Ivansons et al. |
| 6,892,781 B2 | 5/2005 | McHerron et al. |
| 6,903,332 B2 | 6/2005 | Weiss et al. |
| 6,911,262 B2 | 6/2005 | Sallavanti et al. |
| 6,913,877 B1 | 7/2005 | Chaplen et al. |
| 6,986,428 B2 | 1/2006 | Hester et al. |
| 6,989,134 B2 | 1/2006 | Tonkovich et al. |
| 7,118,920 B2 | 10/2006 | Brophy et al. |
| 7,150,815 B2 | 12/2006 | Ashmead et al. |
| 7,264,723 B2 | 9/2007 | Singh et al. |
| 7,279,134 B2 | 10/2007 | Chan et al. |
| 7,378,280 B2 | 5/2008 | Quake et al. |
| 7,507,380 B2 | 3/2009 | Chang et al. |
| 2002/0045265 A1 | 4/2002 | Bergh et al. |
| 2002/0108859 A1 | 8/2002 | Wang et al. |
| 2003/0039169 A1 | 2/2003 | Ehrfeld et al. |
| 2003/0052429 A1 | 3/2003 | Vigna et al. |
| 2003/0082066 A1 | 5/2003 | Hajaligol et al. |
| 2003/0156991 A1 | 8/2003 | Halas et al. |
| 2003/0168590 A1 | 9/2003 | Weiss et al. |
| 2003/0183345 A1 | 10/2003 | Soberay |
| 2003/0221777 A1 | 12/2003 | McHerron et al. |
| 2004/0012122 A1 | 1/2004 | Nagaoka et al. |
| 2004/0022691 A1 | 2/2004 | Allen et al. |
| 2004/0035452 A1 | 2/2004 | Ma |
| 2004/0072278 A1 | 4/2004 | Chou et al. |
| 2004/0086427 A1 | 5/2004 | Childers et al. |
| 2004/0125689 A1 | 7/2004 | Ehrfeld et al. |
| 2004/0208751 A1 | 10/2004 | Lazar et al. |
| 2004/0256230 A1 | 12/2004 | Yager et al. |
| 2005/0007748 A1 | 1/2005 | Callahan et al. |
| 2005/0074834 A1 | 4/2005 | Chaplen et al. |
| 2005/0126211 A1 | 6/2005 | Drost et al. |
| 2005/0129580 A1 | 6/2005 | Swinehart et al. |
| 2005/0202557 A1 | 9/2005 | Borenstein et al. |
| 2005/0220681 A1 | 10/2005 | Chang et al. |
| 2006/0266692 A1 | 11/2006 | Foster et al. |
| 2007/0119771 A1 | 5/2007 | Schukar et al. |
| 2008/0009780 A1 | 1/2008 | Leonard et al. |
| 2009/0095679 A1* | 4/2009 | Demers et al. ............ 210/646 |
| 2009/0114595 A1* | 5/2009 | Wallenas et al. ......... 210/646 |
| 2009/0211977 A1 | 8/2009 | Miller |

FOREIGN PATENT DOCUMENTS

| | | |
|---|---|---|
| WO | WO 02/40874 | 5/2002 |
| WO | WO 02/076529 | 10/2002 |
| WO | WO 2005/045894 | 5/2005 |
| WO | WO 2006/042079 | 4/2006 |

OTHER PUBLICATIONS

Alm, "Diffusion Bonding—Methods and Applications: Part I—Terminology," Systems Group of TRW Inc., *Adhesives Age*, pp. 28-32, Jul. 1970.

Alman et al., "Processing, Structure and Properties of Aluminum-Aluminide Layered Sheet Composites," *Light Weight Alloys for Aerospace Applications III, The Minerals, Metals & Materials Society*, pp. 531-544, 1995.

Alman et al., "Intermetallic Sheets Synthesized from Elemental Ti, Al and Nb Foils," *Metallurgical and Materials Transactions*, 26A:2759-2762, Oct. 1995.

Alman et al., "Fabrication, Structure and Properties of Aluminum-Aluminide Layered Composites," *Materials Research Society Symp. Proc.*, 434:255-260, 1996.

Alman et al., "Fabrication of NiAl Intermetallic Reactors for Microtechnology-Based Energy Chemical Systems (MECS)," *Transactions of NAMRI/SME*, XXIX:453-459, 2001.

Anglés et al., "Plasticized Starch/Tunicin Whiskers Nanocomposite Materials. 2. Mechanical Behavior," *Macromolecules*, 34:2921-2931, 2001.

Battezzati et al., "Solid State Reaction in Al/Ni Alternate Foils Induced by Cold Rolling and Annealing," *Acta Mater.*, 47:1901-1914, 1999.

(56) References Cited

OTHER PUBLICATIONS

Battista, "Chapter Two: Microcrystalline Celluloses," *Microcrystal Polymer Science*, pp. 17-57, McGraw-Hill, New York, New York, 1975.

Benson et al., "Process Miniaturization—A Route to Total Environmental Acceptability?," *Trans. IchemE*, 7(Part A):160-168, 1993.

Bower et al., "Aligned Wafer Bonding: A Key to Three Dimensional Microstructures," *Journal of Electronic Materials*, 20:383-387, 1991.

Chazeau et al., "Mechanical behavior above T-g of plasticized PVC reinforced with cellulose whiskers; a SANS structural study," *Polymer*, 40(19):5333-5344, 1999.

Colgan, "A Review of Thin-Film Aluminide Formation," *Material Science Reports* 5:1-44, Jan. 1990.

Cuta et al., "Fabrication and testing of microchannel heat exchangers," *SPIE Conf.*, 2640:152-160, 1995.

D'Heurle, "Reactive Diffusion in a Prototype System: Nickel-Aluminum I: Non-Constant Diffusion Coefficient," *Thin Solid Films*, 215:19-25, 1992.

De Souza-Lima et al., "Rodlike Cellulose Microcrystals: Structure, Properties, and Applications," *Macromolecular Rapid Communications*, 25:771-787, 2004.

Deevi et al., "Processing, Properties, and Applications of Nickel and Iron Aluminides," *Progress in Materials Science*, 42:177-192, 1997.

Demura et al., "Ductile Thin Foil of $Ni_3Al$," *Mechanical Properties of Structural Films*, Nos. 11-12, 2000.

Demura et al., "Fabrication of $Ni_3Al$ Thin Foil by Cold-Rolling," *Intermetallics*, 9:157-167, 2001.

Derby et al., "Theoretical Model for Diffusion Bonding," *Metal Science*, 16:49-56, Jan. 1982.

Dunford et al., "Diffusion Bonding of Al-Li Alloys," *Materials Science and Technology*, 8:385-398, May 1992.

Duszczyk et al., "The Characteristics of the Diffusion Between the As-Reaction-Formed $Ni_3Al$ Intermetallic Compound and Pure Nickel for Interfacial Bonding," *Journal of Materials Science Letters*, 18:111-113, 1999.

Ehrfeld et al., "Characterization of mixing in micromixers by a test reaction: Single mixing units and mixer arrays," *Ind. Eng. Chem. Res.*, 38(3):1075, 1999.

Esposito, *Fluid Power with Applications*, 2d ed., Prentice Hall, Englewood Cliff, New Jersey, pp. 380-381, 1988.

Favier et al., "Nanocomposite Materials from Latex and Cellulose Whiskers," *Polymers for Advanced Technologies* 6:351-355, 1995.

Favier et al., "Mechanical Percolation in Cellulose Whisker Nanocomposites," *Polymer Engineering and Science*, 37:1732-1739, 1997.

Fischer et al., "Manufacturing of Aluminum Nitride Heat Exchangers by Ceramic Injection Molding," *Ceramic Engineering and Science Proceedings*, 20(4):595-602, 1999.

Garmong et al., "Attainment of Full Interfacial Contact During Diffusion Bonding," *Metallurgical Transactions*, 6A:1269-1279, Jun. 1975.

George et al., "Ordered Intermetallics," *Annu. Rev. Mater. Sci.*, 24:409-451, 1994.

Glatz et al., "Diffusion Bonding of Intermetallic Ti-47Al-2Cr-0-2Si Sheet Material and Mechanical Properties of Joints at Room Temperature and Elevated Temperatures," *Intermetallics*, 5:415-423, Sep. 1997.

Goldberg, "Narrow Channel Forced Air Heat Sink," *IEEE Transactions on Components, Hybrids, and Manufacturing Technology*, CHMT-7(1):154-159, Mar. 1984.

Grunert et al., "Progress in the Development of Cellulose Reinforced Nanocomposites," *Polymeric Materials: Science and Engineering*, Abstract of Papers, Abstract No. 126, 2000.

Grunert et al., "Cellulose Nanocrystal Reinforced Cellulose Acetate Butyrate Nanocomposites," *Polymeric Materials: Science and Engineering*, 86:367-368, 2002.

Haas et al., "Fabrication and Performance of MMW and SMMW Platelet Horn Arrays," *Intl. J. Infrared and Millimeter Waves*, 14(11):2289-2293, 1993.

Haas, "Further development of MMW and SMMW platelet feed horn arrays," *Astron. Soc. Pac. Conf. Ser.*, 75:99-105, 1995.

Herschberg, "Manufacturing Technology of the Tektronix Digital Ink Jet Head," *SPSE $3^{rd}$ International Congress on Advances in Non-Impact Printing Technologies, Journal of Imaging Technology*, 14:124-128, 1998.

Hessel et al., "High Temperature HCN Generation in an Integrated Microreaction System," *Proc. IMRET3*, Frankfurt, Germany, pp. 151-164, Apr. 1999.

Hill et al., "Modelling Solid-State Diffusion Bonding," *Acta Metal. Mater.*, 37(9):2425-2537, 1989.

Humpston et al., "Principles in Soldering and Brazing, 4.4.2. Diffusion Soldering and Brazing," *ASM International*, pp. 128-143, 1993.

Islam et al., "Effect of Surface Finish and Sheet Thickness on Isostatic Diffusion Bonding of Superplastic T1-6A1-4V," *Materials Science and Technology*, 13:1045-1050, Dec. 1997.

Islam et al., "Isostatic Diffusion Bonding of a Microduplex Stainless Steel," *Scripta Materialia*, 38(8):1187-1193, 1998.

Jacobson et al., "Diffusion Soldering," *Soldering & Surface Mount Technology*, 10:27-32, 1992.

Kao et al., "A Theoretical Analysis for the Formation of Periodic Layered Structure in Ternary Diffusion Couples Involving a Displacement Type of Reaction," *Acta. Metal. Mater.*, 41(12):3463-3472, 1993.

Khan et al., "Transient liquid phase diffusion bonding and associated recrystalization phenomenon when joining ODS ferritic superalloys," *J Mat. Sci.*, 31:2937-2943, Jun. 1996.

Kleiner, "High Performance Forced Air Cooling Scheme Employing Microchannel Heat Exchangers," *IEEE Transactions on Components, Hybrids, and Manufacturing Technology*, 18(4):795-804, Dec. 1995.

Knight, "Optimal Thermal Design of Air Cooled Forced Convection Finned Heat Sinks-Environmental Verification," *IEEE Transactions on Components, Hybrids, and Manufacturing Technology*, 15:754-760, 1992.

Koeneman et al., "Feasibility of Micro Power Supplies for MEMS," *Journal of MicroElectoMechanical Systems*, 6(4):355-362, 1997.

Krause et al., "Microchannel coolers for high power laser diodes in copper technology," *Proc. SPIE*, 2148:351-385, 1994.

Ling et al., "Passive Alignment and its Application in Multi-level X-ray Lithography," *Materials and Device Characterization in Micromachining III, Proceedings of SPIE*, 4175:43-19, 2000.

Little, "Microminiature Refrigerators for Joule-Thomson Cooling of Electronic Chips and Devices," *Advances in Cryogenic Engineering*, 35:1325-1333, 1990.

Liu et al., "Ordered Intermetallic Alloys, Part I: Nickle and Iron Aluminites," *Journal of Minerals, Metals, and Materials Society*, 45(5):38-44, May 1993.

Lopez et al., "Microstructural analysis of steel-nickel alloy clad interfaces," *Mat. Sci. and Tech.*, pp. 45-55, Jan. 1996.

Martin et al.., "Microchannel heat exchangers for advanced climate control," *Proc. SPIE* 2639:82-88, 1995.

Martin et al., "Micorfabrication methods for microchannel reactors and separations systems," *Pacific Northwest National Laboratory*, 8 pages, 1997.

Martin et al., "Microfabrication Methods for Microchannel Reactors and Separations Systems," *Chem. Eng. Comm.*, 173:245-254, 1999.

Matson et al., "Laser micromachined microchannel solvent separator," *SPIE* 3223:253-259, 1997.

Matson et al., "Fabrication of Microchannel Chemical Reactors Using a Metal Lamination Process," *Proc. IMRET3*, 10 pages, Frankfurt, Germany, Apr. 1999.

Michaelson et al., "The Early Stages of Solid-State Reactions in Ni/Al Multilayer Films," *J. Appl. Phys.*, 80(12):6689-6698, Dec. 1996.

Moore et al., "Diffusion Brazing NiAl with Self-Generated Filler Metal," *Materials Research Society, Mat. Res. Soc. Symp. Proc.*, 288:1173-1178, 1993.

Morin et al., "Nanocomposites of Chitin Whiskers from *Riftia* Tubes and Poly(caprolactone)," *Macromolecules*, 35:2190-2199, 2002.

(56) References Cited

OTHER PUBLICATIONS

Nakamura et al., "Research on Pressure Welding Conditions of Various Work Metals (Effects of Contact Pressure, Surface Expansion Ratio and Temperature)," *JSME International Journal*, Series III 31(3):612-617, 1988.

Nakao et al., "Diffusion Bonding of Intermetallic Compound TiAl," *ISIJ International*, 31(10):1260-1266, 1991.

NASA, "National Space Transportation System Shuttle Reference Manual," p. 8, located at www.ksc.nasa.gov/shuttle/technology/sts-newsref/sts-oms.html, 1988.

Oddy et al., "Electrokinetic Instability Micromixing," *Anal. Chem.*, 73:5822-5832, 2001.

Orhan et al., "A New Model for Diffusion Bonding and its Application to Duplex Alloys," *Materials Science and Engineering*, A271:458-468, 1999.

Orts et al., "Effect of Fiber Source on Cellulose Reinforced Polyme Nanocomposites," $62_{nd}$ *Annual Technical Conference—Society of Plastics and Engineering*, 2 pages, 2004.

Paillet et al., "Chitin Whisker Reinforced Thermoplastic Nanocomposites," *Macromolecules*, 34(19):6527-6530, 2001.

Paransky et al., "Kinetics of Two-Phase Layer Growth During Reactive Diffusion," *Materials Science and Engineering*, A270:231-236, 1999.

Paul et al., "Microlamination for Microtechnology-based Energy, Chemical, and Biological Systems," *ASME IMECE*, 39:45-52, Nashville, Tennessee, Nov. 15-20, 1999.

Paul et al., "Intermetallic Microlamination for High-Temperature Microreactors," *4th Int. Conf Microreaction Tech.*, Atlanta, Georgia, pp. 236-243, American Institute of Chemical Engineers [AIChE], Mar. 5-9, 2000.

Paul et al., "Limits on Aspect Ratio in Two-fluid Micro-scale Heat Exchangers," *Transactions of NAMRI XXIX*, Gainesville, Florida, 2001.

Paule et al., "An Evaluation of Two Methods for Producing Intermetallic Microchannels," *Proceedings of IMEC 2002, ASME International Mechanical Engineering Congress & Exhibition*, pp. 261-266, Nov. 17-22, 2002, New Orleans, Louisiana.

Paul et al., "Understanding Limits on Fin Aspect Ratios in Counterflow Microchannel Arrays Produced by Diffusion Bonding," *J. Manuf Sci. Eng.*, 128(4):977, Nov. 2006.

Peterson, "Size Limits for Regenerative Heat Engines," *Microscale Thermophysical Engineering*, 2:121-131, 1998.

Peterson et al., "Numerical Modeling of Conduction Effects in Microscale Counterflow Heat Exchangers," *Microscale Thermophysical Engineering*, 3:17-30, 1999.

Philibert, "Reactive Diffusion in Thin Films," *Applied Surface Sciences*, 53:74-81, 1991.

Pilling, "The Kinetics of Isostatic Diffusion Bonding in Superplastic Materials," *Materials Science and Engineering*, 100:137-144, 1988.

Pilling, "On the Modeling of Diffusion Bonding in Materials: Superplastic Super Alpha-2," *Materials Science and Engineering*, A205:72-78, 1996.

Pluess, "Application of Controlled Thermal Expansion in Diffusion Bonding for the High-Volume Microlamination of MECS Devices," Thesis (MS)—Oregon State University, 2004.

Pluess and Paul, "Application of Controlled Thermal Expansion in Microlamination for the Economical Production of Bulk Microchannel Systems," *Chem Engr Comm*, 194:1259-1270, 2007.

PowerPoint slides presented at $4^{th}$ International Conference of Microreaction Technology, Atlanta, Georgia, Mar. 5-9, 2000.

Raviprasad et al.., "Layered Structures Produced by Rolling Dissimilar Metals," *Journal of Materials Science Letters*, 15:511-514, 1996.

Revol et al., "Cellulose-based Chiral Nematic Structures," *Cellulosics: Chemical, Biochemical and Material Aspects*, pp. 115-122, eds. J. F. Kennedy, G. O. Phillips and P. A. Williams, Ellis Horwood, New York, New York, 1993.

Ridley et al.., "Isostatic diffusion bonding of microduplex stainless steel," *Mat. Sci. and Tech.*, 8:791-795, Sep. 1992.

Robertson et al., "In Situ Interferometric Alignment Systems for the Assembly of Microchannel Relay Systems," *Applied Optics*, 36:9253-9260, 1997.

Rode et al., "Self-Aligned Positioning of Microoptical Components by Precision Prismatic Grooves Impressed in Metal," *IEEE Journal of Microelectromechanical Systems*, 8:58-64, Mar. 1999.

Ruiz et al., "Processing and characterization of new thermoset nanocomposites based on cellulose whiskers," *Composite Interfaces*, 7(2):117-131, 2000.

Schwab et al., "Molecular Rods. 1. Simple Axial Rods," *Chemical Reviews*, 99(7):1863-1933, 1999.

Sharma et al., "The Application of Surface Mount Technology to Multi-Scale Process Intensification," *ASPE*, pp. 1-4, Oct. 2003.

Spadaccini et al.., "Development of a Catalytic Silicon Micro-Combustor for Hydrocarbon-Fueled Power Mems," *The Fifteenth IEEE International Conference on Micro Electro Mechanical Systems*, pp. 228-231, Las Vegas, Nevada, Jan. 20-24, 2002.

Stroock et al., "Chaotic Mixer for Microchannels," *Science*, 295:647-651, 2002.

Strum et al.., "Liquid-Assisted Diffusion Bonding of NiAl," *Advanced Joining Technologies for New Materials II*, Conference Proceedings, pp. 76-88, Mar. 1994.

"Technology Development Through Industrial Partnerships," *Federal Energy Technology Center*, Oct. 1997.

Tour, "Chapter 3: Chemical Synthesis," *Molecular Electronics, Commercial Insights, Chemistry, Devices, Architecture and Programming*, World Science, pp. 33-41, Mar. 2003.

Uenishi et al.., "Joining of Intermetallic Compound TiAl by Using Al Filler Metal," *Zeitschrift fur Metallkunde*, 86(4):270-274, 1995.

Van Loo et al., "Solid State Diffusion and Reactive Phase Formation," *Solid State Ionics*, 95:95-106, 1997.

Wang et al., "Ni-$Al_2O_3$ and Ni-Al Composite High-Aspect-Ratio Microstructures," *Materials and Device Characterization in Micromachining*, 3512:344-352, 1998.

Wattanutchariaya et al., "Bonding Fixture Tolerances for High-Volume Metal Microlamination Based on Fin Buckling and Lamina Misalignment Behavior," *J. Intl Soc of Precision Engr and Nanotechnology*, 2002.

Wegeng et al., "Chemical system miniaturization," *Proceedings of the AIChE Spring National Meeting*, pp. 1-13, Feb. 1996.

Wegeng et al., "Energy systems miniaturization technologies, devices, and systems," *Proceedings of the International Symposium on Advanced Energy Conversion Systems and Related Technologies (RAN95)*, 8 pages, Dec. 1995.

Welding Institute, http://www.twi.co.uk/j32k/protected/band_3/ksab001.html, accessed on Feb. 22, 2008.

Wu et al., "Superplastic Forming/Diffusion Bonding of Laser Surface Melted TiAl Intermetallic Alloy," *Scripta Materialia*, 45:895-899, 2001.

Yussuf et al., "Microwave Welding of Polymeric-Microfluidic Devices," *Micromec. Microeng.*, 15:1692-1699, 2005.

U.S. Appl. No. 09/369,679—Office Action dated Jun. 22, 2001.
U.S. Appl. No. 09/369,679—Office Action dated Apr. 11, 2002.
U.S. Appl. No. 09/369,679—Office Action dated Dec. 6, 2002.
U.S. Appl. No. 09/996,621—Office Action dated May 16, 2003.
U.S. Appl. No. 10/576,963—Office Action dated Jul. 28, 2009.
U.S. Appl. No. 10/576,963—Office Action dated Jan. 25, 2010.
U.S. Appl. No. 10/803,502—Office Action dated Jun. 6, 2008.
U.S. Appl. No. 10/803,502—Office Action dated Mar. 30, 2009.
U.S. Appl. No. 10/803,502—Office Action dated Oct. 21, 2009.
U.S. Appl. No. 11/086,074—Office Action dated Apr. 1, 2008.
U.S. Appl. No. 11/243,937—Office Action dated Apr. 15, 2009.
U.S. Appl. No. 11/243,937—Office Action dated Sep. 20, 2010.
U.S. Appl. No. 11/517,731—Office Action dated Aug. 29, 2008.

Porter et al., "Cost Drivers in Microlamination Based on a High-Volume Production System Design," *Proceedings of IMECE 2002, ASME International Mechanical Engineering Congress & Exposition*, Nov. 17-22, 2002, New Orleans, Louisiana.

International Search Report dated Sep. 16, 2010, in International Patent Application No. PCT/US2010/037621.

\* cited by examiner

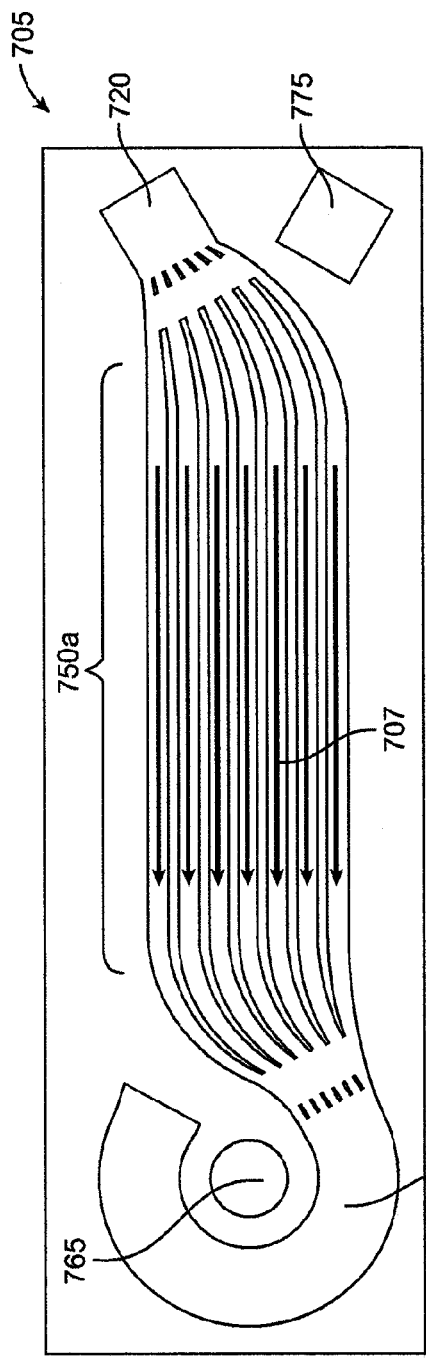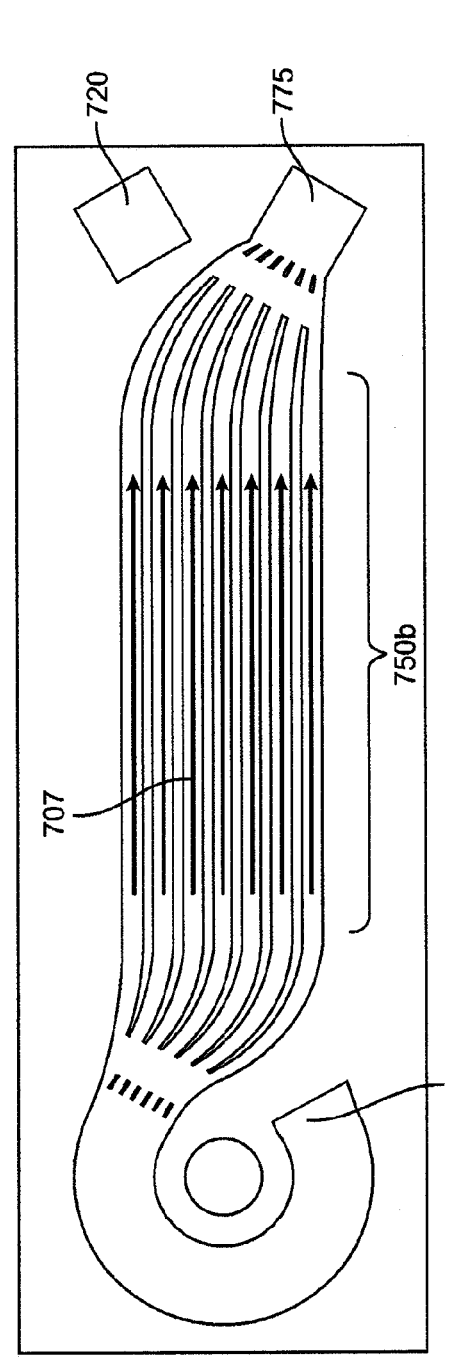
FIG. 8A
FIG. 8B

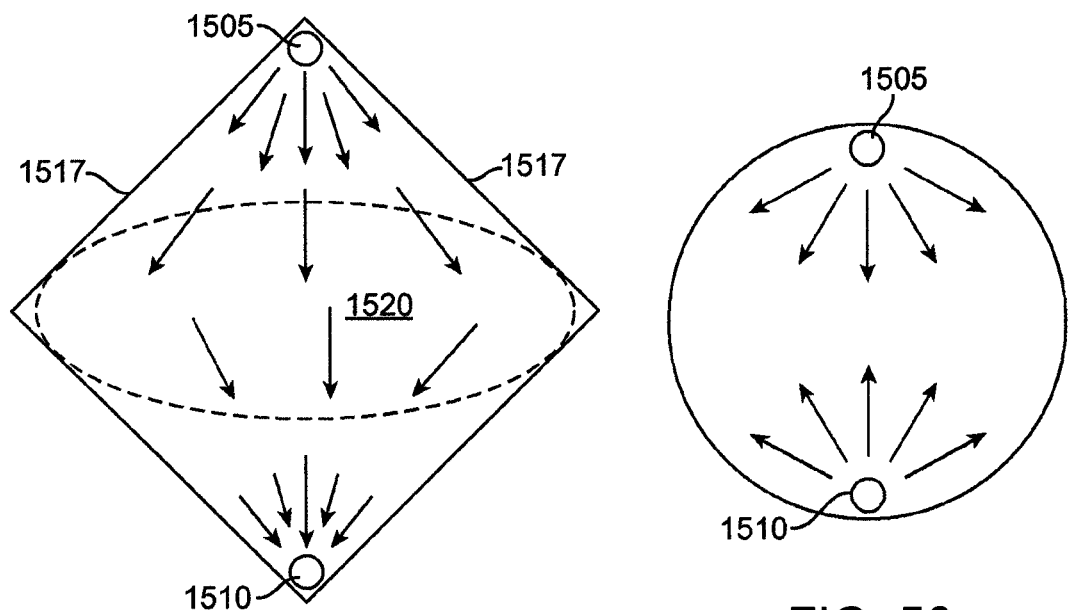
FIG. 55
FIG. 56
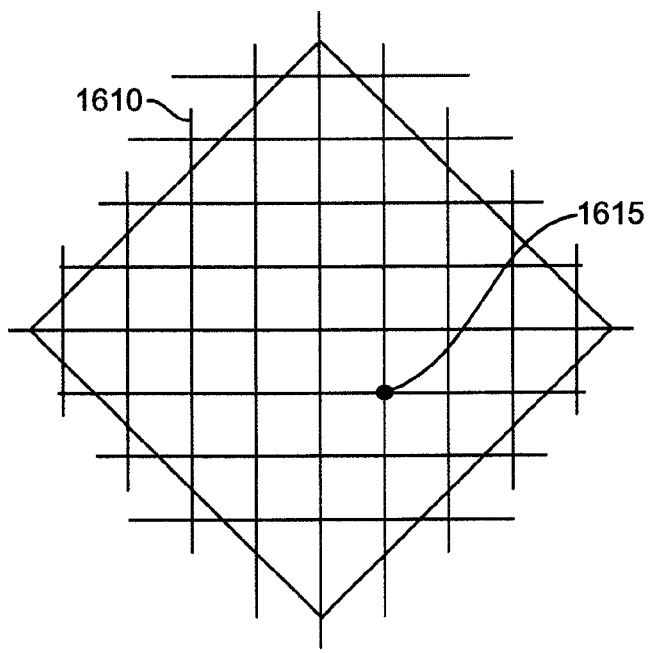
FIG. 57

DIALYSIS SYSTEM

RELATED APPLICATIONS

This application is related to the following U.S. Patent Applications: (1) U.S. patent application entitled "Microfluidic Devices," filed on Jun. 7, 2010, and naming M. Kevin Drost, Goran Jovanovic, Todd Miller, James R. Curtis, Bruce Johnson, Alana Warner-Tuhy, Eric Anderson and Julie Wrazel, which claims priority to U.S. Provisional Patent Application Ser. No. 61/220,117, filed on Jun. 24, 2009; (2) U.S. patent application entitled "Dialysis System With Ultrafiltration Control," filed on Jun. 7, 2010, and naming James R. Curtis, Ladislaus F. Norm and Julie Wrazel, which claims priority to U.S. Provisional Patent Application Ser. No. 61/267,043, filed on Dec. 5, 2009; and (3) U.S. patent application entitled "Fluid Purification System," filed on Jun. 7, 2010, and naming Richard B. Peterson, James R. Curtis, Hailei Wang, Robbie Ingram-Gobel, Luke W. Fisher and Anna E. Garrison. The disclosures of the aforementioned patent applications are incorporated herein by reference in their entirety.

FIELD

The present disclosure concerns a dialysis system, such as a microfluidic or flow field dialyzer capable of being fluidly coupled to a dialysate stream and a blood stream, and a method for using the dialysis system.

BACKGROUND

There are, at present, hundreds of thousands of patients in the United States with end-stage renal disease. Most of those require dialysis to survive. United States Renal Data System projects the number of patients in the U.S. on dialysis will climb past 600,000 by 2012. Many patients receive dialysis treatment at a dialysis center, which can place a demanding, restrictive and tiring schedule on a patient. Patients who receive in-center dialysis typically must travel to the center at least three times a week and sit in a chair for 3 to 4 hours each time while toxins and excess fluids are filtered from their blood. After the treatment, the patient must wait for the needle site to stop bleeding and blood pressure to return to normal, which requires even more time taken away from other, more fulfilling activities in their daily lives. Moreover, in-center patients must follow an uncompromising schedule as a typical center treats three to five shifts of patients in the course of a day. As a result, many people who dialyze three times a week complain of feeling exhausted for at least a few hours after a session.

Given the demanding nature of in-center dialysis, many patients have turned to home dialysis as an option. Home dialysis provides the patient with scheduling flexibility as it permits the patient to choose treatment times to fit other activities, such as going to work or caring for a family member. Unfortunately, current dialysis systems are generally unsuitable for use in a patient's home. One reason for this is that current systems are too large and bulky to fit within a typical home. Current dialysis systems are also energy-inefficient in that they use large amounts of energy and require enormous amounts of water for proper use. Although some home dialysis systems are available, they generally use complex flow-balancing technology that is relatively expensive to manufacture and most systems are designed with a system of solenoid valves that create high noise levels. As a result, most dialysis treatments are performed at dialysis centers.

SUMMARY

In view of the foregoing, there is a need for improved dialysis systems that are suited for use in a home, either for daily use or nocturnal use. Disclosed is a dialysis system that is smaller, more portable, consumes less water, utilizes much lower flow rates of dialysate and blood than are presently used in current dialysis systems, and enables better control over levels of ultrafiltration and diafiltration than do current systems. The system is compact and light-weight relative to existing systems and consumes relatively low amounts of energy. The system can be connected to a residential source of water (such as a running water tap to provide a continuous or semi-continuous household stream of water) and can produce real-time pasteurized water for use in home dialysis, without the need to heat and cool large, batched quantities of water.

In one aspect, there is disclosed a medical system, comprising: a filtration system capable of filtering a water stream; a water purification system capable of purifying said water stream in a non-batch process; a mixing system capable of producing a stream of dialysate from mixing one or more dialysate components with the water stream in a non-batch process; and a dialyzer system, comprising: a microfluidic dialyzer capable of being fluidly coupled to the stream of dialysate and a blood stream, the dialyzer having a membrane separating the stream of dialysate from the blood stream, the membrane facilitating dialysis of the blood stream; a plurality of pumps capable of pumping the stream of dialysate across the dialyzer; and a controller operatively coupled to the plurality of pumps, the controller capable of controlling a flow rate of the dialysate stream through one or more of the plurality of pumps so as to perform one or both of the processes of ultrafiltration and hemodiafiltration on the blood stream while the blood stream is undergoing dialysis.

In another aspect, there is disclosed a dialysis system, comprising: a water purification system adapted to process a water source, such as a household water stream, in a non-batch process to produce an ultra-high-temperature-pasteurized water stream; a dialysate preparation system adapted to mix the ultra-high-temperature-pasteurized water stream with dialysate components to produce dialysate; and a dialyzer having a blood flow pathway through which blood flows and a dialysate flow pathway through which the dialysate flows, the dialyzer adapted to perform dialysis on the blood.

Other features and advantages should be apparent from the following description of various embodiments, which illustrate, by way of example, the principles of the disclosed devices and methods.

BRIEF DESCRIPTION OF THE DRAWINGS

FIG. 8A shows a plan view of another embodiment of an inlet lamina.

FIG. 8B shows a plan view another embodiment of an outlet lamina.

FIG. 55 is a plan view of an embodiment of a lamina of a flow field dialyzer without header regions.

FIG. 56 is a plan view of another embodiment of a lamina of a flow field dialyzer without header regions.

FIG. 57 is a plan, schematic view of a pathway of lasers for forming a flow field.

DETAILED DESCRIPTION

In order to promote an understanding of the principals of the disclosure, reference is made to the drawings and the embodiments illustrated therein. Nevertheless, it will be understood that the drawings are illustrative and no limitation of the scope of the disclosure is thereby intended. Any such alterations and further modifications in the illustrated embodiments, and any such further applications of the principles of the disclosure as illustrated herein are contemplated as would normally occur to one of ordinary skill in the art.

Figure 1:
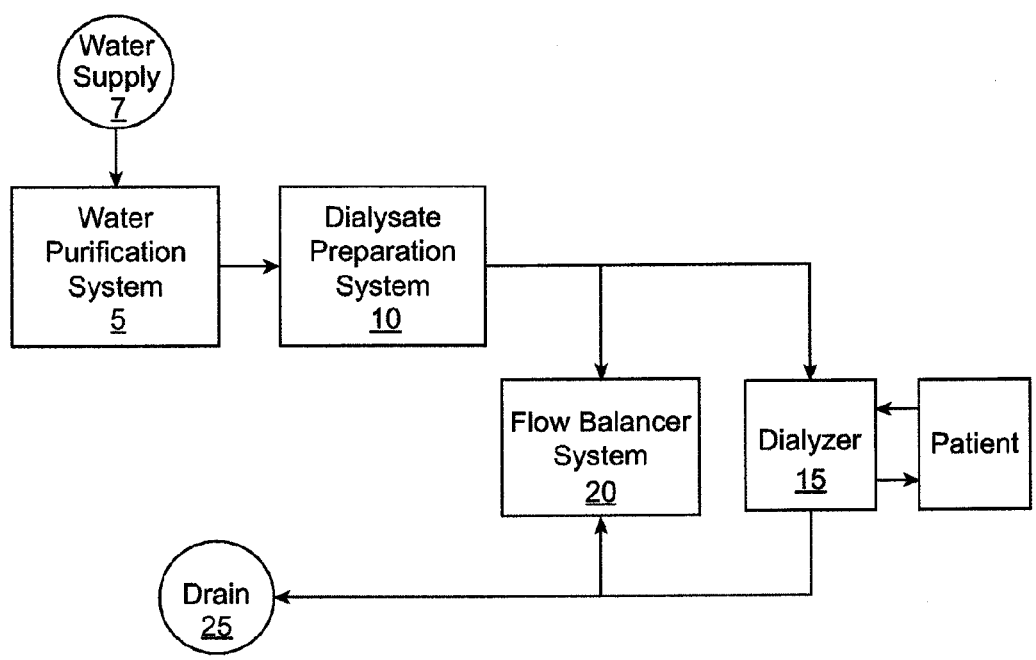
FIG. 1 shows a high level, schematic view of a dialysis system.

FIG. 1 shows a high level, schematic view of a dialysis system. The dialysis system includes a plurality of subsystems that collectively operate to receive and purify water, use the water to prepare dialysate, and supply the dialysate to a dialyzer that performs various types of dialysis on the blood of a patient such as hemodialysis, ultrafiltration and hemodiafiltration. The dialysis system includes plumbing that provides fluid pathways for water, dialysis, and blood to flow through the dialysis system, as well as one or more pumps that interface with the plumbing for driving fluid flow through the system. The dialysis system can also include one or more sensors, such as fluid flow sensors, pressure sensors, conductivity sensors, etc. for sensing and reporting one or more characteristics of fluid flowing through the system.

In an embodiment, the entire dialysis system (including the water preparation and purification system, dialysate preparation system, flow balancer system, dialyzer, and hardware, such as plumbing and sensors) is contained within a single housing that is compact and portable. In addition, the dialysis system can prepare dialysate using a tap water, such as in a home or hotel room. In an embodiment, the entire dialysis system consumes less than about 22" by 14" by 9" of space when dry, which generally corresponds to the size limit for carry-on baggage of an airline. In an embodiment, the entire dialysis system weighs less than about fifty pounds when dry.

With reference still to FIG. 1, the dialysis system includes a water preparation and purification system 5 that purifies water from a water supply 7. The water purification system 5 supplies the purified water to a dialysate preparation system 10 that uses the purified water to prepare dialysate. The dialysis system further includes a dialyzer 15 that receives the dialysate from the dialysate preparation system 10 and performs dialysis on a patient's blood. In an embodiment, the dialyzer 15 and the dialysate preparation system 10 both interface with a flow balancer system 20 that regulates the flow of dialysate to the dialyzer to achieve different types of dialysis, including hemodialysis, ultrafiltration, and hemodiafiltration, as described in detail below.

Diffusion is the principal mechanism in which hemodialysis removes waste products such as urea, creatinine, phosphate and uric acid, among others, from the blood. A differential between the chemical composition of the dialysate and the chemical composition of the blood within the dialyzer causes the waste products to diffuse through a membrane from the blood into the dialysate. Ultrafiltration is a process in dialysis where fluid is caused to move across the membrane from the blood into the dialysate, typically for the purpose of removing excess fluid from the patient's blood stream. Along with water, some solutes are also drawn across the membrane via convection rather than diffusion. Ultrafiltration is a result of a pressure differential between a blood compartment and a dialysate compartment in the dialyzer where fluid moves from a higher pressure to a lower pressure. In some circumstances, by design or unintentional consequence, fluid in the dialysate compartment is higher than the blood compartment causing fluid to move from the dialysate compartment into the blood compartment. This is commonly referred to as reverse ultrafiltration.

In hemodiafiltration, a high level of ultrafiltration is created, greater than the amount required to remove fluid from the patient's blood, for the purpose of increasing convective solute transport across the membrane. The amount of fluid in excess of what is required to be removed from the patient's blood must therefore be returned to the blood stream in order to avoid an adverse hemodynamic reaction. This is accomplished by intentionally increasing the pressure in the dialysate compartment of the dialyzer to cause the appropriate amount of reverse ultrafiltration. This process of ultrafiltration alternating with reverse ultrafiltration is often referred to as "push-pull hemodiafiltration." This is a significant improvement over more common methods of hemodiafiltration where sterile fluid is administered to the patient in a location outside of the dialyzer.

In use, the patient is coupled to the dialyzer 15 such that the patient's blood flows into and out of the dialyzer 15 using devices and techniques known to those skilled in the art. The dialysis system prepares dialysate using water from a household water source, such as a tap, that has been previously prepared through filtration and purification before being mixed with various dialysate components to make the dialysate, and then flows the dialysate through the dialyzer in communication with the blood such that one or more of the dialysis processes on the blood is performed. The water purification system includes a plurality of subsystems that collectively operate to purify the water including pasteurization of the water, as described more fully below. The purified water is then mixed with dialysate concentrates to form dialysate, which is supplied to the dialyzer 15 and to the flow balancer system, which regulates the flow of dialysate to the dialyzer 15 to selectively achieve different types of dialysis, including hemodialysis, ultrafiltration, and hemodiafiltration, as described more fully below. The dialysis system supplies the used dialysate to a drain 25. In an embodiment, the system recaptures heat from the used dialysate before going to the drain.

I. Exemplary Subsystems of Dialysis System

Exemplary embodiments of the various subsystems of the dialysis system are now described, including the water purification system 5, dialysate preparation system 10, dialyzer 15, and flow balancer system 20. It should be appreciated that the descriptions are exemplary and that variations are possible.

1. Water Purification System

Figure 2:
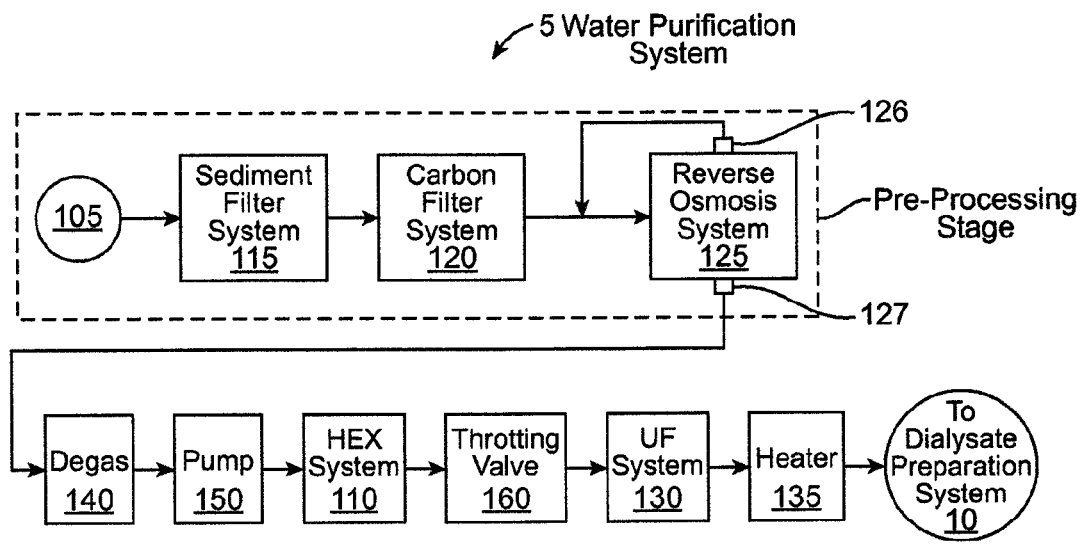
FIG. 2 shows a high level, schematic view of a water purification system of the dialysis system.

FIG. 2 shows a high level, schematic view of the water purification system 5. The water purification system 5 includes a plurality of subsystems and/or components each of which is schematically represented in FIG. 2. Although it is described in the context of purifying water, the water purification system 5 can be used to purify fluids other than water. Water enters the fluid purification system at an entry location 105 (from the water supply 7 in FIG. 1) and communicates with each of the subsystems and components as the water flows along a flow pathway toward the dialysate preparation system 10. The subsystems may include, for example, a sediment filter system 115, a carbon filter system 120, a reverse osmosis system 125, an ultrafilter system 130, an auxiliary heater system 135, a degassifier system 140, or any combination thereof.

Upon exiting the fluid purification system 5, and prior to entering the dialysate preparation system 10, the fluid is in a purified state. This preferably includes the fluid being in a pasteurized state although the fluid system does not necessarily pasteurize the fluid in all circumstances. The embodiment shown in FIG. 2 is exemplary and not all of the components shown in FIG. 2 are necessarily included in the water purification system 5. The individual components included in the system may vary depending on the type and level of purification or pasteurization required. The quantity and sequential order of the subsystems along the flow pathway shown in FIG. 2 is for purposes of example and it should be appreciated that variations are possible.

An exemplary method for purifying water using the fluid purification system 5 is now described including a description of a fluid flow path through the system. As mentioned, water enters the water purification system 5 via an entry location 105. The entry location may include a three-way valve that may be set such that incoming water is received from one of at least two water sources. One such water source may be household water tap. Alternately, the valve may be set to receive recirculated water that was previously routed through the water purification system 5 and that is re-routed back into the system such as to flush the system. When the valve is set to receive recirculated water, the re-circulated water may bypass one or more of the subsystems as it flows through the water purification system 5.

When the valve is set to receive water from the household water tap, the incoming water first flows through at least one sediment filter system 115, which includes one or more sediment filters that filter sediment from the water flowing therethrough. In an embodiment, the sediment filter 115 removes particulate matter down to 5 microns or even 1 micron. A pressure sensor may be positioned upstream of the sediment filter(s) and a pressure sensor may also be positioned downstream of the sediment filter(s) in order to monitor flow conditions. In addition, the flow pathway may include one or more pressure regulators configured to regulate fluid pressure to achieve a desired flow rate through the system. The pressure regulator(s) may be used to compensate for a household tap having a flow rate that is above or below a desired range.

The water then flows through a carbon filter system 120, which includes one or more carbon filters that filter materials such as organic chemicals, chlorine and chloramines from the water. In an embodiment, the carbon filter system 120 includes two carbon filters with a sample port positioned in the flow path between the carbon filters. The sample port provides an operator with access to the water flowing through the system, such as for quality control purposes. In an embodiment, at least one pressure sensor and at least one conductivity sensor are positioned in the flow pathway downstream of the carbon filter system 120. The conductivity sensor provides an indication as to the percentage of dissolved solids removed from the water. In addition, one or more pumps may be positioned at various locations along the water flow pathway such as between the filter subsystems.

The water flows from the carbon filter system 120 to a reverse osmosis system 125 configured to remove particles from the water pursuant a reverse osmosis procedure. The reverse osmosis system 125 usually removes greater than 95% of the total dissolved solids from the water. The reverse osmosis system 125 may have two outlets including a waste water outlet 126 and a pure water outlet 127. The waste water outlet 126 outputs waste water from the reverse osmosis system 125. The waste water can be rerouted back into an upstream location of the water pathway for re-entry into the reverse osmosis system 125. In this regard, a sensor such as a conductivity sensor may be located upstream of the reverse osmosis system 125 as a means of verifying the contents of the water. Alternately, the waste water outlet 126 may supply the waste water to a drain.

The sediment filter system 115, carbon filter system 120, and reverse osmosis system 125 collectively form a pre-processing stage that removes a majority of dissolved solids, bacteria contamination, and chemical contamination, if any, from the water. The water is therefore in a somewhat macro-purified state as it exits the pre-processing stage. Thus, the preprocessing stage supplies relatively clean water to the downstream pump(s) and also to a downstream heat exchange system 110 that pasteurizes the water. The preprocessing stage reduces or eliminates the potential for scale build-up and corrosion during heating of the water by the heat exchange system 110.

One or more degassifier systems 140 may be positioned in the flow pathway upstream and/or downstream of the heat exchange system 110 for removing entrained gas from the water. The degassifier system 140 may include any of a variety of components adapted to remove entrained gas from the water. For example, the degassifier systems 140 may include a spray chamber and/or a bubble trap.

After the water passes the pre-processing stage, the water flows through a pump 150 that pumps the water into the heat exchange (HEX) system 110. The heat exchange system 110 heats the water to a temperature that achieves pasteurization of the water. In an embodiment, the heat exchange system 110 is a microfluidic heat exchange system. Several exemplary embodiments of microfluidic heat exchange systems are described in detail below. The heat exchange system 110 may be encased in insulation to reduce the likelihood of heat loss of the water passing therethrough.

The pump 150 may be used to increase the water pressure to a level higher than the saturation pressure encountered in the heat exchange system 110. This prevents phase change of the water inside the heat exchange system 110. Thus, if the highest temperature reached in the heat exchange system 110 is 150 degrees Celsius where the water would have a saturation pressure known to one of skill in the art, the pressure of the water coming out of the pump would exceed that saturation pressure by a certain safety margin, such as 10 psi, to ensure that no phase change occurs. The pump desirably increases the water pressure to a level that is at or exceeds the saturation pressure to ensure no localized boiling. This can be important where the heat exchange system is used to pasteurize water and the water is exposed to high temperatures that may be greater than 138 degrees Celsius, i.e., well above the boiling point of water at atmospheric pressure.

After leaving the heat exchange system 110, the water passes into a throttling valve 160, such as flow restrictor, which maintains the pressure though the water path from the pump 150 to outlet of the heat exchange system 110. The throttling valve 160 and the pump 150 may be controlled and adjusted to achieve a flow rate and a desired pressure configuration. The pump 150 and the throttling valve 160 may communicate with one another in a closed loop system to ensure the required pressure is maintained for the desired flow rate and temperature. One or more temperature sensors and/or flow sensors may be positioned along the flow pathway downstream of the heat exchange system for use in controlling the pump 150 and the throttling valve 160.

After the water leaves the throttling valve 160, it passes to an ultrafilter (UF) system 130 that removes macromolecules and all or substantially all of the dead bacteria killed by the pasteurization process from the water to ensure no endotoxins remain in the water before mixing the dialysate. The presence of macromolecules may be detrimental to the dialysis process. The water then passes through a heater system 135 that may, if necessary or desired, heat the water to a desired temperature, such as to normal body temperature (98.6 degrees Fahrenheit). From the heater system 135, the water passes to the dialysate preparation system 10.

In an embodiment, a second heat exchange system is positioned in the flow pathway upstream of the heater system 135.

The second heat exchange system is used to further cool the water that comes out of the heat exchange system 110 in the event that the water is above a predetermined desired temperature, such as 37 degrees Celsius. The second heat exchange system may be connected to a separate source of cool water that will then act as a cooling agent or it can be connected to the water rejected from the reverse osmosis system 125. The second heat exchange system may be used in environments where the water source produces very warm water and/or when the heat exchange system 110 is unable to cool the water sufficiently for use in dialysis.

2. Microfluidic Heat Exchange System

Figure 3:
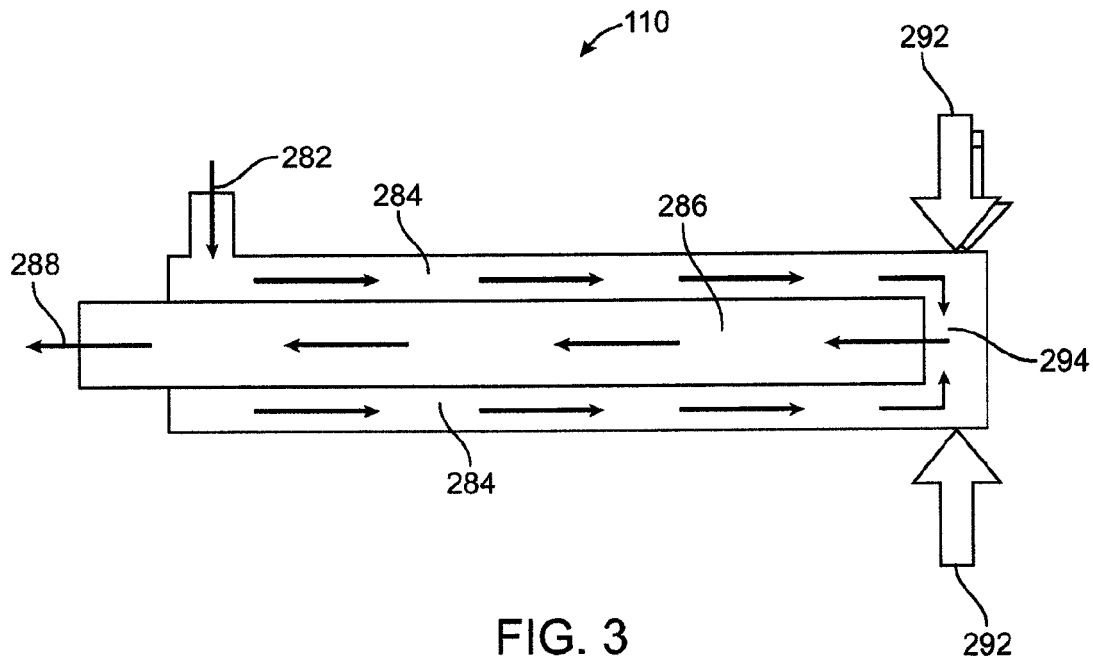
FIG. 3 shows a schematic, plan view of an exemplary embodiment of a microfluidic heat exchange system adapted to heat and cool a single fluid without the use of a second fluid stream to add heat to or remove heat from the fluid.

As discussed above, the water purification system 5 may employ a heat exchange system 110 that is adapted to pasteurize the water. FIG. 3 shows a schematic, plan view of an exemplary embodiment of the microfluidic heat exchange system 110, which is configured to achieve pasteurization of a liquid (such as water) flowing through the microfluidic heat exchange system without the need for a second fluid stream to add heat to or remove heat from the liquid. FIG. 3 is schematic and it should be appreciated that variations in the actual configuration of the flow pathway, such as size and shape of the flow pathway, are possible.

As described more fully below, the microfluidic heat exchange system defines a fluid flow pathway that includes (1) at least one fluid inlet; (2) a heater region where incoming fluid is heated to a pasteurization temperature via at least one heater; (3) a residence chamber where fluid remains at or above the pasteurization temperature for a predetermined time period; (4) a heat exchange section where incoming fluid receives heat from hotter (relative to the incoming fluid) outgoing fluid, and the outgoing fluid cools as it transfers heat to the incoming fluid; and (5) a fluid outlet where outgoing fluid exits in a cooled, pasteurized state. Depending on the desired temperature of the outgoing fluid, one or more additional heat exchanges may be used downstream to adjust the actual temperature of the outgoing fluid to the desired temperature for use, for example, in dialysis. This is especially true in warmer climates, where incoming water may be tens of degrees higher than water supplied in colder climates, which will result in higher outlet temperatures than may be desired unless further cooling is applied.

In an embodiment, the flow pathway is at least partially formed of one or more microchannels, although utilizing microfluidic flow fields as disclosed below for portions of the fluid flow pathway such as the heat exchange section is also within the scope of the invention. The relatively reduced dimensions of a microchannel enhance heat transfer rates of the heat exchange system by providing a reduced diffusional path length and amount of material between counterflow pathways in the system. In an embodiment, a microchannel has at least one dimension less than about 1000 µm. The dimensions of a microchannel can vary and are generally engineered to achieve desired heat transfer characteristics. A microchannel in the range of about 0.1 to about 1 mm in hydraulic diameter generally achieves laminar fluid flow through the microchannel, particularly in a heat exchange region of the microchannel. The small size of a microchannel also permits the heat exchange system 110 to be compact and lightweight. In an embodiment, the microchannels are formed in one or more laminae that are arranged in a stacked configuration, as formed below.

The flow pathway of the microfluidic heat exchange system 110 may be arranged in a counterflow pathway configuration. That is, the flow pathway is arranged such that cooler, incoming fluid flows in thermal communication with hotter, outgoing fluid. The hotter, outgoing fluid transfers thermal energy to the colder, incoming fluid to assist the heaters in heating the incoming fluid to the pasteurization temperature. This internal preheating of the incoming fluid to a temperature higher than its temperature at the inlet reduces the amount of energy used by the heaters to reach the desired peak temperature. In addition, the transfer of thermal energy from the outgoing fluid to the incoming fluid causes the previously heated, outgoing fluid to cool prior to exiting through the fluid outlet. Thus, the fluid is "cold" as it enters the microfluidic heat exchange system 110, is then heated (first via heat exchange and then via the heaters) as it passes through the internal fluid pathway, and is "cold" once again as it exits the microfluidic heat exchange system 110. In other words, the fluid enters the microfluidic heat exchange system 110 at a first temperature and is heated (via heat exchange and via the heaters) to a second temperature that is greater than the first temperature. As the fluid follows an exit pathway, the fluid (at the second temperature) transfers heat to incoming fluid such that the fluid drops to a third temperature that is lower than the second temperature and that is higher than the first temperature.

Exemplary embodiments of a fluid pathway and corresponding components of the microfluidic heat exchange system 110 are now described in more detail with reference to FIG. 3, which depicts a bayonet-style heat exchanger, with the inlet and outlet on one side of the device, a central heat exchange portion, and a heating section toward the opposite end. The fluid enters the microfluidic heat exchange system 110 through an inlet 282. In the illustrated embodiment, the flow pathway branches into one or more inflow microchannels 284 that are positioned in a counterflow arrangement with an outflow microchannel 286. As mentioned, microfluidic heat exchange system 110 may be formed by a stack of layered lamina. The inflow microchannels 284 may be positioned in separate layers with respect to the outflow microchannels 286 such that inflow microchannels 284 are positioned above or below the outflow microchannels 286 in an interleaved fashion. In another embodiment, the inflow microchannels 284 and outflow microchannels 286 are positioned on a single layer.

The outflow microchannel 286 communicates with an outlet 288. In the illustrated embodiment, the inlet 282 and outlet 288 are positioned on the same end of the microfluidic heat exchange system 110, although the inlet 282 and outlet 288 may also be positioned at different positions relative to one another.

The counterflow arrangement places the inflow microchannels 284 in thermal communication with the outflow microchannel 286. In this regard, fluid in the inflow microchannels 284 may flow along a directional vector that is oriented about 180 degrees to a directional vector of fluid flow in the outflow microchannels 286. The inflow and outflow microchannels may also be in a cross flow configuration wherein fluid in the inflow microchannels 284 may flow along a directional vector that is oriented between about 180 degrees to about 90 degrees relative to a directional vector of fluid flow in the outflow microchannels 286. The orientation of the inflow microchannels relative to the outflow microchannels may vary in any matter that is configured to achieve the desired degree of thermal communication between the inflow and outflow microchannels.

One or more heaters 292 are positioned in thermal communication with at least the inflow microchannels 284 such that the heaters 292 can provide heat to fluid flowing in the system. The heaters 292 may be positioned inside the inflow microchannels 284 such that fluid must flow around multiple sides of the heaters 292. Or, the heaters 292 may be positioned to the side of the inflow microchannels 284 such that fluid flows along one side of the heaters 292. In any event, the heaters 292 transfer heat to the fluid sufficient to cause the temperature of the fluid to achieve a desired temperature, which may include a pasteurization temperature in the case of water to be purified. In an embodiment, the fluid is water and the heaters 292 assist in heating the fluid to a temperature of at least 100 degrees Celsius at standard atmospheric pressure. In an embodiment, the fluid is water and the heaters 292 assist in heating the fluid to a temperature of at least 120 degrees Celsius. In an embodiment, the fluid is water and the heaters 292 assist in heating the fluid to a temperature of at least 130 degrees Celsius. In an embodiment, the fluid is water and the heaters 292 assist in heating the fluid to a temperature of at least 138 degrees Celsius. In another embodiment, the fluid is water and is heated to a temperature in the range of about 138 degrees Celsius to about 150 degrees Celsius. In another embodiment, the fluid is heated to the highest temperature possible without achieving vaporization of the fluid.

Thus, the microfluidic heat exchange system 110 may maintain the fluid as a single phase liquid. Because water typically changes phases from a liquid into a gaseous state around 100 degrees Celsius, heating water to the temperatures set forth above requires pressurization of the heat exchange system so that the single-phase liquid is maintained throughout. Pressures above the saturation pressure corresponding to the highest temperature in the heat exchange system are sufficient to maintain the fluid in a liquid state. As a margin of safety, the pressure is typically kept at 10 psi or higher above the saturation pressure. In an embodiment, the pressure of water in the microfluidic heat exchange system is maintained greater than 485 kPa to prevent boiling of the water, and may be maintained significantly in excess of that level, such as 620 kPa or even as high as 900 kPa, in order to ensure no boiling occurs. These pressures are maintained in the heat exchange system using a pump and a throttling valve. A pump upstream of the heat exchange system and a throttling valve downstream of the heat exchange system are used where the pump and throttling valve operate in a closed loop control setup (such as with sensors) to maintain the desired pressure and flow rate throughout the heat exchange system.

Once the fluid has been heated to the pasteurization temperature, the fluid passes into a residence chamber 294 where the fluid remains heated at or above the pasteurization temperature for a predetermined amount of time, referred to as the "residence time", or sometimes referred to as the "dwell time". In an embodiment, the dwell time can be less than or equal to one second, between one and two seconds, or at least about two seconds depending on the flow path length and flow rate of the fluid. Higher temperatures are more effective at killing bacteria and shorter residence times mean a more compact device. Ultrahigh temperature pasteurization, that is designed to kill all Colony Forming Units (CFUs) of bacteria down to a concentration of less than $10^{-6}$ CFU/ml (such as for purifying the water for use with infusible dialysate), is defined to be achieved when water is heated to a temperature of 138 degrees Celsius to 150 degrees Celsius for a dwell time of at least about two seconds. Ultrapure dialysate has a bacterial load no greater than 0.1 CFU/ml. Table 1 (shown in the attached figures) indicates the required temperature and residence time to achieve various levels of pasteurization. The heat exchange system described herein is configured to achieve the various levels of pasteurization shown in Table 1.

The fluid then flows from the residence chamber 294 to the outflow microchannel 286, where it flows toward the fluid outlet 288. As mentioned, the outflow microchannel 286 is positioned in a counterflow relationship with the inflow microchannel 284 and in thermal communication with the inflow microchannel 284. In this manner, outgoing fluid (flowing through the outflow microchannel 286) thermally communicates with the incoming fluid (flowing through the inflow microchannel 284). As the heated fluid flows through the outflow microchannel 286, thermal energy from the heated fluid transfers to the cooler fluid flowing through the adjacent inflow microchannel 284. The exchange of thermal energy results in cooling of the fluid from its residence chamber temperature as it flows through the outflow microchannel 286. Moreover, the incoming fluid is preheated via the heat exchange as it flows through the inflow microchannel 284 prior to reaching the heaters 292. In an embodiment, the fluid in the outflow microchannel 284 is cooled to a temperature that is no lower than the lowest possible temperature that precludes bacterial infestation of the fluid. When the heat exchange system pasteurizes the fluid, bacteria in the fluid down to the desired level of purification are dead as the fluid exits the heat exchange system. In such a case, the temperature of the fluid after exiting the heat exchange system may be maintained at room temperature before use in dialysis. In another embodiment, the fluid exiting the heat exchange system is cooled to a temperature at or below normal body temperature.

Although an embodiment is shown in FIG. 3 as having an outlet channel sandwiched between an inflow channel, other arrangements of the channels are possible to achieve the desired degrees of heating and cooling and energy requirements of the heaters. Common to all embodiments, however, is that all fluid pathways within the system are designed to be traveled by a single fluid, without the need for a second fluid to add heat to or remove heat from the single fluid. In other words, the single fluid relies on itself, at various positions in the fluid pathway, to heat and cool itself.

The dimensions of the microfluidic heat exchange system 110 may vary. In an embodiment, the microfluidic heat exchange system 110 is sufficiently small to be held in the hand of a user. In another embodiment, the microfluidic heat exchange system 110 is a single body that weighs less than 5 pounds when dry. In another embodiment, the microfluidic heat exchange portion 350 of the overall system 110 has a volume of about one cubic inch. The dimensions of the microfluidic heat exchange system 110 may be selected to achieve desired temperature and dwell time characteristics.

As mentioned, an embodiment of the microfluidic heat exchange system 110 is made up of multiple laminar units stacked atop one another to form layers of laminae. A desired microfluidic fluid flow path may be etched into the surface of each lamina such that, when the laminae are stacked atop one another, microfluidic channels or flow fields are formed between the lamina. Furthermore, both blind etching and through etching may be used for forming the channels in the laminae. In particular, through etching allows the fluid to change the plane of laminae and move to other layers of the stack of laminae. This occurs in one embodiment at the outlet of the inflow laminae where the fluid enters the heater section, as described below. Through etching allows all laminae around the heater section to participate in heating of the fluid instead of maintaining the fluid only in the plane of the inlet laminae. This embodiment provides more surface area and lower overall fluid velocity to facilitate the heating of the fluid to the required temperature and ultimately contributes to the efficiency of the device.

Figure 4A:
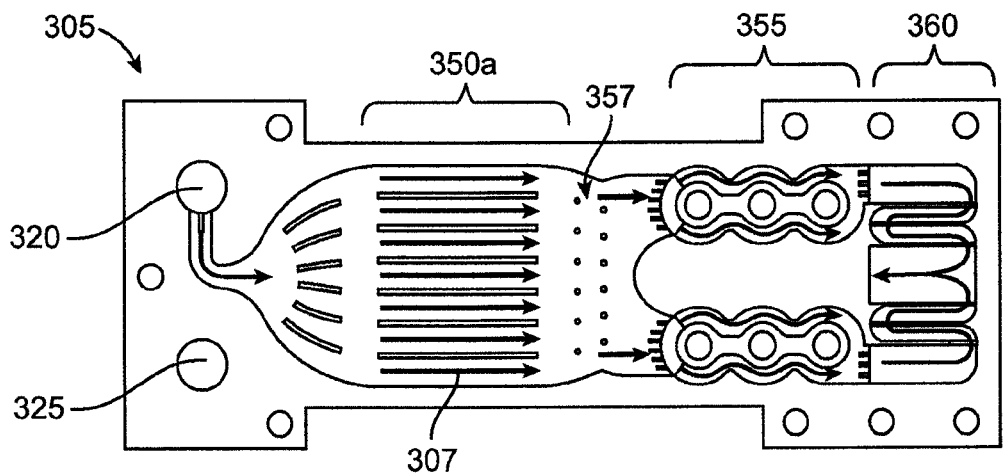
FIG. 4A shows an exemplary embodiment of an inlet lamina that forms at least one inlet pathway where fluid flows in an inward direction through the heat exchange system.
Figure 4B:
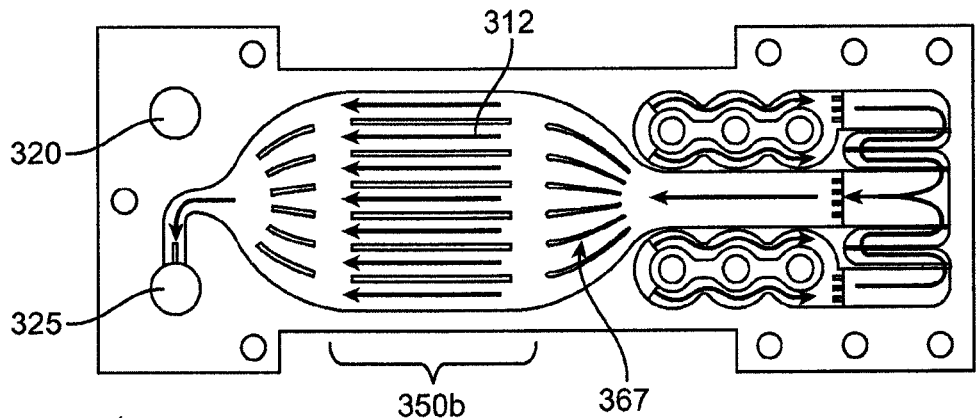
FIG. 4B shows an exemplary embodiment of an outlet lamina that forms at least one outlet pathway where fluid flows in an outward direction through the heat exchange system.

The microchannels or flow fields derived from blind and/or through etching of the laminae form the fluid flow pathways. FIG. 4A shows a plan view of an exemplary embodiment of an inlet lamina 305 that forms at least one inlet pathway where fluid flows in an inward direction (as represented by arrows 307) through the heat exchange system 110. FIG. 4B shows a plan view an exemplary embodiment of an outlet lamina 310 that forms at least one outlet pathway where fluid flows in an outward direction (as represented by arrows 312) through the heat exchange system 110. The inlet pathway and the outlet pathway may each comprise one or more microchannels. In an embodiment, the inlet and outlet pathway comprise a plurality of microchannels arranged in parallel relationship.

FIGS. 4A and 4B show the lamina 305 and 310 positioned adjacent each other, although in assembled device the lamina are stacked atop one another in an interleaved superimposed over one another showing both the inlet pathway and outlet pathway. The inlet lamina 305 and outlet lamina 310 are stacked atop one another with a fluid conduit therebetween so fluid may flow through the conduit from the inlet pathway to the outlet pathway, as described more fully below. When stacked, a transfer layer may be interposed between the inlet lamina 305 and the outlet lamina 310. The transfer layer is configured to permit heat to transfer from fluid in the outlet pathway to fluid in the inlet pathway. The transfer layer may be any material capable of conducting heat from one fluid to another fluid at a sufficient rate for the desired application. Relevant factors include, without limitation, the thermal conductivity of the heat transfer layer 110, the thickness of the heat transfer layer, and the desired rate of heat transfer. Suitable materials include, without limitation, metal, metal alloy, ceramic, polymer, or composites thereof. Suitable metals include, without limitation, stainless steel, iron, copper, aluminum, nickel, titanium, gold, silver, or tin, and alloys of these metals. Copper may be a particularly desirable material. In another embodiment, there is no transfer layer between the inlet and outlet laminae and the laminae themselves serve as the thermal transfer layer between the flow pathways.

Figure 4C:
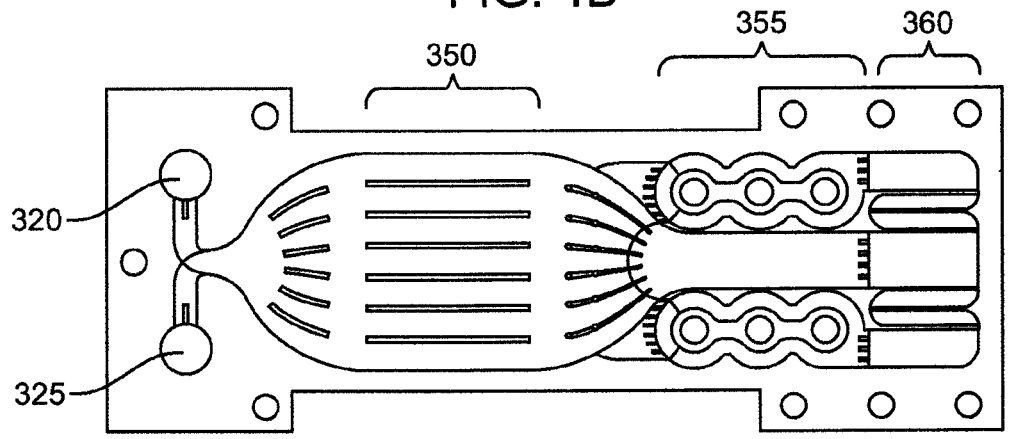
FIG. 4C shows the inlet lamina and outlet lamina superimposed over one another showing both an inlet pathway and an outlet pathway.

The inlet lamina 305 and outlet lamina 310 both include at least one inlet opening 320 and at least one outlet opening 325. When the inlet lamina 305 and outlet lamina 310 are stacked atop one another and properly aligned, the inlet openings 320 align to collectively form a fluid pathway that extends through the stack and communicates with the inlet pathway of the inlet laminae 305, as shown in FIG. 4C. Likewise, the outlet openings 325 also align to collectively form a fluid pathway that communicates with the outlet pathway of the outlet laminae 310. Any quantity of inlet lamina and outlet lamina can be stacked to form multiple layers of inlet and outlet pathways for the heat exchange system 110. The quantity of layers can be selected to provide predetermined characteristics to the microfluidic heat exchange system 110, such as to vary the amount of heat exchange in the fluid, the flow rate of the fluid capable of being handled by the system, etc. In an embodiment, the heat exchange system 110 achieves incoming liquid flow rates of at least 100 ml/min.

In another embodiment, the heat exchange system 110 achieves incoming liquid flow rates of at least 1000 ml/min. Such a heat exchange system may be manufactured of a plurality of laminae in which the microfluidic pathways have been formed using a masking/chemical etching process. The laminae are then diffusion bonded in a stack, as described in more detail below. In an embodiment, the stack includes 40-50 laminae with a flow rate of 2-3 ml/min occurring over each lamina. Higher flow rates can be achieved by increasing the number of pairs of stacked laminae within the heat exchanger. In other embodiments, much higher flow rates can be handled through the system.

In operation, fluid flows into the inlet pathway of the inlet lamina 305 via the inlet opening 320. This is described in more detail with reference to FIG. 5, which shows an enlarged view of an inlet region of the inlet lamina 305. The inlet opening 320 communicates with an inlet conduit 405 that guides the fluid to the inlet pathway. The inlet opening 320 may configured with a predetermined size relative to the size of the inlet conduit 405, which may have a diameter of 2-mm. For example, in an embodiment, the inlet opening 320 has an associated hydraulic diameter that may be about ten to fifteen times larger than the hydraulic diameter of the inlet conduit 405. Such a ratio of hydraulic diameters has been found to force fluid to distribute relatively evenly among the multiple inlet laminae. In another embodiment, for a 2-mm wide inlet flow path, a hydraulic diameter ratio of greater than 10:1, such as 15:1, may be used to ensure an even distribution of fluid flow over the stack.

Figure 5:
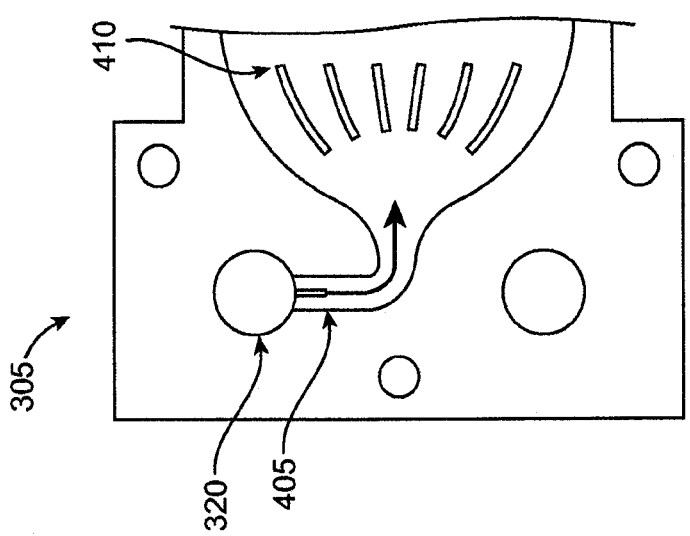
FIG. 5 shows an enlarged view of an inlet region of the inlet lamina.

With reference still to FIG. 5, a downstream end of the inlet conduit 405 opens into the inlet pathway, which flares outward in size relative to the size of the inlet conduit 405. In this regard, one or more flow separation guides, such as fins 410, may be positioned at the entryway to the inlet pathway. The flow separation fins are sized and shaped to encourage an even distribution of fluid as the fluid flows into the inlet pathway from the inlet conduit 405. It should be appreciated that the size, shape, and contour of the inlet conduit 405 and inlet pathway may vary and that the embodiment shown in FIG. 5 is merely exemplary. By way of example only, this region of the system could also comprise a flow field of pin-shaped members (as described below) around which the fluid flows.

With reference again to FIG. 4A, the inlet pathway and outlet pathway each include a heat exchange region. The heat exchange regions are referred to collectively using the reference numeral 350 and individually using reference numeral 350a (for the inlet pathway) and reference numeral 350b (for the outlet pathway). The heat exchange regions 350 are the locations where the colder fluid (relative to the fluid in the outlet pathway) of the inlet pathway receives heat transferred from the hotter fluid (relative to the fluid in the inlet pathway) of the outlet pathway. As discussed above, the relatively colder fluid in the inflow pathway is positioned to flow in thermal communication with the relatively hotter fluid in the outflow pathway. In this layered embodiment, the inflow pathway is positioned immediately above (or below) the outflow pathway when the lamina are stacked. Heat transfers across the transfer layer from the fluid in the outflow pathway to the fluid in the inflow pathway as a result of the temperature differential between the fluid in the inflow pathway and the fluid in the outflow pathway and the thermal conductivity of the material separating the two pathways. Again rather than comprising a series of microchannels, the heat exchange regions may also comprise a microfluidic flow field as described above.

Figure 6:
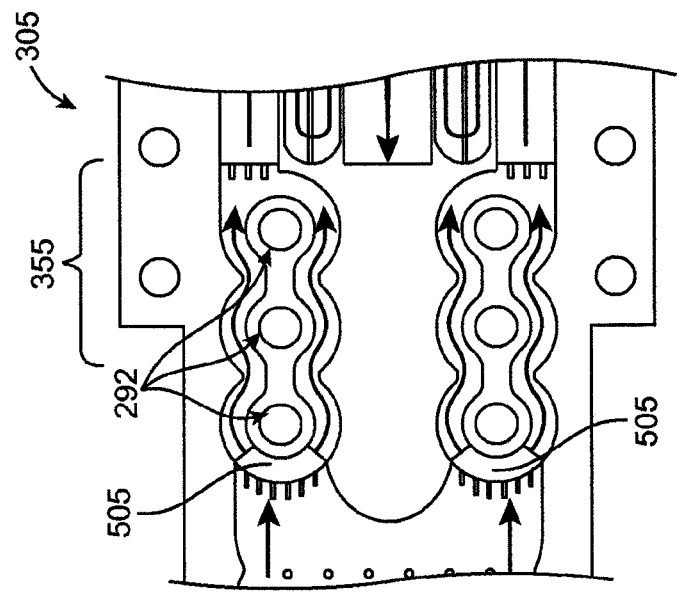
FIG. 6 shows an enlarged view of a heater region of the inlet lamina.

With reference still to FIG. 4A, the fluid in the inflow pathway flows into a heater region 355 from the heat exchange region 350. A plurality of pins 357 may be positioned in the inlet flow pathway between the heat exchange region 350 and the heater region 355. The pins 357 disrupt the fluid flow and promote mixing, which may improve both fluid flow and heat distribution. FIG. 6 shows an enlarged view of the heater region 355. In an embodiment, the inflow pathway bifurcates into at least two flow pathways in the heater region 355 to accommodate a desired flow rate. Alternatively only one flow path through the heater region may be utilized, or three or more flow paths may be selected. The heater region 355 includes one or more heaters 292 that thermally communicate with fluid flowing through this region, but are hermetically isolated from the flow path. The heaters 292 add heat to the incoming fluid sufficient to raise temperature of the fluid to the desired temperature, which may include a pasteurization temperature. The incoming fluid was previously preheated as it flowed through the heat exchange region 350. This advantageously reduced the energy requirements for the heaters.

The laminae in the stack may include through-etches at entry locations 505 to the heater region 355 such that fluid entering the heater region can pass through all the laminae in the stack. Through etching allows all laminae around the heater section to participate in heating of the fluid instead of maintaining the fluid only in the plane of the inlet laminae. This provides more surface area between the fluid and the heaters and also provides lower overall fluid velocity to facilitate the heating of the fluid to the required temperature.

As mentioned, the inflow pathway may bifurcate into multiple flow pathways. Each pathway may include one or more heaters 292 arranged within the pathway so as to maximize or otherwise increase the amount of surface area contact between the heaters 292 and fluid flowing through the pathways. In this regard, the heaters 292 may be positioned towards the middle of the pathway such that the fluid must flow around either side of the heaters 292 along a semicircular or otherwise curvilinear pathway around the heaters 292. The heaters 292 can vary in configuration. In an embodiment, the heaters 292 are conventional cartridge heaters with a ⅛-inch diameter which can be run in an embodiment at a combined rate of between about 70,000 and 110,000 W/m², which results in energy usages of less than 100 W in one embodiment, and less than 200 W in another embodiment, for the entire stack running at about 100 mL/minute. In an embodiment, the system uses six heaters in a configuration of three heaters per flow pathway wherein each heater uses about 70 W for a 100 ml/min flow rate. In an embodiment the fluid is forced to flow around the heaters in paths 1.6 mm wide.

With reference again to FIG. 4A, the inflow pathway transitions from the heater section 355 to the residence chamber 360. By the time the fluid flows into the residence chamber 360, it has been heated to the desired temperature, such as the pasteurization temperature, as a result of the heat transfer in the heat exchange region 350 and/or by being heated in the heater section 355. In the case of multiple laminae being stacked, the residence chamber 360 may be a single chamber that spans all of the layers of laminae in the stack such that the fluid from each inlet lamina flows into a single volume of fluid in the residence chamber 360. The residence chamber 360 is configured such that fluid flow 'shortcuts' are eliminated, all of the fluid is forced to travel a flow pathway such that no portion of the fluid will reside in the residence chamber for the less than the desired duration at a specified flow rate, and the fluid is maintained at or above the pasteurization temperature for the duration of the time (i.e., the dwell time) that the fluid is within the residence chamber 360. In effect, the residence time is a result of the dimensions of the flowpath through the residence area and the flow rate. It will thus be apparent to one of skill in the art how to design a residence pathway for a desired duration.

Figure 7:
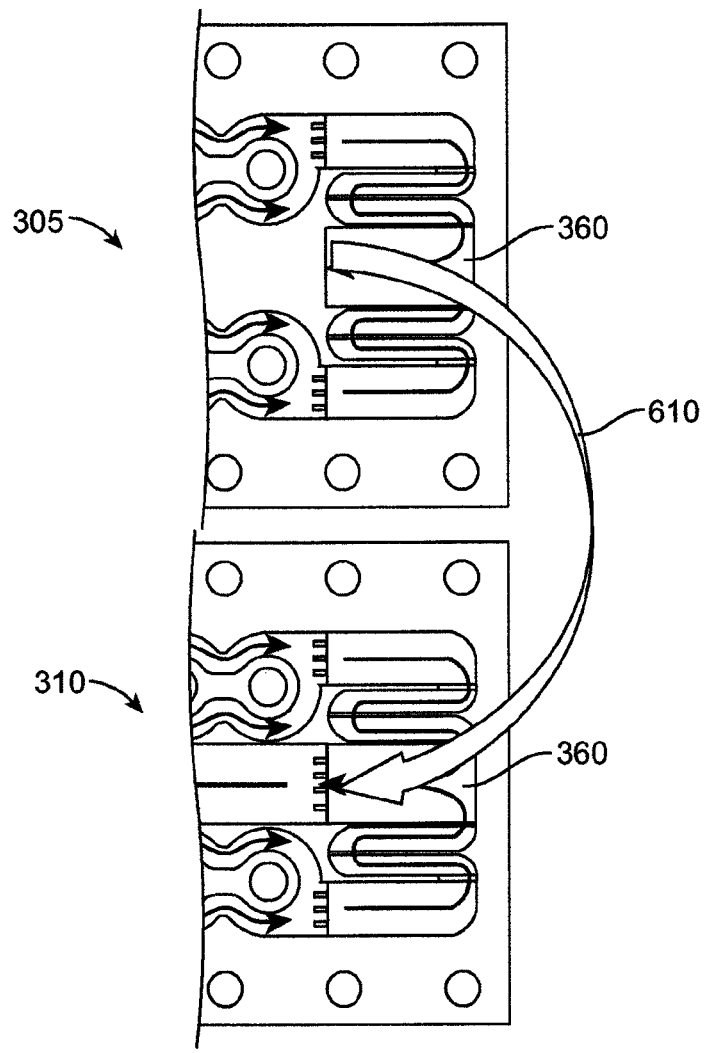
FIG. 7 shows an enlarged view of a residence chamber of both the inlet lamina and outlet lamina.

FIG. 7 shows an enlarged view of the region of the residence chamber 360 for the inlet lamina 305 and outlet lamina 310. For clarity of illustration, FIG. 7 shows the inlet lamina 305 and outlet lamina 310 positioned side-by-side although in use the laminae are stacked atop one another such that the residence chambers align to form a residence chamber that spans upward along the stack. In an embodiment, the residence chamber 360 incorporates a serpentine flow path as shown in the enlarged view of the residence chamber of FIG. 7. The serpentine flow path provides a longer flow path to increase the likelihood of the liquid spending a sufficient amount of time within the residence chamber 360.

After the fluid has reached the end of the serpentine flow path, it passes (represented by arrow 610 in FIG. 7) to the outlet pathway of the outlet lamina 310. With reference now to FIG. 4B, the outlet pathway passes between the heaters 292, which act as insulators for the fluid to lessen the likelihood of the fluid losing heat at this stage of the flow pathway. The heated fluid of the outlet pathway then flows toward the heat exchange region 350b. The outlet flow pathway expands prior to reaching the heat exchange region 350b. A set of expansion fans 367 directs the fluid into the expanded heat exchange region 350b of the outlet pathway, where the fluid thermally communicates with the cooler fluid in the inflow pathway. As discussed, heat from the fluid in the hotter outflow pathway transfers to the cooler fluid in the inflow pathway. This results in cooling of the outflowing fluid and heating of the inflowing fluid. The fluid then flows from the heat exchange region 350b to the outlet opening 325. At this stage, the fluid is in a cooled, pasteurized state.

In an embodiment, laminae having a thickness of 350 microns with an etch-depth of 175 microns, with 2.5-mm wide channels having a hydraulic diameter of 327 microns were utilized. Each pair of laminae was able to handle a fluid flow rate of approximately 3.3 mL/min of fluid, which thus required 30 pairs of laminae in order to facilitate a flow of 100 mL/min, with only a 15 mm long heat exchanger section. In an embodiment, the fluid flowpaths are designed in smooth, sweeping curves and are substantially symmetrically designed along the longitudinal axis of the stack; if the flow paths are not designed symmetrically, they are designed to minimize differences in the path line or lengths so as to evenly distribute the flow, the heating of the fluid and the various dwell times.

The width of the ribs separating channels in the heat exchange portion can be reduced, which would have the effect of increasing the available heat transfer area and reducing the length of the heat exchange portion required for the desired energy efficiency level of the device. Energy efficiency levels of at least about 85%, and in some embodiment of at least about 90% can be achieved, meaning that 90% of the thermal energy from the outgoing fluid can be transferred to the incoming fluid stream and recaptured without loss.

In this manner, a heat exchange system may be constructed to provide pasteurized water continuously at a desired flow rate for real-time mixing of dialysate in a dialysis system, without the need either to heat, purify or store water in batched quantities or to provide bags of pure water or of premixed dialysate for use by the patient. The water purification system processes a water source, such as a household water stream, in a non-batch process to produce an ultra-high-temperature-pasteurized water stream.

FIG. 8A shows a plan view of another embodiment of an inlet lamina 705 that forms at least one inlet pathway where fluid flows in an inward direction (as represented by arrows 707) through the heat exchange system 110. FIG. 8B shows a plan view another embodiment of an outlet lamina 710 that forms at least one outlet pathway where fluid flows in an outward direction (as represented by arrows 712) through the heat exchange system 110. The flow pathway in this embodiment generally follows a different contour than the flow pathway of the embodiment of FIGS. 4A and 4B. In actual use, the inlet lamina 705 and outlet lamina 710 are stacked atop one another.

The fluid enters the inlet pathway of the inlet lamina 705 at an inlet 720. The inlet pathway then splits into multiple pathways at the heat exchange region 750a, which thermally communicates with a corresponding heat exchange region 750b of the outlet lamina 710. In another embodiment, the inlet pathway does not split into multiple pathways but remains a single pathway. The inlet pathway could also be at least partially formed of one or more microfluidic flow fields as described below. After the heat exchange region 750a, the inlet pathway transitions to an arc-shaped heater region 760 that thermally communicates with a heater 765, such as a 150-Watt McMaster-Carr cartridge heater (model 3618K451). The heater region serves as both a region where the heater 765 heats the fluid and as a residence chamber where the fluid remains heated at or above the desired temperature for a predetermined amount of time.

From the heater region 760 and residence chamber of the inlet lamina 705, the fluid flows to the outlet lamina 710 at an entrance location 770. The fluid then flows into the heat exchange region 750b of the outlet lamina 710, where the fluid transfers heat to the incoming fluid flowing through the heat exchange region 750a of the inlet lamina 705. The fluid then exits the outlet lamina at an outlet 775. In embodiment, the lamina 705 and 710 are about 600 µm thick and the microfluidic flow pathways have a depth of about 400 µm to 600 µm. In each of the embodiments disclosed herein, the fluid flow path completely encircles each of the heaters so that any shim material conducting heat away from the heater will have fluid flowing over it to receive the heat, thereby minimizing heat loss to the environment. In addition, ideally, the flowpaths around each heater will be relatively narrow so that non-uniform heating due to separation from the heaters will be avoided.

As mentioned, the microfluidic heat exchange system 110 may be formed of a plurality of lamina stacked atop one another and diffusion bonded. Additional information concerning diffusion bonding is provided by U.S. patent application Ser. Nos. 11/897,998 and 12/238,404, which are incorporated herein by reference. In an embodiment, the stack includes multiple sets of lamina with each set including an inlet lamina 305 juxtaposed with an outlet lamina 310. Each set of juxtaposed inlet lamina and outlet lamina forms a single heat exchange unit. The stack of lamina may therefore include a plurality of heat exchange units wherein each unit is formed of an inlet lamina 305 coupled to an outlet lamina 310. The flow pathways for each lamina may be formed by etching on the surface of the lamina, such as by etching on one side only of each lamina. When the laminae are juxtaposed, the etched side of a lamina seals against the unetched sided of an adjacent, neighboring lamina. This may provide desirable conditions for heat exchange and separation of the incoming fluid (which is not pasteurized) and the outgoing fluid (which is pasteurized).

Figure 9:
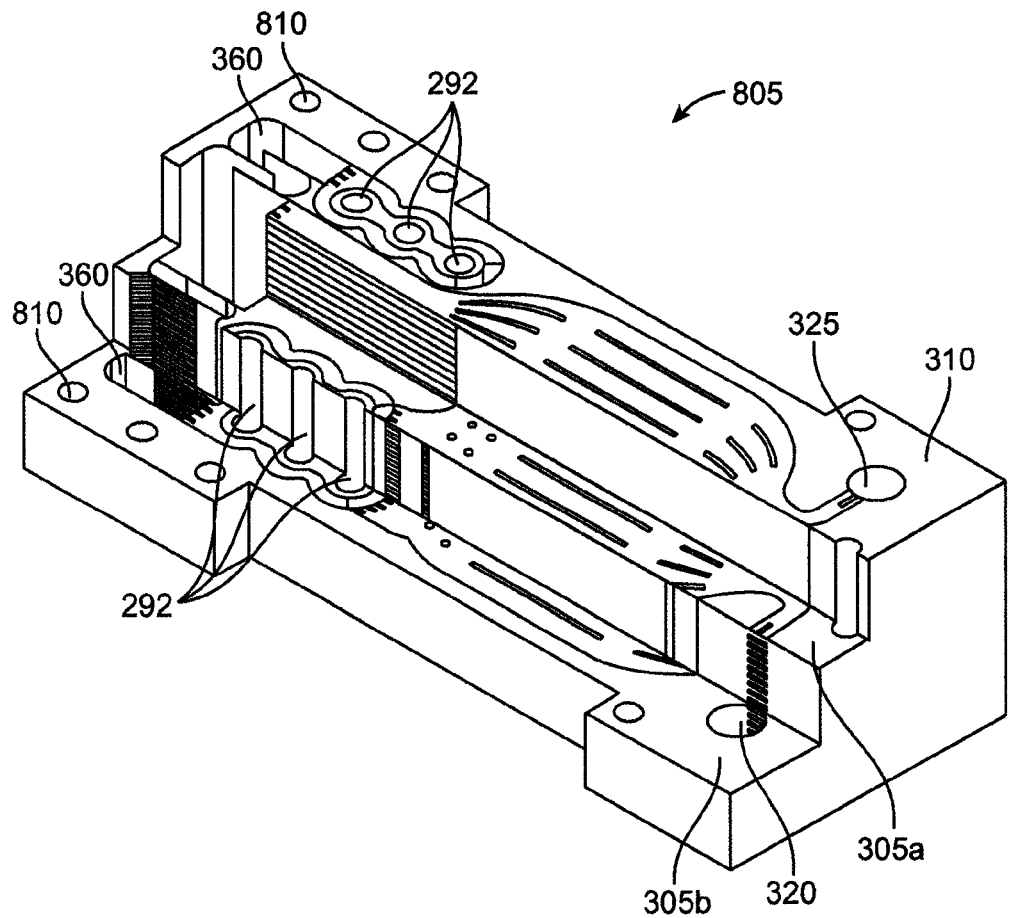
FIG. 9 shows a perspective view of an exemplary stack of laminae.

FIG. 9 shows a perspective view of an exemplary stack 805 of laminae. The stack 805 is shown in partial cross-section at various levels of the stack including at an upper-most outlet lamina 310, a mid-level inlet lamina 305a, and a lower level inlet lamina 305b. As mentioned, the stack 805 is formed of alternating inlet lamina and outlet lamina interleaved with one another. The heaters 292 are positioned within cut-outs that extend through the entire stack 805 across all the laminae in the stack 805. The residence chamber 360 and the aligned inlet openings 320 and outlet openings 325 also extend entirely through the stack 805. The laminae may also include one or more holes 810 that align when the lamina are stacked to form shafts through which alignment posts may be inserted.

The quantity of laminae in the stack may be varied to accommodate desired specifications for the microfluidic heat exchange system 110, such as the heating specifications. The heating specifications may be dependent on flow rate of fluid, heater power input, initial temperature of incoming fluid, etc. In an embodiment, the stack 805 is less than about 100 mm long, less than about 50 mm wide at its widest dimension, and less than about 50 mm deep, with a volume of less than about 250 cubic centimeters, although the dimensions may vary. In another embodiment, the stack 805 is about 82 mm long, about 32 mm wide at its widest dimension, and about 26 mm deep, with a volume of about 69-70 cubic centimeters, and a weight of about five pounds when dry, although the dimensions may vary.

The lamina 305 and 310 may be any material capable of being patterned with features useful for a particular application, such as microchannels. The thickness of the lamina may vary. For example, the lamina may have a thickness in the range of about 200 µm to about 100 µm. In another embodiment, the lamina may have a thickness in the range of about 500 µm to about 100 µm. Some suitable lamina materials include, without limitation, polymers and metals. The lamina may be manufactured of any diffusion bondable metal, including stainless steel, copper, titanium alloy, as well as diffusion bondable plastics. Because of the operating pressures and temperatures involved, the need to avoid leaching of the lamina material into the heated fluid, such as water, and the desirability of multiple uses of this device before disposal, it has been found that manufacturing the heat exchange system from stainless steel, such as 316L stainless steel, has proven adequate, although other materials may be used as long as they withstand the operating conditions without degradation.

The laminae are stacked in a manner that achieves proper alignment of the lamina. For example, when properly stacked, the inlet openings 320 of all the lamina align to collectively form an inlet passage for fluid to flow into the system and the outlet openings 325 align to collectively form an outlet passage, as shown in FIG. 9. The properly-aligned stack of lamina may also include one or more seats for coupling the heaters 292 in the stack. One or more features can be used to assist in proper alignment of the lamina in the stack, such as alignment posts and/or visual indicators of proper alignment. The stack may include a top cover positioned on the top-most lamina and a bottom cover positioned on the bottom-most lamina. The stack may also include an external insulation wrap to prevent heat loss to the outside environment.

Figure 10:
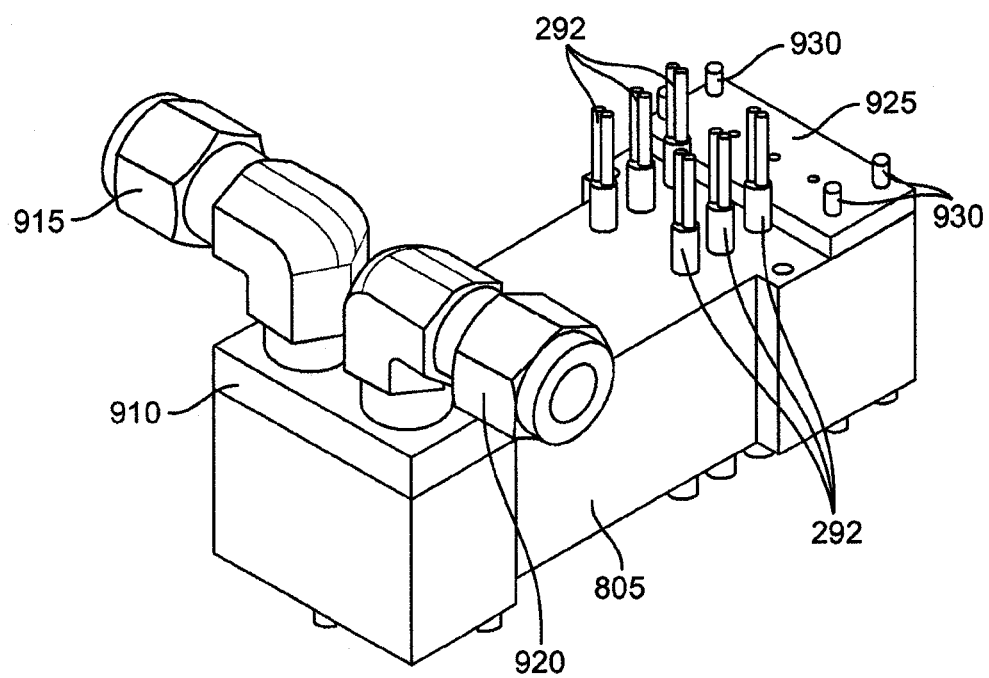
FIG. 10 shows a perspective view of an example of an assembled microfluidic heat exchange system.

FIG. 10 shows a perspective view of an example of an assembled microfluidic heat exchange system 110. The stack 805 of inlet/outlet laminae includes chemically etched upper and lower covers that seal the stack 805 against the atmosphere. These covers typically are thicker than the laminae, and may be about 1 mm or more in thickness in an embodiment to withstand damage and the operating pressures necessary to maintain the fluid in a single state. The cartridge heaters 292 are mounted in cavities that extend through the entire stack 805. A plate 910 is secured (such as via bolts) to the stack and provides a means of securing an inlet port 915 and an outlet port 920 to the stack 805. The inlet port 915 and outlet port 920 can be piping having internal lumens that communicate with the inlet openings 320 and outlet openings 325.

Before assembly of the stack, each hole of each lamina that is to accept a cartridge heater is designed slightly smaller than the diameter of the cartridge heater itself. After assembly of the entire stack, the hole is enlarged for a clearance fit between the hole inner diameter and the cartridge heater outer diameter, taking into account thermal expansion of the heater during operation, to provide a uniform surface for optimum heat transfer from the heater to the pasteurizer. This method avoids any potential issues with misalignment of the shims if the holes in each shim were to be properly sized to the cartridge heater prior to assembly.

A second plate 925 is also secured to the stack 805. The plate 925 is used to couple one or more elongated and sheathed thermocouples 930 to the stack 805. The thermocouples 930 extend through the stack 805 and communicate with the laminae in the stack 805 in the region of the dwell chamber for monitoring fluid temperature in the dwell chamber. The thermocouples that are to be inserted into solid sections of the stack utilize a slip fit for installation. The thermocouples that enter into the fluid flow paths require a seal to prevent fluid leakage. In these cases, the holes for accepting the thermocouples are generated after the stack is assembled by electrical discharge machining (EDM), because this technique generates very small debris that can easily be flushed out of the system, as compared with traditional drilling, which could result in larger debris blocking some of the flow paths. Any of a variety of sealing members, such as o-rings or gaskets, may be coupled to the stack to provide a sealed relationship with components attached to the stack, such as the plates 910 and 925, thermocouples 930, and inlet port 915 and outlet port 920. It should be appreciated that the assembled microfluidic heat exchange system 110 shown in FIG. 10 is an example and that other configurations are possible.

In an exemplary manufacture process, a stack of lamina is positioned in a fixture or casing and is then placed into a bonding machine, such as a high temperature vacuum-press oven or an inert gas furnace. The machine creates a high temperature, high pressure environment that causes the lamina to physically bond to one another.

In an embodiment, the weight of the overall stack can be reduced by removing some of the excess material from the sides of the stack, thereby eliminating the rectangular footprint in favor of a more material-efficient polygonal footprint.

Figure 11:
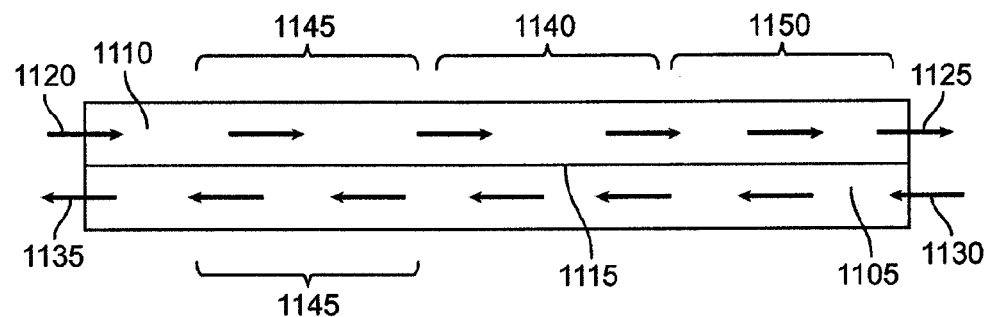
FIG. 11 shows a schematic view of an exemplary heater control system coupled to the microfluidic heat exchange system.

FIG. 11 shows a schematic, plan view of another exemplary embodiment of the microfluidic heat exchange system 110. FIG. 11 is schematic and it should be appreciated that variations in the actual configuration of the flow pathway, such as size and shape of the flow pathway, are possible. The embodiment of FIG. 11 includes a first flow pathway 1110 and a second flow pathway 1105 separated by a transfer layer 1115. Fluid enters the first flow pathway at an inlet 1120 and exits at an outlet 1125. Fluid enters the second flow pathway at an inlet 1130 and exits at an outlet 1135. The first and second flow pathways are arranged in a counterflow configuration such that fluid flows through the first flow pathway 1110 in a first direction and fluid flows through the second flow pathway 1105 in a direction opposite the first direction. In this regard, the inlet 1120 of the first flow pathway 1110 is located on the same side of the device as the outlet 1135 of the second flow pathway 1105. Likewise, the outlet 1125 of the first flow pathway 1110 is located on the same side of the device as the inlet 1130 of the second flow pathway 1105. The flow pathways may be least partially formed of one or more microchannels or flow fields.

With reference still to FIG. 11, fluid enters the first flow pathway 1110 at the inlet 1120 and passes through a heater region 1140. A heater is positioned in thermal communication with the heater region 1140 so as to input heat into the fluid passing through the heater region 1140. Prior to passing through the heater region 1140, the fluid passes through a heat exchange region 1145 that is in thermal communication (via the transfer layer 1115) with fluid flowing through the second flow pathway 1105. In an embodiment, the fluid flowing through the second flow pathway 1105 is fluid that previously exited the first flow pathway 1110 (via the outlet 1125) and was routed into the inlet 1130 of the second flow pathway 1105. As the previously-heated fluid flows through the second flow pathway 1105, thermal energy from the previously-heated fluid in the second flow pathway 1105 transfers to the fluid flowing through the first flow pathway 1110. In this manner, the fluid in the second flow pathway 1105 pre-heats the fluid in the heat exchange region 1145 of the first flow pathway 1110 prior to the fluid reaching the heater region 1140.

In the heater region 1140, the heater provides sufficient thermal energy to heat the fluid to a desired temperature, which may be the pasteurization temperature of the fluid. From the heater region 1140, the fluid flows into a residence chamber 1150 where the fluid remains heated at or above the desired temperature for the residence time. The fluid desirably remains flowing, rather than stagnant, while in the residence chamber 1150. From the residence chamber 1150, the fluid exits the first flow pathway 1110 through the outlet 1125 and is routed into the inlet 1130 of the second flow pathway 1105.

The fluid then flows through the second flow pathway 1105 toward the outlet 1135. As mentioned, the second flow pathway 1105 is in thermal communication with the first flow pathway 1110 at least at the heat exchange region 1145. In this manner, the previously-heated fluid flowing through the second flow pathway 1105 thermally communicates with the fluid flowing through the first flow pathway 1110. As the previously-heated fluid flows through the second flow pathway 1105, thermal energy from the heated fluid transfers to the fluid flowing through the adjacent heat exchange region 1145 of the first flow pathway 1110. The exchange of thermal energy results in cooling of the fluid from its residence chamber temperature as it flows through the second flow pathway 1105. In an embodiment, the fluid in the second flow pathway 1105 is cooled to a temperature that is no lower than the lowest possible temperature that precludes bacterial infestation of the fluid.

In another embodiment of the device of FIG. 11, the fluid flowing into the second flow pathway 1105 is not fluid re-routed from the first flow pathway 1110 but is rather a separate fluid flow from the same source as, or from a different source than, the source for the first fluid flow pathway 1110. The fluid in the second flow pathway 1105 may or may not be the same type of fluid in the first flow pathway 1110. For example, water may flow through both pathways; or water may flow through one flow pathway and a non-water fluid may flow through the other flow pathway. In this embodiment where a separate fluid flows through the second pathway relative to the first pathway, the separate fluid has desirably been pre-heated in order to be able to transfer heat to the fluid in the first flow pathway 1110 at the heat exchange region 1145.

As in the previous embodiments, the embodiment of FIG. 11 may be made up of multiple laminar units stacked atop one another to form layers of laminae. In addition, the embodiment of FIG. 11 may have the same or similar specifications as the other embodiments described herein, including materials, dimensions, residence times, and temperature levels.

Figure 12:
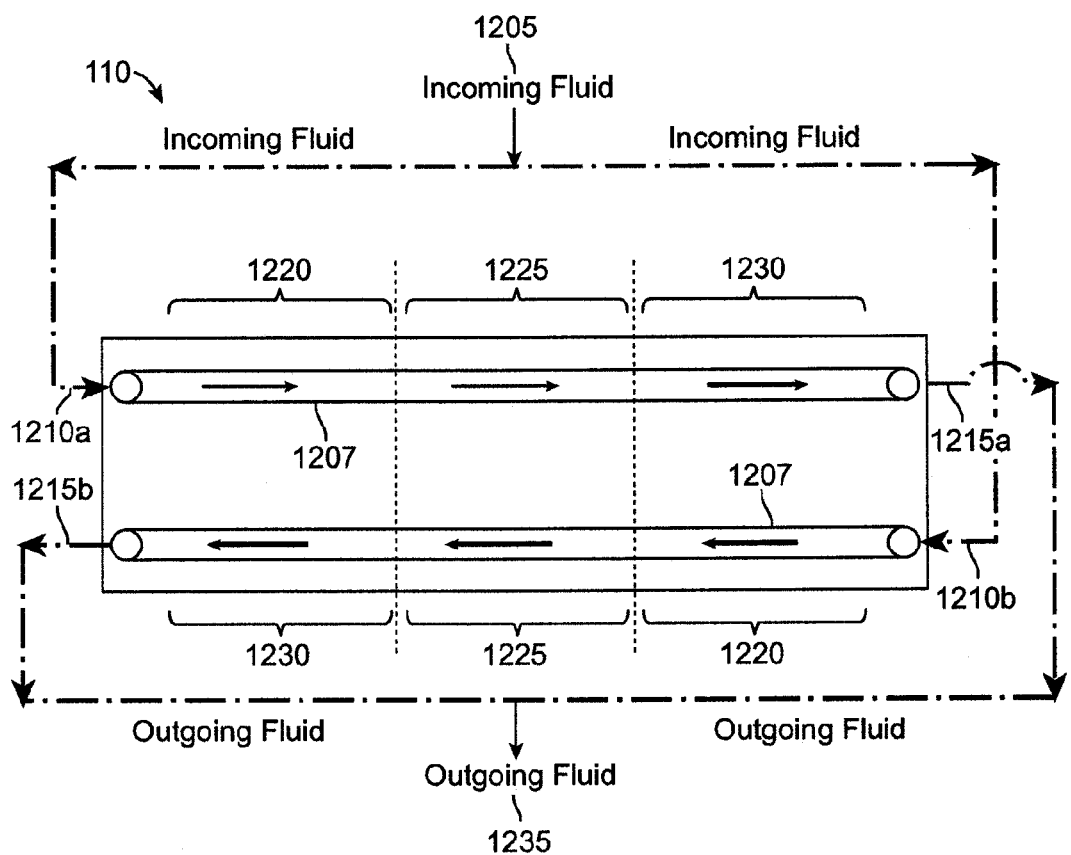
FIG. 12 shows a schematic, plan view of another exemplary embodiment of flow pathways for the microfluidic heat exchange system.

In another embodiment shown in FIG. 12, a microfluidic heat exchange system 110 purifies a single fluid. FIG. 12 represents an exemplary flow pathway configuration for a single lamina. A plurality of such laminae may be interleaved to form a stack of lamina as described above for other embodiments. The purification of the fluid may comprise pasteurizing the fluid although pasteurization is not necessary such as where the device is not used for dialysis. The heat exchange system receives a stream of incoming fluid 1205, which splits before entering the heat exchange system. A first portion of the stream of incoming fluid 1205*a* enters at a first inlet 1210A on one end of the system and a second portion of the stream of incoming fluid 1205 enters at a second inlet 1210*b* on the other, opposite end of the system. The two streams of incoming fluid 1205 are distributed across the stacked laminae in alternating fashion such that there is no direct contact between the two fluid streams.

Each stream of incoming fluid 1205 enters a flow pathway 1207 and flows along the flow pathway toward an outlet 1215*a*. One stream of fluid enters via the inlet 1210*a* and exits at an outlet 1215*a* positioned on the same end of the system as the inlet 1210*b*, while the other stream of fluid enters via the inlet 1210*b* and exits at an outlet 1215*b* on the same end of the system as the inlet 1210*a*. Each flow pathway 1207 includes a first heat exchange region 1220 where heat is exchanged through a transfer layer between the incoming fluid and the previously-heated outgoing fluid flowing through a lamina immediately above (or below) the instant lamina in the stack. As the fluid flows through the heat exchange region 1220 it receives heat via the heat transfer and is pre-heated prior to entering a heater region 1225.

For each flow pathway 1207, the fluid then flows into the heater region 1225, which thermally communicates with at least one heater, and preferably multiple heaters, for communicating heat into the flowing fluid. The fluid is heated under pressure to a temperature at or above the desired threshold pasteurization temperature as described above for other embodiments. The heater region 1225 also serves as a residence chamber. The fluid flows through the residence chamber while held at or above the desired temperature for the desired residence time. The desired residence time may be achieved, for example, by varying the flow rate and/or by employing a serpentine flow path of the required length within the heater region 1225. After leaving the heater region 1225, the outgoing fluid enters a second heat exchange region 1230 where the outgoing fluid exchanges heat with the incoming fluid flowing through a lamina immediately above (or below) the instant lamina in the stack. The outgoing fluid then exits the flow pathways through the outlets 1215A and 1215*b*. The two streams of outgoing fluid then recombine into a single stream of outgoing fluid 1235 before continuing on to the ultrafilter to remove all or substantially all of the dead bacteria killed by the pasteurization process.

Figure 13B:
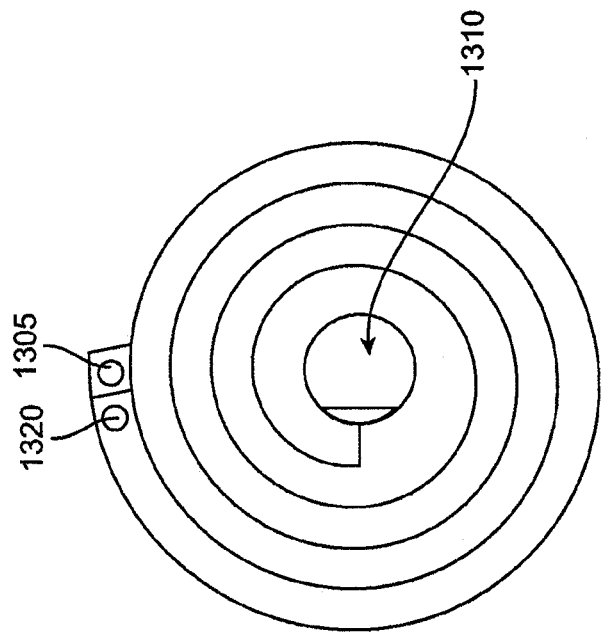
FIG. 13B shows another embodiment of an outlet lamina that forms an outlet pathway where fluid flows in an outward direction through the heat exchange system.
Figure 13A:
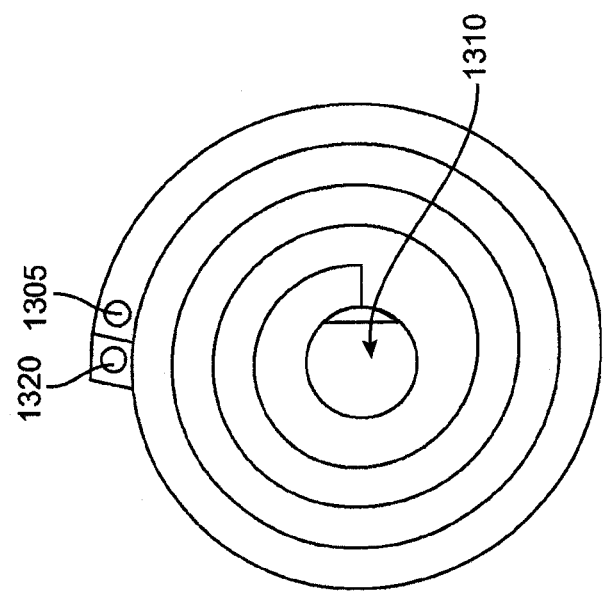
FIG. 13A shows another embodiment of an inlet lamina that forms an inlet pathway where fluid flows in an inward direction through the heat exchange system.

FIG. 13A shows another embodiment of an inlet lamina that forms a spiral inlet pathway where fluid flows in an inward direction through the heat exchange system. FIG. 13B shows a corresponding outlet lamina that forms a similar spiral pathway where fluid flow in an outward direction. A plurality of such inlet and outlet laminae may be interleaved to form a stack of lamina as described above for other embodiments. The laminae are shown having a circular outer contour although the outer shape may vary as with the other embodiments.

With reference to FIG. 13A, the inlet lamina has a header forming an inlet 1305 where incoming fluid enters the inlet pathway. The inlet pathway spirals inward toward a center of the pathway, where a heating chamber 1310 is located. The heating chamber 1310 also serves as a residence chamber for the fluid, as described below. One or more heaters are positioned in thermal communication with the heating chamber 1310 to provide heat to fluid flowing in the heating chamber 1310. The heating chamber 1310 extends across multiple laminae in the stack and includes a conduit that communicates with the outlet lamina shown in FIG. 13B. The fluid enters the outlet lamina from the heating chamber 1310. The outlet lamina has an outflow pathway that spirals outward from the heating chamber 1310 toward an outlet 1320.

In use, the fluid enters the inlet pathway of the inlet lamina through the inlet 1305 shown in FIG. 13B. The fluid then flows along the spiral inlet pathway toward the heater chamber 1310. As in the previous embodiments, the incoming fluid is at a temperature that is less than previously-heated fluid flowing through the outlet lamina, which is positioned immediately above or below the inlet lamina. As the fluid flows through the inlet pathway, the fluid receives heat from previously-heated fluid flowing through the outlet pathway of the outlet lamina. This serves to pre-heat the fluid prior to the fluid flowing into the heating chamber 1310. The fluid then flows into the heating chamber 1310 where the fluid receives heat from the one or more heaters.

While in the heating chamber 1310, the fluid is heated under pressure to a temperature at or above the desired threshold pasteurization temperature as described above for other embodiments. As mentioned, the heating chamber 1310 also serves as a residence chamber. The fluid flows through the residence chamber while held at or above the desired temperature for the desired residence time. As in other embodiments, the desired residence time may be achieved, for example, by varying the flow rate and/or by employing a serpentine flow path of the required length within the heater chamber 1310. After leaving the heater chamber, the outgoing fluid enters the outlet pathway of an outlet lamina such as shown in FIG. 13B. The outgoing fluid flows outward from the heating chamber 1310 along the spiral flow pathway toward the outlet 1320. The spiral pathway of the inlet lamina thermally communicates with the spiral pathway of the outlet lamina across a transfer layer As the outgoing fluid flows along the spiral pathway, it exchanges heat with the incoming fluid flowing through an inlet lamina immediately above (or below) the instant lamina in the stack. The outgoing fluid then exits the stack of lamina via the outlet 1320 before continuing on to the ultrafilter to remove all or substantially all of the dead bacteria killed by the pasteurization process.

3. Microfluidic Heat Exchange System: Control System

Figure 14:
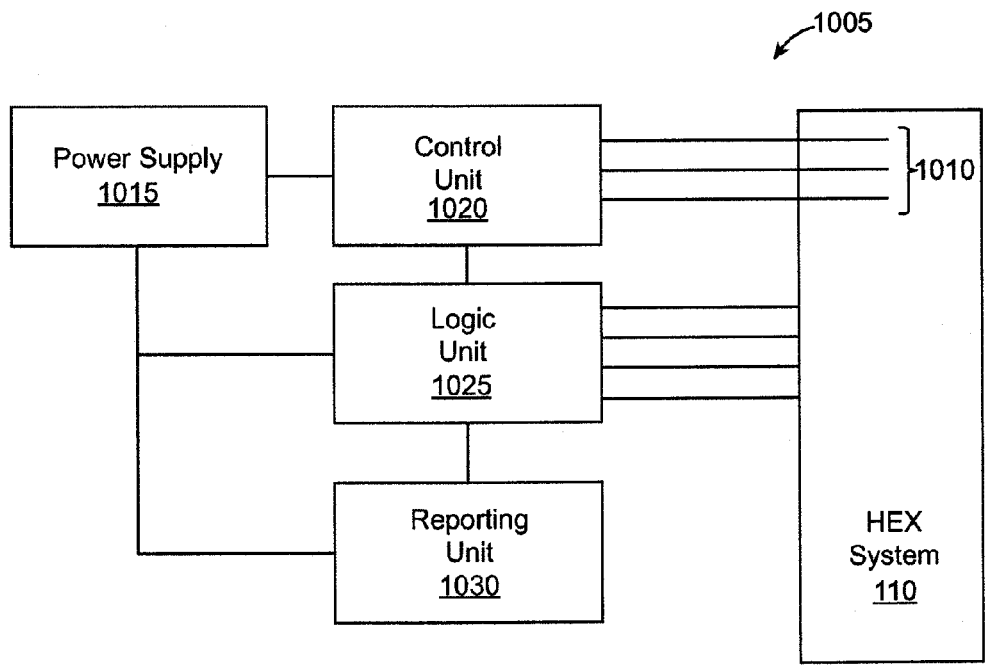
FIG. 14 shows a schematic view of an exemplary heater control system.

The microfluidic heat exchange system 110 may include or may be coupled to a control system adapted to regulate and/or control one or more aspects of the fluid flow through the system, such as fluid flow rate, temperature and/or pressure of the fluid, chemical concentration of the fluid, etc. FIG. 14 shows a schematic view of an exemplary heater control system 1005 communicatively coupled to the microfluidic heat exchange system 110. The heater control system 1005 includes at least one power supply 1015 communicatively coupled to a heater control unit 1020, which communicates with a control logic unit 1025. The heater control unit 1020 is adapted to control the power supply to the heaters, either on an individual basis or collectively to a group of heaters. This permits temporal and spatial control of heat supplied to the microfluidic heat exchange system 110.

The heater control system 1005 may include one or more temperature sensors 1010 positioned in or around the microfluidic heat exchange system 110 for sensing fluid temperature at one or more locations within the fluid flow path. The type of sensor can vary. In an embodiment, one or more thermocouples are used as the sensors 1010. The sensors 1010 communicate with the heater control unit 1020 and the control logic unit 1025 to provide a temperature feedback loop. The heater control system 1005 provides for feedback control of fluid temperature in the system to ensure, for example, that fluid is being heated to the required pasteurization temperature and/or that the fluid is not overheated or underheated. For example, the heater control unit 1020 in conjunction with the control logic unit 1025 may adjust power to one or more of the heaters based on a sensed temperature in order to achieve a desired temperature profile in one or more locations of the fluid flow path. The heater control system 1005 may include other types of sensors such as, for example, pressure sensors, flow rate sensors, etc. to monitor and adjust other parameters of the fluid as desired.

The heater control system 1005 may also be configured to provide one or more alarms, such as a visual and/or audio indication and/or a telecommunications signal, to the user or a remote monitor of system functions to inform such parties when the temperature is at an undesired level. For example, the control unit 1020 may comprise one or more temperature set limits within which to maintain, for example, the residence chamber temperature. If a limit is exceeded—i.e., if the temperature falls below the lower operating limit or above the upper operating limit, the control system may bypass the heater, set off an alarm and cease operation of the overall water purification system until the problem can be diagnosed and fixed by the operator. In this regard, the control system 1005 may include a reporting unit 1030 that includes a database. The reporting unit 1030 is configured to log and store data from the sensors and to communicate such data to a user or monitor of the system at a remote site.

4. Fluid Purification System: Startup and Shutdown

Where the fluid purification system is used for dialysis, it is important to avoid bacterial contamination of the fluid flow path, both within the heat exchanger system 110 and throughout the components downstream of the heat exchanger system 110. In this regard, the heat exchanger system 110, which serves as a pasteurizer, is desirably operated in a manner that ensures clean fluid flow upon startup of the fluid purification system and also avoids bacterial contamination of the downstream components, or at least mitigates the contamination effects, upon shut down (i.e., when the heaters 292 are de-powered).

In an embodiment, clean fluid flow upon startup is achieved by initially flowing a sterilizing liquid through the heat exchanger system 110 while the heaters 292 are being powered up. The sterilizing liquid then flows through all the components downstream of the heat exchanger system 110 until the heat exchanger system 110 attains a desired operating temperature. Upon the heat exchanger system 110 reaching the desired operating temperature, fluid flow to the heat exchanger system 110 switches to water from the reverse osmosis system 125. The water passes through the heat exchanger system 110 (which has achieved the desired operating temperature) to flush the sterilizing liquid out of the flow pathway of the heat exchanger system 110. Various sterilizing solutions may be used. The solution, for example, can be a 1% chlorine in water mixture, or some other widely recognized water additive that can kill bacteria.

The fluid purification system may be shut down as follows. The heaters 292 are de-powered while fluid flow through the heat exchanger system 110 is maintained. Alternatively, a sterilizing liquid may be flowed through the heat exchanger system 110 until the heat exchanger system 110 attains near room temperature conditions. In this manner, the flow pathway is maintained in a sterilized condition as the heat exchanger system 110 shuts down. The flow pathway of the heat exchanger system 110 is then closed or "locked down" with sterilizing liquid present in the flow pathway of the heat exchanger system 110. The presence of the sterilizing liquid greatly reduces the likelihood of bacterial contamination during shutdown.

In another embodiment, one or more valves are positioned in the flow pathway of fluid purification system wherein the valves allow a circulating flow of solution to loop through the pump 150, heat exchanger system 110, and downstream components in a recirculation loop until desired pasteurization conditions are achieved during startup. The valves are then set to allow the sterilizing liquid to be flushed from the system. An auxiliary component, such as a microchannel fluid heater (without heat exchange capability), can also be incorporated to provide the ability to circulated a warmed (e.g., less than 100 degrees Celsius) sterilizing liquid through the downstream components and/or through the unpowered heat exchanger system 110. The sterilizing liquid can be used during either a start-up or shut-down process for keeping the flow pathway and components clean over the span of weeks and/or months. The use of a recirculation loop for sterilizing liquid at start up is another manner to prevent bacteria from entering the fluid purification system before the heat exchanger system 110 achieves operating temperatures. A timing control logic may be used with a temperature sensing capability to implement a process that ensures quality control over the start-up and shut down processes. The control logic may be configured to initiate flow only after the heat exchanger system 110 or a heater attains a preset temperature.

The flow path may include one or more bypass circulation routes that permit circulation of cleaning and/or sterilization fluid through the flow path. The circulation route may be an open flow loop wherein fluid flowing through the circulation route is dischargeable from the system after use. In another embodiment, the circulation route may be a closed flow loop wherein fluid flowing the circulation route not dischargeable from the system. Alternately, the system may include both open and closed circulation routes.

5. Dialysate Preparation System

Figure 15:
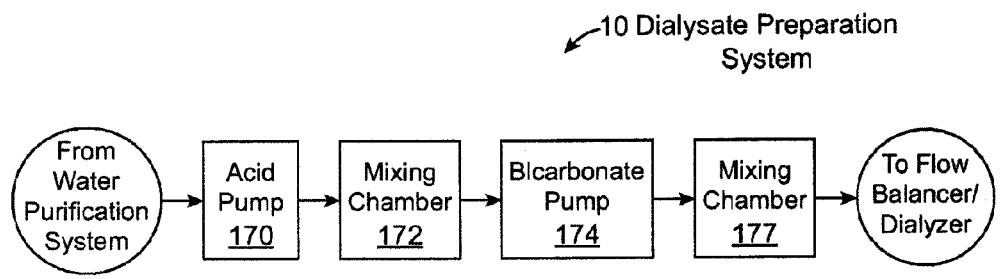
FIG. 15 shows a high level, schematic view of a dialysate preparation system of the dialysis system.

The water is in a pasteurized state as it exits the water purification system 5 and flows into the dialysate preparation system 10. The dialysate preparation system 10 is configured to mix the pasteurized water with a supply of concentrate solutions in order to make dialysate. FIG. 15 shows a high level, schematic view of the dialysate preparation system 5. The embodiment of FIG. 15 is exemplary and it should be appreciated that variations are within the scope of this disclosure.

The dialysate preparation system 10 includes an acid pump 170 that fluidly communicates with a supply of concentrated acidified dialysate concentrate for mixing with the purified water. The water flows from the water purification system 5 to the acid pump 170, which pumps the acid concentrate into the water. The water (mixed with acid) then flows into a first mixing chamber 172, which is configured to mix the water with the acid such as by causing turbulent flow. From the first mixing chamber 172, the acid-water mixture flows toward a bicarbonate pump 174. A sensor, such as a conductivity sensor CS, may be positioned downstream of the first mixing chamber 172. The conductivity sensor CS is configured to detect a level of electrolytes in the mixture. The conductivity sensor CS may be in a closed loop communication with the acid pump 170 and a control system that may regulate the speed of the acid pump to achieve a desired level of acid pumping into the water.

The bicarbonate pump 174 pumps bicarbonate concentrate into the acid-water mixture at a level sufficient to form dialysate. The resulting mixture of fluid flows into a second mixing chamber 177 and exits the second mixing chamber 177 as dialysate. Another sensor, such as a conductivity sensor CS, may be positioned downstream of the second mixing chamber 172. The second conductivity sensor CS may be in a closed loop communication with the bicarbonate pump 177. The dialysate then flows toward the flow balancer system and the dialyzer.

6. Dialyzer

Figure 16:
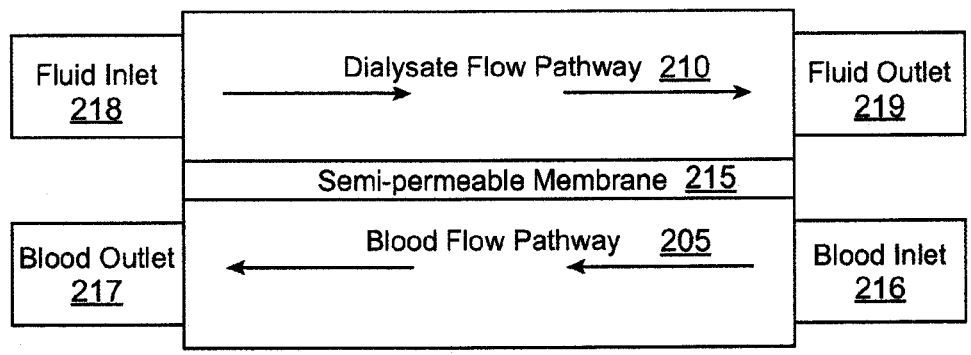
FIG. 16 is a schematic, cross-sectional view of a dialyzer of the dialysis system.

FIG. 16 is a schematic, cross-sectional view of the dialyzer 15, which defines a blood compartment having a blood flow pathway 205 and a dialysate compartment having a dialysate flow pathway 210 separated by a transfer layer comprised of a semi-permeable membrane 215. In an embodiment, the dialyzer includes one or more microfluidic pathways such as micro flow fields and/or microchannels. Exemplary embodiments of dialyzers that utilize micro flow fields and/or microchannels are described below. Exemplary embodiments of dialyzers comprised of flow field dialyzers are described below. However, the dialysis system described herein can be used with any of a variety of dialyzers including a variety of commercially-available dialyzers.

The blood (from a patient) enters the blood flow pathway 205 via a blood inlet 216, flows through the blood flow pathway 205, and exits via a blood outlet 217. The dialysate enters the dialysate flow pathway 210 via a fluid inlet 218, flows through the dialysate flow pathway 210, and exits via a fluid outlet 219. The semi-permeable membrane 215 is configured to allow the transfer of one or more substances from the blood in the blood flow pathway 205 to the dialysate in the dialysate flow pathway 210, or visa-versa.

Some examples of materials that may be used as the semi-permeable membrane 215 include polymers, copolymers, metals, ceramics, composites, and/or liquid membranes. One example of a composite membrane is polysulfone-nanocrystalline cellulose composite membrane such as AN69 flat sheet membranes available from Gambro Medical. Gas-liquid contactor membranes may also be employed for transferring a substance between a liquid and gas such as for oxygenation of blood, whereby the membrane allows transfer of carbon dioxide and oxygen, such that oxygen transfers to blood from oxygen or oxygen-enriched air, and carbon dioxide transfers from the blood to the gas. Fluid membranes may also be employed. Fluid membranes comprise a lamina having through cut microchannels containing fluid and a first and second membrane support positioned to contain fluid in the microchannels.

When flowing through the dialyzer 15, the blood and the dialysate may flow in a counter-flow configuration wherein blood flows through the blood flow pathway 205 in one direction and the dialysate flows through the dialysate flow pathway 210 in the opposite direction. The dialyzer 15 is described in the context of having a counter-flow configuration although a cross-flow configuration may also be used. As the blood and water flow along the membrane 215, hemodialysis occurs. The dialyzer 15 is also configured to perform ultrafiltration wherein a pressure differential across the membrane 215 results in fluid and dissolved solutes passing across the membrane 215 from the blood to the dialysate.

The dialyzer 15 is also configured to perform hemodiafiltration wherein solute movement across the semipermeable membrane 215 is governed by convection rather than by diffusion. A positive hydrostatic pressure differential between the blood flow pathway 205 and the dialysate flow pathway 210 drives water and solutes across the semipermeable membrane 215 from the blood flow pathway to the fluid flow pathway. Solutes of both small and large molecules get dragged through the semipermeable membrane 215 along with the fluid. In a typical hemodiafiltration procedure, the direction of water and solute movement is oscillated between moving water and solutes from the blood into the dialysate and moving water and solutes from the dialysate into the blood. Over a predetermined span of time, there is a net zero loss and zero net gain of fluid from the blood into the dialysate. However, during discrete time periods within that span of time, there can be a net loss of fluid from the blood into the dialysate and a net gain of fluid into the blood from the dialysate.

The dialyzer 15 may utilize microfluidic flow fields or microfluidic channels. Exemplary embodiments of microfluidic systems for use as dialyzers are described below.

7. Flow Balancer System

The flow balancer system 20 is adapted to regulate the flow of dialysate into and out of the dialyzer 15 to achieve various types of dialysis, including hemodialysis, ultrafiltration, and hemodiafiltration. The flow balancer system 20 includes a first pump for pumping dialysate into a dialyzer and a second pump for pumping dialysate out of the dialyzer. The system also includes a third pump that provides improved control of a level of ultrafiltration, hemodiafiltration, or both, as described in detail below.

Figure 17:
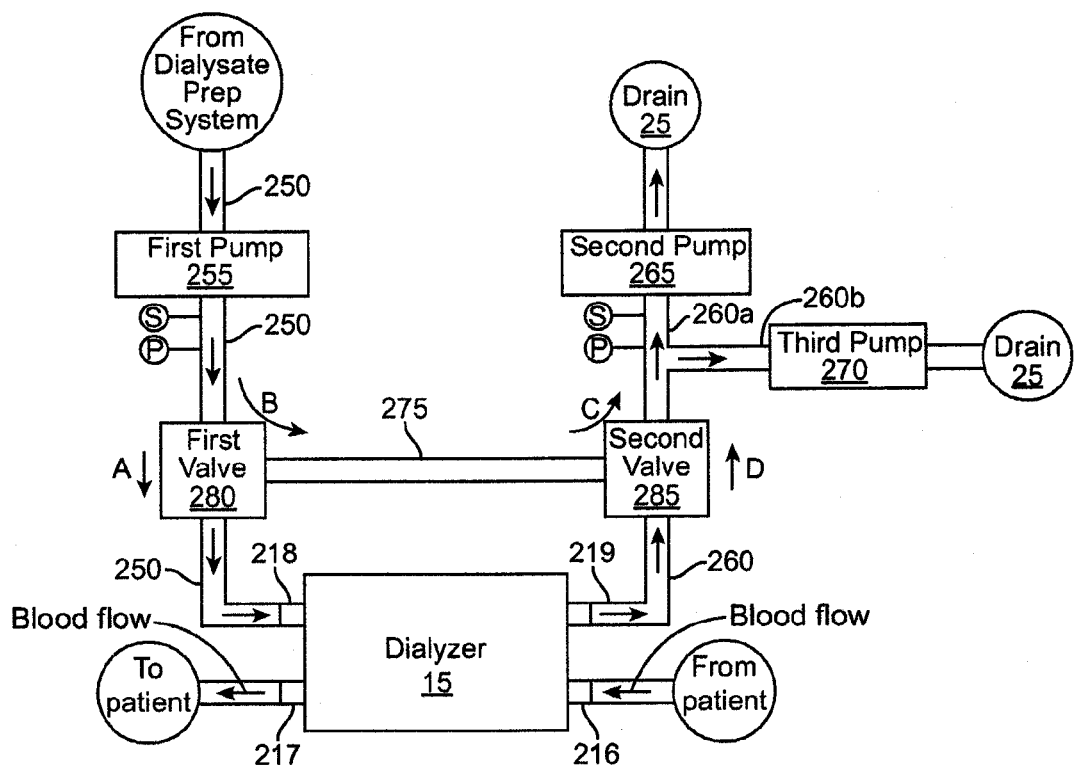
FIG. 17 shows a schematic view of a flow balance system.

FIG. 17 shows a schematic view of the flow balancer system 20 including the dialyzer 15. The system includes an arrangement of three or more pumps that provide improved control over the type of hemodialysis being performed. By varying the relative pump speeds of the three pumps, an operator can vary the level of blood filtration and can also selectively achieve ultrafiltration and hemodiafiltration of the blood.

The flow balancer system 20 includes plumbing that forms a plurality of fluid flow pathways, which may be any type of conduit through which a fluid such as dialysate may flow. The fluid flow pathways include an inlet pathway 250 through which a fluid such as unused dialysate flows from the dialysate preparation system 10 toward and into the dialyzer 15. At least a first pump 255 is positioned along or in communication with the inlet pathway 250 for pumping the fluid toward the dialyzer 15 at a desired flow rate. One or more sensors S may be coupled to the fluid flow pathway for sensing one or more characteristics of the incoming fluid, such as pressure, flow rate, temperature, conductivity, etc. In addition, one or more sample ports P may be coupled to the fluid flow pathways that provide access to fluid flowing through the piping. FIG. 17 shows the sensors S and sample ports P coupled to the fluid flow pathways at specific locations, although the quantity and locations of the sensors S and sample ports P may vary.

The fluid flow pathways further include an outlet pathway 260 through which used dialysate flows out of the dialyzer 15 toward one or more drains 25. In some embodiments, the dialysate exiting the dialyzer may be used to pre-heat other incoming fluids in the system, such as the water stream entering the heat exchange and purification system, before reaching the drain 25. The outlet pathway 260 bifurcates into two or more outlet pathways including a main outlet pathway 260a and a secondary outlet pathway 260b. At least a second pump 265 is positioned along or in communication with the main outlet pathway 260a for pumping the dialysate out of and away from the dialyzer 15 through the main outlet pathway 260a.

A third pump 270 is positioned along or in communication with the secondary outlet pathway second valve 285. The third pump 270 can be used to augment fluid flow through the fluid flow pathways such as to selectively achieve differentials in flow rates between the inlet pathway 250 and the outlet pathway 260 pursuant to achieving various types of dialysis, including hemodialysis, ultrafiltration, and hemodiafiltration, as described more fully below. The third pump pumps dialysate through the fluid flow pathways when the system is in dialysis mode. The third pump may also pump another fluid, such as water or disinfectant, when the system is in a different mode, such as in a calibration mode or in a cleaning mode. The third pump 270 can also be used to calibrate flow rates between the first pump 255 and the second pump 265, as described more fully below.

Figure 18:
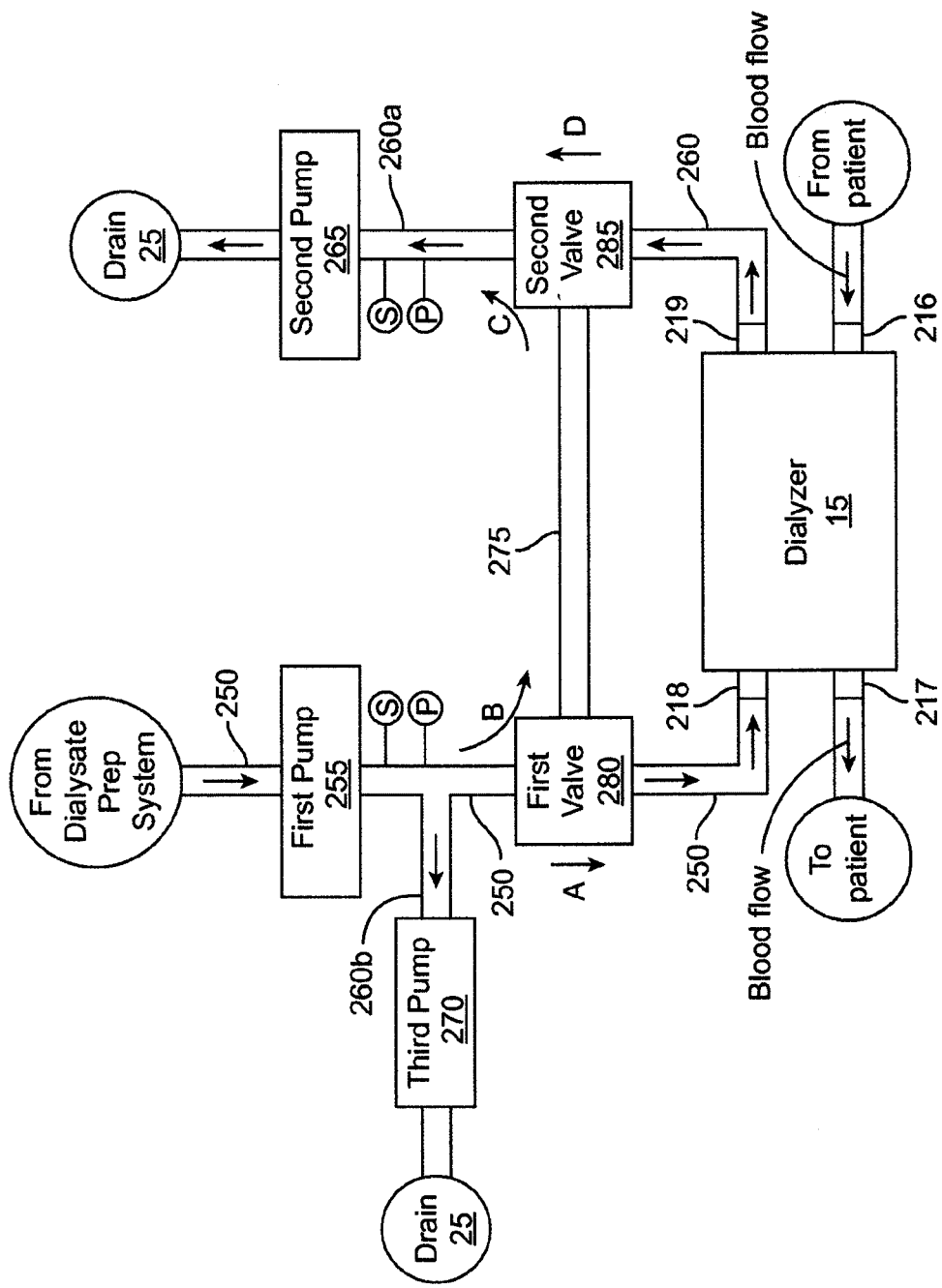
FIG. 18 shows a schematic view of another embodiment of a flow balance system.

In another embodiment, shown in FIG. 18, the third pump 270 is positioned along the inlet pathway 250 upstream of the inlet 218 of the dialyzer 15. In this embodiment, the secondary outlet pathway 260 branches off the inlet pathway 250 at a location downstream of the first pump 255 and upstream of the first valve 280. The third pump 270 pumps fluid toward the drain 25. The embodiment of FIG. 17 may be more efficient than the embodiment of FIG. 18 because the third pump 270 in FIG. 18 pumps fresh, unused dialysate into the drain 140 while the third pump in FIG. 17 pumps used dialysate into the drain 25. In another embodiment, the third pump 270 and the second pump 265 are both positioned along a single, non-bifurcating outflow pathway.

Various types of pumps may be used for the first, second and third pumps. In an embodiment, the pumps are nutating pumps. On other embodiments, the pumps could be rotary lobe pumps, progressing cavity pumps, rotary gear pumps, piston pumps, diaphragm pumps, screw pumps, gear pumps, hydraulic pumps, vane pumps, regenerative (peripheral) pumps, or peristaltic pumps, or any combination thereof. Other types of pumps can also be used. The first pump 255 and the second pump 265 may be driven by a common shaft to ensure synchrony of the pump strokes and the volume of fluid pumped. It is understood that first pump 255 and the second pump 265 may also be fully independent from each other.

As mentioned, any of a variety of fluid conduits may be used to form the fluid flow pathways of the flow balancer system 20. In an embodiment, at least a portion of the fluid flow pathway is formed of piping having an inside diameter from ⅛ inch to ½ inch. The flow rate in the piping could range between about 50 ml/min to about 1,000 ml/min. In an embodiment, the flow rate is in the range of between about 100 ml/min and about 300 ml/min.

With reference again to FIG. 18, the fluid flow pathways further include a bypass pathway 275 that fluidly directly connects the inlet pathway 250 and the outlet pathway 260. An exemplary purpose of the bypass pathway 275 is to provide a fluid flow pathway where fluid can flow into and out of the dialysis system and bypass the dialyzer 15, such as for flushing, cleaning or calibrating the system. In an embodiment, the junction between the inlet pathway 250 and bypass pathway 275 is located upstream of the fluid inlet 120 of the dialyzer 15, and the junction between the bypass pathway 275 and the outlet pathway is located downstream of the fluid outlet 125 of the dialyzer 15. However, other configurations of the bypass pathway 275 can be used to achieve bypassing of the dialyzer 15.

A first valve 280 is positioned at the junction between the inlet pathway 250 and the bypass pathway 275. A second valve 285 is positioned at the junction between the bypass pathway 275 and the outlet pathway 260. The first valve 280 and second valve 285 are three-way valves, such as solenoid valves, that can be used to selectively regulate fluid flow through the fluid flow pathways. That is, the first valve 280 can be set to either of two or more settings including (1) a dialysis setting wherein the first valve directs all incoming fluid along the inlet pathway 250 toward the dialyzer 15 (as represented by arrow A in FIG. 17) and prevents incoming fluid from flowing into the bypass pathway 275; or (2) a bypass setting wherein the first valve 280 diverts all the incoming fluid into the bypass pathway 275 (as represented by arrow B in FIG. 17) and the prevents incoming fluid from flowing past the first valve toward the dialyzer 15.

The second valve 285 can also be set to either of two settings including (1) a bypass setting wherein the second valve 285 directs incoming fluid from the bypass pathway 275 into the outlet pathway 260 (as represented by arrow C in FIG. 17); or (2) a dialysis setting wherein the second valve 285 closes flow from the bypass pathway 275 such that outgoing fluid from the dialyzer outlet 125 continues to flow outward along the outlet pathway 260 (as represented by arrow D in FIG. 17.) The first valve 280 and the second valve 285 are generally both set in tandem to either the bypass setting or the dialysis setting. The system may include a control and safety system that ensures that the first and second valves are not set to incompatible settings.

The arrangement of the various components of the dialysis system shown in FIGS. 17 and 18 are exemplary and other arrangements are possible. For example, the flow pathways and the pumps may be placed in different locations along the flow pathways from what is shown in FIGS. 17 and 18. In an embodiment, the third pump 270 is positioned in the flow pathway at a location upstream of the dialyzer 15 and downstream of the first valve 280 or the third pump can be positioned downstream of the dialyzer 15 and upstream of the second valve 285. Moreover, the system can employ more than three pumps.

8. Flow Balancer System: Operation of Pumps to Achieve Hemodialysis without Ultrafiltration With reference again to FIG. 17, the flow balancer system 20 achieves hemodialysis without ultrafiltration when the flow rate through the inlet pathway 250 is equal to or substantially equal to the flow rate through the outlet pathway 260. In other words, hemodialysis without ultrafiltration is achieved where the amount of dialysate flowing into dialyzer 15 via the inlet pathway 250 is substantially equal to the amount of dialysate flowing out of the dialyzer via the outlet pathway 260 over a period time. This can be achieved by operating the first pump 255 at a first pump rate to provide a first flow rate through the inlet pathway 250 and operating the second pump 265 and the third pump 270 at respective pump rates that collectively achieve a flow rate through the outlet pathway 260 that is equal to the flow rate through the inlet pathway 250.

In an embodiment, the system performs a hemodialysis procedure utilizing all three pumps in an active state substantially continuously throughout the hemodialysis procedure. The system adjusts the pump rate of the third pump 270 to achieve a desired balance of equal flow rates between the inlet pathway 250 and the outlet pathway 260. In this embodiment, the first pump 255, second pump 265, and third pump 270 are all active throughout the hemodialysis procedure with the first and second pumps operating at different pump rates and the third pump operating at a pump rate that achieves a balanced flow rate between the inlet pathway 250 and the outlet pathway 136. The third pump is typically operated at a pump rate that is equal to the differential between the pump rate of the first pump and the pump rate of the second pump. In this manner, the second and third pumps collectively achieve a flow rate through the outlet pathway 260 that is equal to the flow rate through the inlet pathway 250.

For example, to achieve a desired flow rate of, for example, 100 ml/min through the dialyzer, the first pump 255 is set to provide a flow rate of 100 ml/min through the inlet pathway 250 and the second pump 265 is deliberately set out of balance with the first pump 255, to provide, for example, a flow rate of only 80 ml/min. This would provide a flow rate differential of 20 ml/min between the first pump and the second pump. The pump rate of third pump 270 is set to provide a flow rate of 20 ml/min, which is equal to the differential between the flow rates of the first and second pumps. In this manner, the second pump 265 and the third pump 270 collectively achieve a flow rate of 100 ml/min through the outlet pathway 260 which is equal to the flow rate of through the inlet pathway 250 such that the flow rates are balanced across the dialyzer. Under such conditions, waste solutes move across the dialyzer's semipermeable membrane from the blood stream into the dialysate via diffusion to perform hemodialysis.

The flow rates through the inlet pathway 250 and the outlet pathway 260 may be measured using one or more of the sensors S. In an embodiment, the sensors are flow rate sensors that directly measure flow rates through the inlet pathway 250 and outlet pathway 260. In another embodiment, the sensors are pressure sensors that provide indications as to the fluid pressure within the inlet pathway 250 and the fluid pressure within the outlet pathway 260. Fluid pressure is a function of the flow rate through the flow pathways and therefore provides an indirect measurement of flow rate. Where the fluid pressure in the inlet pathway 250 is equal to the fluid pressure in the outlet pathway 260, this is an indication that the flow rates are balanced between the inlet pathway and outlet pathway. Where the fluid pressure in the inlet pathway 250 is less than the fluid pressure through the outlet pathway 260, this is an indication that the flow rate through the inlet pathway 250 is less than the flow rate through the outlet pathway 260. Where the fluid pressure in the inlet pathway 250 is greater than the fluid pressure through the outlet pathway 260, this is an indication that the flow rate through the inlet pathway 250 is greater than the flow rate through the outlet pathway 260. The system of fluid pathways may include one or more damping mechanisms for dampening any extreme fluctuations in pressure within the fluid pathways.

Figure 19:
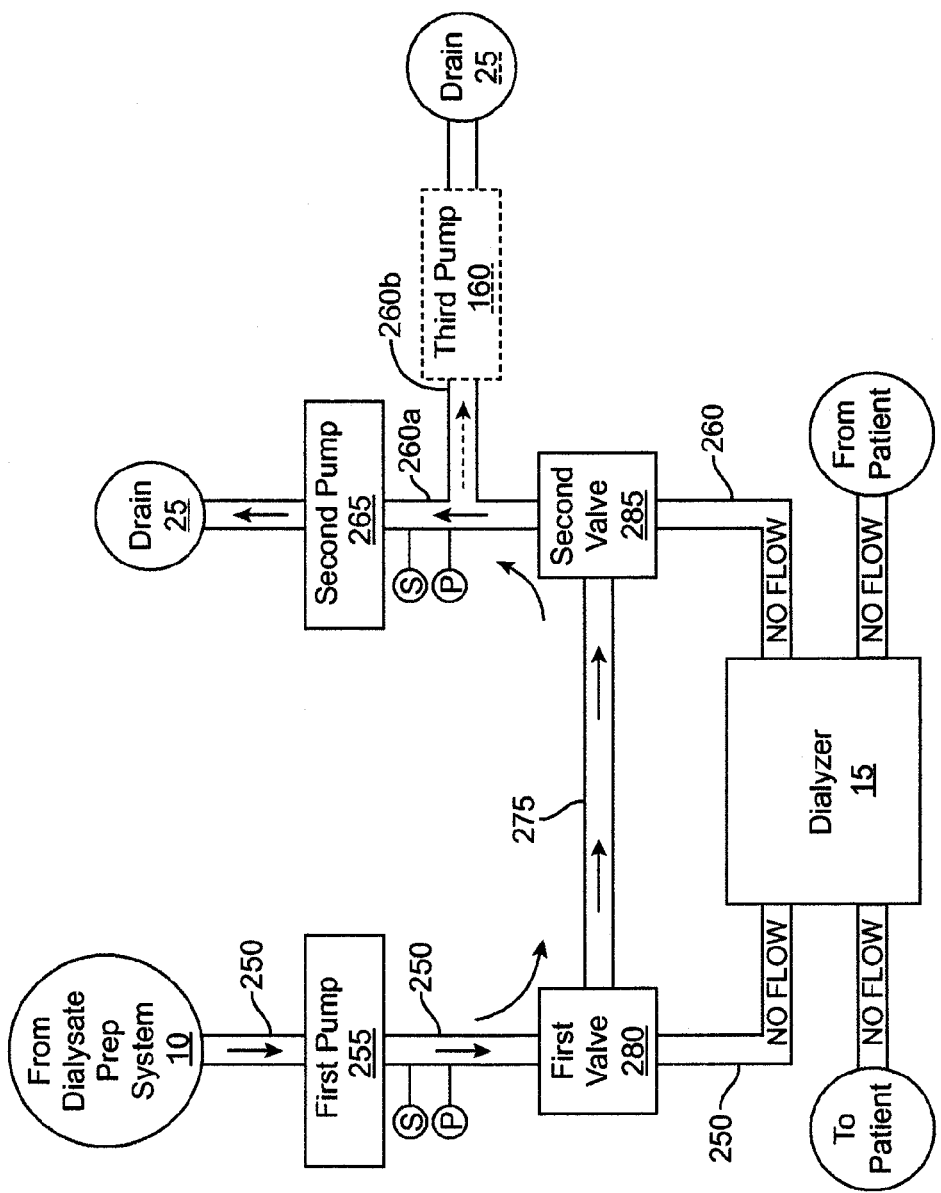
FIG. 19 shows a schematic representation of the flow balance system running in a calibration mode.

In the latter two situations, the pump rate of the third pump 270 may be adjusted in response to a pressure differential between the inlet and outlet pathways such as in a calibration procedure, to achieve a balanced flow rate between the inlet pathway 250 and outlet pathway 260. The calibration procedure may optionally be performed with the system in a calibration mode such that the first and second valves are set to cause fluid to flow through the bypass pathway 275 and bypass the dialyzer 15, as represented in FIG. 19 and described in more detail below. When the calibration procedure is performed by bypassing the dialyzer 15 and a pressure differential is detected between the inlet and outlet pathways, the flow of the third pump 270 may be appropriately adjusted 'on the fly' to increase or decrease the third pump's speed to achieve the desired flow rate in the outlet pathway 260 without having to turn the pump on or off. In this regard, the pressure sensors S and the three pumps, as well as the valves 280 and 285, may be connected in a closed loop control system to achieve automatic balancing of the flow rates.

In another embodiment, a balanced flow rate between the inlet pathway 250 and the outlet pathway 260 is achieved in theory at least by the first pump 255 and the second pump 265 operating at the same pump rate to achieve equal flow rates through the inlet pathway 250 and outlet pathway 260. Although it is theoretically possible to match the flow rates of the first pump 255 and the second pump 265, various factors may result in the actual fluid flow rate in the inlet pathway 250 differing from the actual fluid flow rate in the outlet pathway 260. The factors may include trapped air, hardware wear, and fluid leakage, which can cause the flow rates of the first and second pumps to diverge over time from a preset or desired value. Typical technologies in dialysis systems are unable to correct the flow balance for these types of factors.

Thus, there may come a time when a balanced flow rate cannot easily be achieved through use of the first and second pumps alone, and thus when there exists a need for correction to equalize the flow rates between the inlet pathway 250 and outlet pathway 260. Where the fluid flow rates are different, the third pump 270 can be used to correct the differing flow rates by being activated to pump fluid through the secondary outlet pathway 260b at a rate that is equal to the delta between the fluid flow rate through the inlet pathway 250 and the fluid flow rate through the outlet pathway 260. The system is preferably configured such that the first pump 255 is prevented from pumping less fluid than the second pump 265 such that the first pump 255 always pumps at a higher rate than the second pump 265. The system preferably includes a control system that detects a condition where the first pump 255 inadvertently pumps at a slower rate than the second pump 265 and sets off an alarm or moves the system out of dialysis mode if such a situation occurs.

According to a flow rate correction process, the sensors S (FIG. 17) are used to measure the flow rates through the inlet pathway 250 and the outlet pathway 260. A comparison is performed between the flow rate through the inlet pathway 250 and the flow rate through the outlet pathway 260. Where the flow rates are different, the third pump 270 is activated from a de-activated state to cause fluid to flow into the secondary outlet pathway second valve 285 at a rate selected to cause the overall flow rate in the outlet pathway 260 to be equal to the flow rate in the inlet pathway 250. A mechanism such as a servo mechanism may be used to adjust the stroke volume of the first pump 255 and/or the second pump 265 until balance of the flow rates is restored (as may be evidenced, for example, by the presence of the same fluid pressure in both the inlet pathway 250 and the outlet pathway 260).

As mentioned, the sensors S may be communicatively coupled to a control system and to the three pumps in a closed loop system. The control system includes hardware and/or software that automatically activates and/or deactivates the third pump 270 or adjusts the pump rate of the third pump 270 as needed in response to differences in detected flow rates from predetermined values or from each other, to equalize the flow rates between the inlet pathway 250 and outlet pathway 260. It should be appreciated that other measurements, such as fluid pressure in the inlet and outlet pathways, may be used to indirectly calculate the flow rates rather than directly measuring the flow rates. In this regard, the fluid pressures within the inlet pathway and the outlet pathway may be measured for any detectable change in pressure from a predetermined value or from each other. The flow pathways may be adapted to be essentially non-compliant so that a small difference in the flow rates of the first pump 255 and the second pump 265 will cause a rapid pressure change either negative or positive in magnitude.

The system may initially and/or periodically run in a calibration mode (sometimes also referred to as a UF checking mode) wherein a fluid (which may or may not be dialysate) is flowed through the flow pathways with the first valve 280 and second valve 285 set to the "bypass setting" such that fluid flowing through the system bypasses the dialyzer 15 via the bypass pathway 275. FIG. 19 shows a schematic representation of the system running in such a calibration mode where the dialyzer 15 is bypassed. In the embodiment where the system utilizes all three pumps in an active state substantially continuously throughout the hemodialysis procedure, the first and second pumps are initially deliberately set to achieve unbalanced flow rates. The sensors S in the flow pathway are then used to measure the fluid flow rate or pressure through the inlet pathway and the fluid flow rate or pressure through the outlet pathway. The third pump 270 is then set at a pump speed that achieves a substantially balanced flow rate between the inlet pathway 250 and outlet pathway 260.

Figure 20:
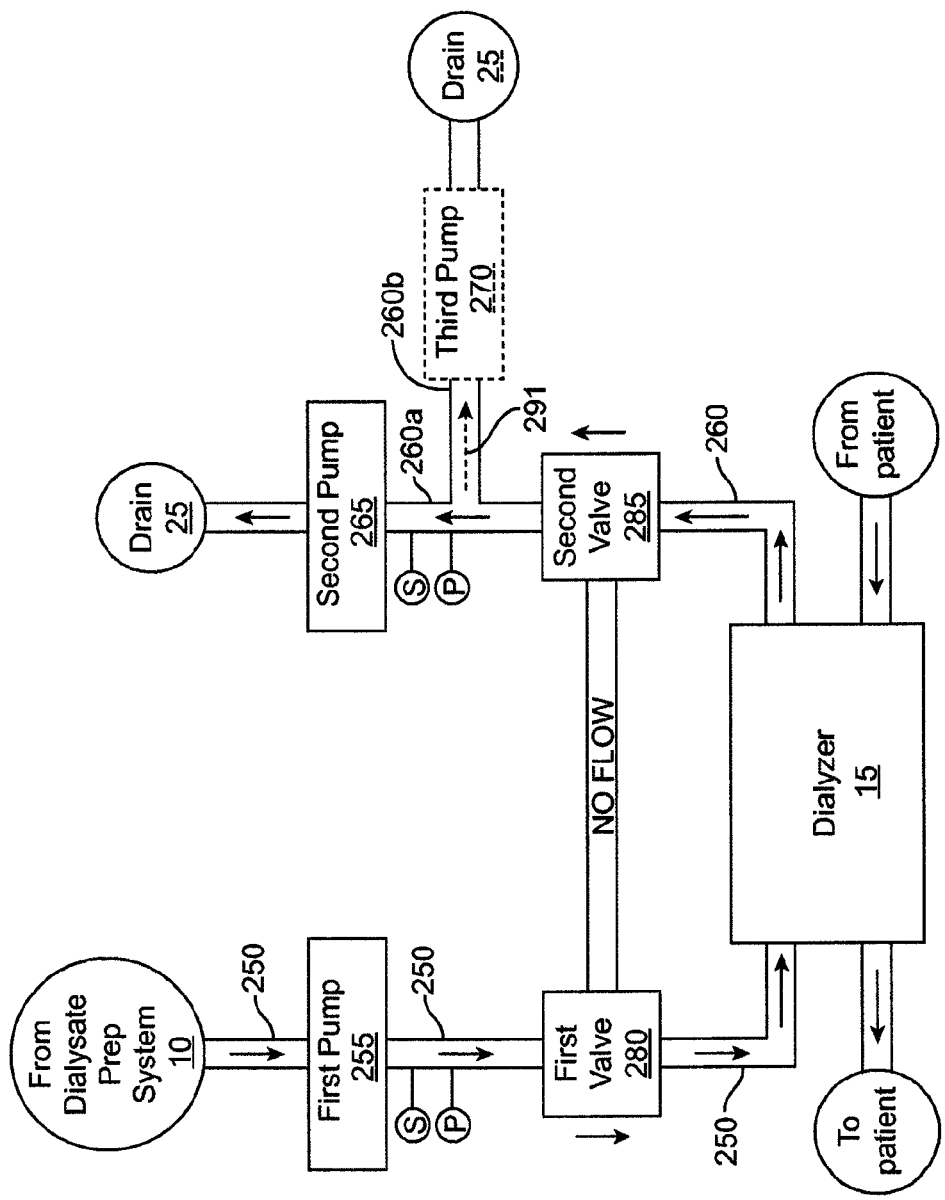
FIG. 20 shows a schematic representation of the flow balances system running in a dialysis mode.

In the other embodiment, the first pump 255 and second pump 265 are initially set to achieve equal flow rates without necessarily requiring the assistance of the third pump 270, which is initially inactive. The sensors S in the flow pathway are then used to measure the fluid flow rate through the inlet pathway and the fluid flow rate through the outlet pathway. Where the fluid flow rates are equal, the third pump 270 remains inactive. However, where the fluid flow rates are not equal, the third pump 270 is run at a rate that compensates for the discrepancy in flow rates between the inlet pathway 250 and outlet pathway 260. As mentioned, the third pump 270 may operate in a closed-loop relationship with the flow rate sensors and/or the pressure sensors. FIG. 20 shows the third pump 270 in phantom lines to represent the third pump may or may not be activated depending on whether there is a flow rate differential between the inlet pathway 250 and outlet pathway 260. The calibration procedure that does not require activating and de-activating the third pump is preferred as the system may run more efficiently when all three pumps are continuously operating.

After the calibration procedure is completed, the valves 280 and 285 may be set to the "dialysis setting" such that fluid flows from the source 110, through the inlet pathway 250, into the dialyzer 15, out of the dialyzer, and into the outlet pathway 260 from the dialyzer 15. When configured as such, the system can be used for dialysis by flowing dialysate into and out of the dialyzer 15 via the inlet and outlet pathways, and by also by flowing blood into and out of the dialyzer. During dialysis, the previously described calibration procedure may be periodically repeated, such as at predetermined intervals, to ensure that the flow rates of the inlet and outlet pathways remain within desired ranges.

In an embodiment, calibration is run only at the beginning of a dialysis session. In a more preferred embodiment, calibration is run periodically during the dialysis session, to ensure that the desired flow balance is maintained throughout the session. The control system can cycle the valves 280 and 285 controlling incoming flow stream between the dialysis setting and the bypass setting and run the calibration steps without additional interruptions to the dialysis session. During the calibration process, when the dialysate fluid bypasses the dialyzer 15, dialysis of the blood that passes through the dialyzer during that period of time is unhampered due to no fresh dialysate being provided to the dialyzer 15, though the blood may cool slightly. As long as the calibration step can be conducted over a relatively short period of time relative to the time between calibrations, the calibration has no material effect on the quality of dialysis being provided to the patient. In an embodiment, the dialysis system can be cycled between calibration for one minute followed by 60 minutes of dialysate being delivered through the dialyzer. In another embodiment, the dialysis system can be cycled between calibration for 30 seconds followed by 120 minutes of dialysate being delivered through the dialyzer.

FIG. 20 schematically shows the system running in a dialysis mode. The third pump 270 and the flow arrow 291 through the secondary outlet pathway second valve 285 are shown in phantom lines to indicate that the third pump 270 may or may not be active while the system is in dialysis mode. The third pump 270 may be active in the situation where the third pump 270 is needed to equalize the flow rates between the inlet pathway and outlet pathways. Or, the flow rates of the inlet and outlet pathways may be equal without the assistance of the third pump 270, in which case the third pump 270 remains inactive.

9. Flow Balancer System: Operation of Pumps to Achieve Ultrafiltration

The dialysis system achieves ultrafiltration in the situation where the flow rate through the inlet pathway 250 differs from the flow rate through the outlet pathway 260 such that there is an unbalanced flow rate across the dialyzer. Where the flow rate through the outlet pathway 260 is greater than the flow rate through the inlet pathway 250, the dialyzer 15 pulls fluid from the blood across the semipermeable membrane by a convective process in order to compensate for the unbalanced flow rate. In an embodiment, the system utilizes all three pumps substantially continuously throughout the procedure and the pump rate of the third pump 270 is adjusted to achieve a desired flow rate differential between the inlet pathway 250 and the outlet pathway 260 to perform ultrafiltration. That is, the first pump 255, second pump 265, and third pump 270 are all active with the first and second pumps operating at different pump rates. The third pump is then operated at a pump rate that intentionally achieves a desired imbalance of flow rates between the inlet pathway 250 and the outlet pathway 136 sufficient to cause ultrafiltration.

For example, to achieve the removal of fluid at a rate 10 ml/min from the blood stream, the first pump 255 is set to provide a flow rate of 100 ml/min through the inlet pathway 250 and the second pump 265 is deliberately set out of balance with the first pump 255, to provide, for example, a flow rate of only 80 ml/min. The third pump 270 is then set to provide a flow rate of 30 ml/min such that the second and third pumps collectively provide a flow rate of 110 ml/min through the outlet pathway 260. With a flow rate of 100 ml/min through the inlet pathway 250 and a flow rate of 110 ml/min through the outlet pathway, the dialyzer 15 compensates for the 10 ml/min flow rate differential by transferring 10 ml/min of fluid from the blood stream into the dialysate.

In another example, to achieve the addition of fluid at a flow rate of 10 ml/min into the blood stream, the first pump 255 is set to provide a flow rate of 100 ml/min through the inlet pathway 250 and the second pump 265 is again deliberately set out of balance with the first pump 255, to provide, for example, a flow rate of only 80 ml/min. The third pump 270 is then set to provide a flow rate of only 10 ml/min such that the second and third pumps collectively provide a flow rate of 90 ml/min through the outlet pathway 260. With a flow rate of 100 ml/min through the inlet pathway 250 and a flow rate of 90 ml/min through the outlet pathway, there is a transfer of 10 ml/min from the dialysate into the blood stream in order to compensate for the flow rate differential. It should be appreciated that the flow rate values in the preceding examples and following examples are only for purpose of example and that the actual flow rates as well as the relative flow rates can vary to achieve a desired level of ultrafiltration or reverse ultrafiltration.

The speed of the third pump 270 can be varied to selectively vary an amount of ultrafiltration. For example, if it is determined that the ultrafiltration is greater than desired when pulling fluid out of the blood, for example, the pump speed of the third pump 270 can be slowed down, reducing the amount of extra fluid that the third pump 270 draws out of the dialyzer. Where the ultrafiltration is not great enough when compared against a desired predetermined value, the pump speed of the third pump 270 may be increased in the case where fluid is being pulled out of the blood into the dialysate, for example, to draw an even greater amount of fluid out of the dialyzer and, hence, the blood.

In another embodiment, the third pump 270 may be coupled to a source of fluid such that the third pump 270 outputs extra fluid into the flow pathway via the secondary outlet pathway second valve 285, such as in the embodiment of FIG. 18. The extra fluid introduced into the flow pathway is transferred across the semi-permeable membrane 215 into the blood.

10. Flow Balancer System: Operation of Pumps to Achieve Hemodiafiltration

The dialysis system is configured to achieve hemodiafiltration by oscillating the speed of the third pump between (1) a first speed such that the second and third pump collectively achieve a flow rate through the outlet pathway that is greater than the flow rate through the inlet pathway; and (2) a second speed such that the second and third pump collectively achieve a flow rate through the outlet pathway that is less than the flow rate through the inlet pathway. In this manner, the third pump 270 can be used to intermittently alternate the flow rate differential between a state where the dialyzer 15 pulls fluid from the blood stream into the dialysate and a state where the dialyzer 15 pushes fluid from the dialysate into the blood stream. Over a predetermined span of time, there should be a zero net loss (or substantially a zero net loss) of fluid from the blood and a zero net gain (or substantially a zero net gain) of fluid into the blood for the process of hemodiafiltration. However, during that span of time, the dialyzer 15 periodically transfers fluid into the blood from the dialysate and periodically transfers fluid out of the blood into the dialysate. If ultrafiltration is desired to be performed at the same time as the hemodiafiltration, then the pumps can be operated in such a way so that in addition to the cycling of fluid into and out of the blood over time, there also occurs a net gain or loss of fluid to or from the blood over a predetermined span of time.

For example over an exemplary time span of ten minutes, the first pump 255 is set to provide a flow rate of 100 ml/min through the inlet pathway 250 and the second pump 265 is again deliberately set out of balance with the first pump 255, to provide, for example, a flow rate of only 80 ml/min. The speed of pump 270 can be cycled between a rate of 10 ml/min for a period of 30 seconds and 30 ml/min for a period of 30 seconds. During the periods when the speed of the third pump 270 is at a rate of 10 ml/min, the total flow rate through the outlet pathway 260 is 90 ml/min with the flow rate through the inlet pathway 250 at 100 ml/min, resulting in an unbalanced flow rate that causes the dialyzer 15 to transfer 10 ml/min of fluid into the blood stream. During the periods when the speed of the third pump 270 is at a rate of 30 ml/min, the total flow rate through the outlet pathway 260 is 110 ml/min with the flow rate through the inlet pathway 250 at 100 ml/min, resulting in an unbalanced flow rate that causes the dialyzer 15 to transfer 10 ml/min of fluid from the blood stream into dialysate. Over the span of ten minutes with alternating periods of 30 seconds as described above, there is a net balanced flow rate of 100 ml/min across the dialyzer without any net addition or subtraction of fluid from the blood. This serves the purpose of passing fluid to the blood across the membrane and then fluid from the blood to the dialysate across the membrane to achieve hemodiafiltration of the blood and increases the removal of large-molecular waste products that would not otherwise be effectively dialyzed. In this way, operation of the three or more-pump system can achieve all of hemodialysis, ultrafiltration and hemodiafiltration through how the speeds of the first, second, and third pumps are controlled. This type of operation has heretofore not been possible in other dialysis systems.

In another embodiment, shown in FIG. 18, the third pump is located on the inlet flow side of the dialyzer instead of on the outlet flow path, such that the first and third pumps collectively achieve the desired inlet flow rate and the second pump achieves the desired outlet flow rate to perform one or more of hemodialysis, ultrafiltration and hemodiafiltration.

Between dialysis treatments, the flow pathways may be rinsed and/or disinfected. A rinse fluid, such as, but not limited to disinfectant solution and water, is routed through the flow pathways while the valves are in the bypass setting. During rinse mode, the third pump 270 may or may not be operated with the first pump 255 and second pump 265 to achieve fluid flow through the system.

11. Dialyzer: Exemplary Microfluidic Embodiments

As discussed above, the dialyzer may comprise a microfluidic transfer device. Several exemplary embodiments of microfluidic transfer devices are described below including devices with microfluidic channels or flow fields that serve as the blood flow compartment and dialysate flow compartments of the dialyzer. In an embodiment, a flow field is a microfluidic pathway with an aspect ratio of about 10 or more, where the aspect ratio is defined as ratio of the width of the microfluidic pathway and the depth of the microfluidic pathway and fluid flows substantially in the direction of the length of the microfluidic pathway.

A. Microfluidic Transfer Device Description

Figure 21:
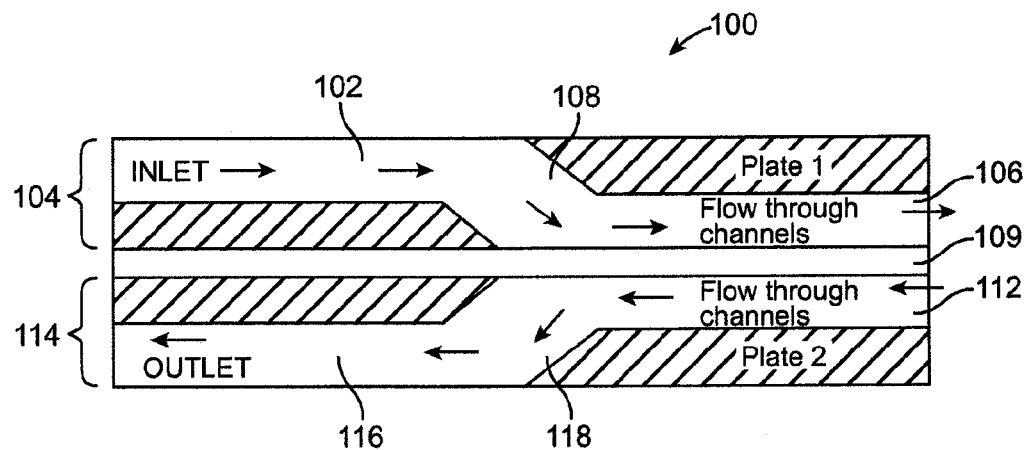
FIG. 21 is a schematic view of a microfluidic transfer device having a through-flow via.

FIG. 21 depicts a counter current flow diagram 100 for a first fluid and a second fluid. Although the flow pathway is described in the context of a microchannel, a flow pathway may also be used through a flow field. Moreover, although various embodiments described herein are shown with microchannel configurations, each embodiment could be constructed and operate using a fluid flow field rather than a microchannel.

A first fluid enters microchannel inlet 102 and flows through upper lamina 104 to microchannel 106 by way of via 108 where the fluid contacts transfer layer 110, which serves as the semi-permeable membrane 215 of the dialyzer. Concurrently, a second fluid in microchannel 112 contacts transfer layer 110 before flowing through lower lamina 114 to outlet 116 by way of via 118. Transfer layer 110 may be a semipermeable membrane chosen for the specific application to allow transfer of one or more substances from the fluid in microchannel 106 to the fluid in microchannel 112, or visaversa. For example, the specific application may be a hemodialysis procedure.

The width of microchannels 106 and 112 will be the widest possible considering operating parameters and construction requirements, such as to substantially prevent the transfer layer 110 from sagging into the microchannels. The actual width will vary depending on certain factors, such as the rigidity of the transfer layer 110 and the pressure differential across the transfer layer. Typical microchannel widths are between 100 μm and 500 μm, and more typically between about 200 μm and about 400 μm.

For the dialyzer, transfer layer 110 may be any material which allows selective transfer of a target substance(s) through the transfer layer. A person of ordinary skill in the art will recognize that the membrane selection will depend on other design criteria including, without limitation, the substance being transferred, other substances present in the fluids, the desired rate of transfer, the fluids carrying the substance, the fluid receiving the substance, operating temperature, and operating pressure. Suitable membranes may include, without limitation, polymer, copolymer, metal, ceramic, composites, polysulfone-nanocrystalline cellulose composite, gas-liquid contactor membranes, hollow fiber membranes, and fluid membranes. Some suitable membranes for the transfer layer include without limitation, polysulphone, polyethersulfone, polyacrylanitrile, cellulose acetate, cellulose di-acetate, and cellulose tri-acetate.

Laminae 104 and 114 may be any material capable of being patterned with features useful for a particular application, such as vias and microchannels or such as support structures for flow fields. Lamina thickness may be between about 200 µm and about 1000 µm, with typical thicknesses being between about 300 µm and about 500 µm. Suitable lamina materials include, without limitation, polymers and metals. Examples of suitable polymeric materials include polycarbonate, polyethylene terephthalate (PET), polyether imide (PEI), poly(methyl methacrylate) (PMMA), and halogenated polyethylene such as poly(tetrafluoroethylene) (PTFE). Metal laminae may be any that can have desired features formed therein, such as materials that can be photo-chemically etched or otherwise machined to have desired features, including blind features. Examples include stainless steels, copper, titanium, nickel, and aluminum.

Figure 22:
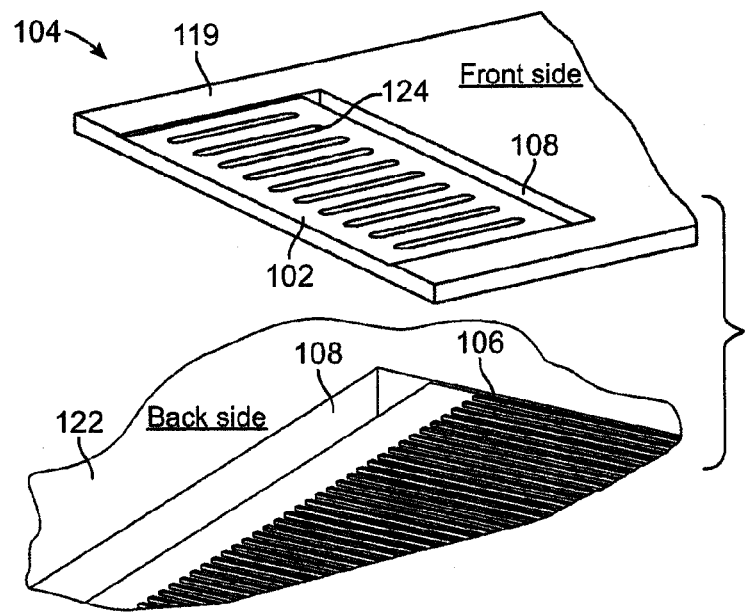
FIG. 22 is a perspective view of one embodiment of a single layer of the microfluidic transfer device.

FIG. 22 shows a perspective view of one embodiment of a lamina design. Although FIG. 22 is described in the context of a microchannel, a similar header configuration may be used for fluid flowing into a flow field. The header side 120 of lamina 104 comprises inlet 102 for receiving a fluid and directing the fluid to via 108 where the fluid flows through the plate to the microchannel side 122 (or flow field side) of the plate. The fluid then flows through the microchannels 106 or flow field, where the fluid contacts the transfer layer, not shown. The inlet 102 has support structures 124 for preventing collapse of adjacent lamina into the inlet 102. FIG. 22 discloses microchannels 106 as plural parallel microchannels, however the present disclosure is not limited to this configuration.

1. Flow Fields

Figure 23:
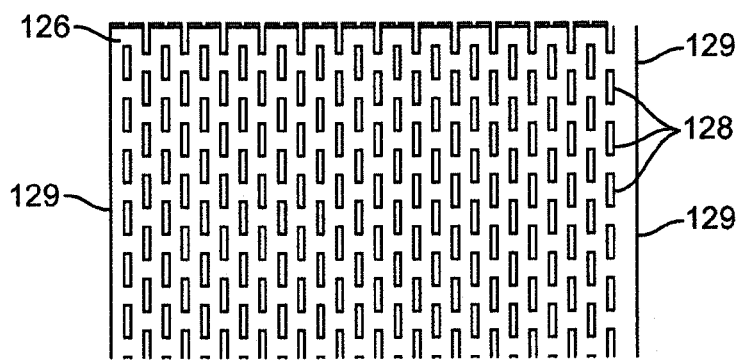
FIG. 23 is a plan view of microfluidic flow field with wall segment supports.

As mentioned, any of the embodiments may incorporate one or more flow fields rather than microchannels. FIG. 23 shows an embodiment utilizing a flow field 126 rather than the parallel microchannels used in the embodiment of FIGS. 21 and 22. The flow field 126 may be generally formed by a pair of opposed walls 129 that define the outer periphery of the flow field 126. A space is positioned between the walls and fluid flows within the space from an inlet toward an outlet. One or more discrete support structures, such as wall segments 128, are positioned in the space between the walls. The support structures at least partially function to provide support to adjacent lamina to prevent the lamina from collapsing on another. The support structures also prevent the membrane from collapsing into the flow path and blocking the flow of either blood or dialysate. The support structures may be arranged in a variety of spatial arrangements relative to one another. The support structures may have a variety of shapes and sizes and may be in the form of pins, wall segments, bumps, protrusions, etc.

The support structures differ from the elongated walls or dividers that form the microchannels in that the support structures do not define discrete, elongated flow pathways. Rather, a plurality of the support structures are positioned in the general flow space between the opposed walls 129 without specifically guiding the fluid in a particular direction. The support structures permit more freedom of flow direction for the fluid relative to the finely-guided directional flow of the microchannels.

In addition, the discrete, spaced-apart nature of the support structures results in exposure of more transfer layer surface than where contiguous microchannel dividers are used. Exposure of more of the interposed transfer layer to the fluids to be dialyzed, for example, improves overall device efficiency. A person of ordinary skill in the art will recognized that it is desirable to maximize the area of the transfer layer exposed to the fluid while maintaining the integrity of the transfer layer with sufficient support structures so that the transfer layer does not collapse into a portion of the flow field. Moreover, the flow field embodiments mitigate flow occlusion cause by entrapped air bubbles by allowing fluid to flow around the air bubbles, which may not occur as readily in the more constricted volume of a microchannel because the bubble may be of a size to significantly block the flow in a particular channel.

In the example of FIG. 23, the support structures are in the form of wall segments 128 comprised of rectangular- or prismic-shaped bodies that extend upwardly from the surface of the lamina. The wall segments 128 are positioned in groups such that a single group forms a column from the viewpoint of FIG. 23. The entire flow field 126 includes a series of columns. Each column has a plurality of wall segments 128 aligned end-to-end and spaced from one another within the column. Each of the columns is spaced from an adjacent column. The spacing between wall segments may vary within a single column, as can the spacing between one column and an adjacent column. Moreover, the wall segments 128 can be arranged in other spatial patterns and are not limited to being arranged in column patterns.

Figure 24:
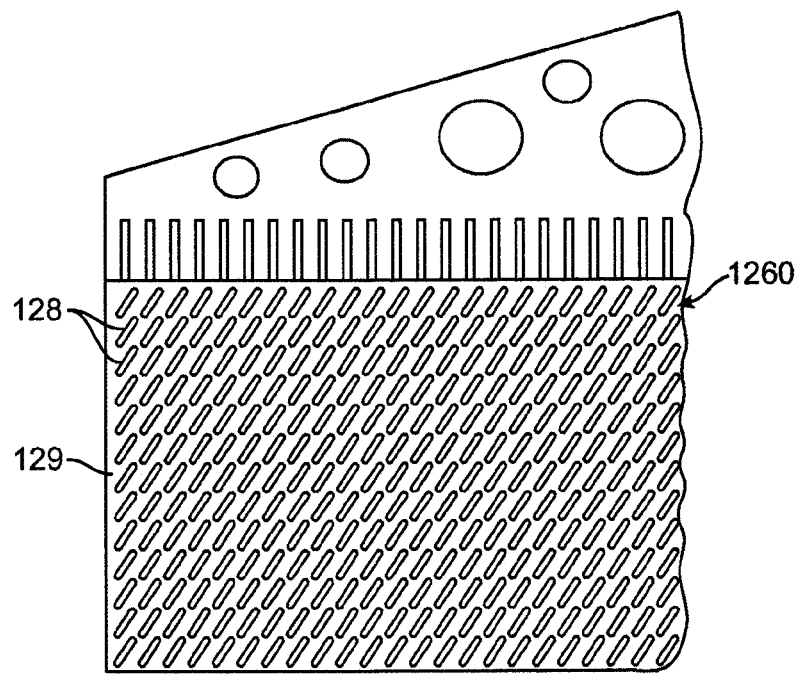
FIG. 24 is a plan view of a microfluidic flow field with angled wall segments.
Figure 25:
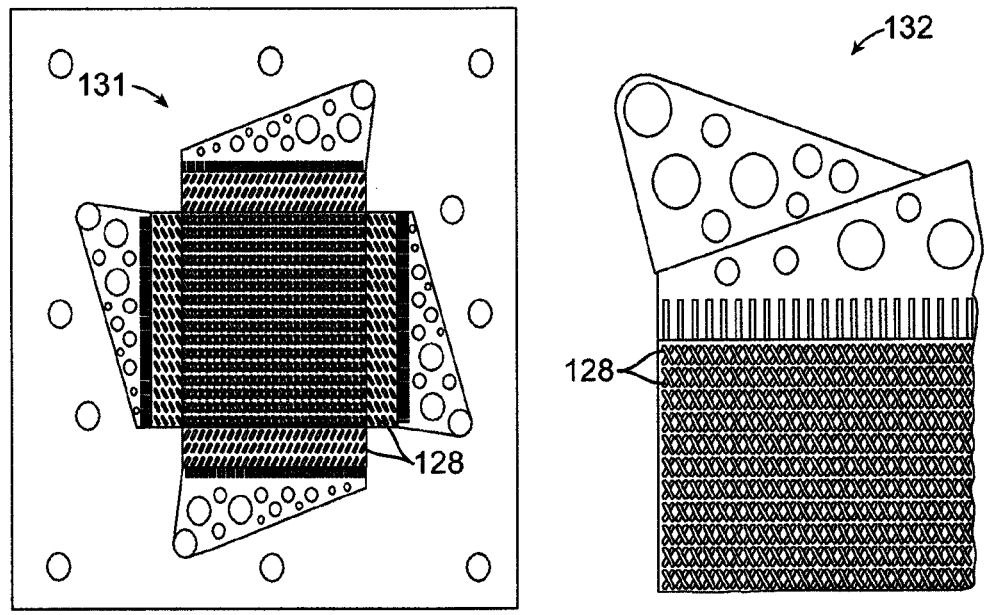
FIG. 25 is a schematic plan view of the juxtaposition of flow fields with angled wall segments.

FIG. 24 shows another example of a flow field 126 with the wall segments 128 angled slightly relative to the long axes of the opposed walls 129. The magnitude of the angle of the wall segments relative to the opposed walls 129 may vary. All of the wall segments 128 may be oriented at the same angle. Alternately, the angle may vary from one wall segment 128 to another wall segment 128 such that one or more of the wall segments 128 may be oriented at one angle while other wall segments may be oriented at a different angle.

Angling the wall segments 128 can result in an alignment tolerant design when the device is assembled for concurrent or countercurrent flow. It can be desirable for one wall segment to be positioned at least partially atop another wall segment when the adjacent layers are stacked in order to provide proper structural support between the layers in the stack. In this regard, the wall segments 128 can have relative sizes and shapes and can also be arranged in patterns to maximize the likelihood of the wall segments aligning atop one another when the layers are stacked. FIG. 5 shows a juxtaposition of adjacent layers in cross current configuration 130 and concurrent configuration 132, each having angled wall segments 128. The angled nature of the wall segments increases the likelihood of the wall segments intersecting or stacking atop one another when the laminae are stacked. Slight movement of one layer relative to the other in either the x or y direction will still support the membrane at the intersection of the wall segments.

Figure 26A:
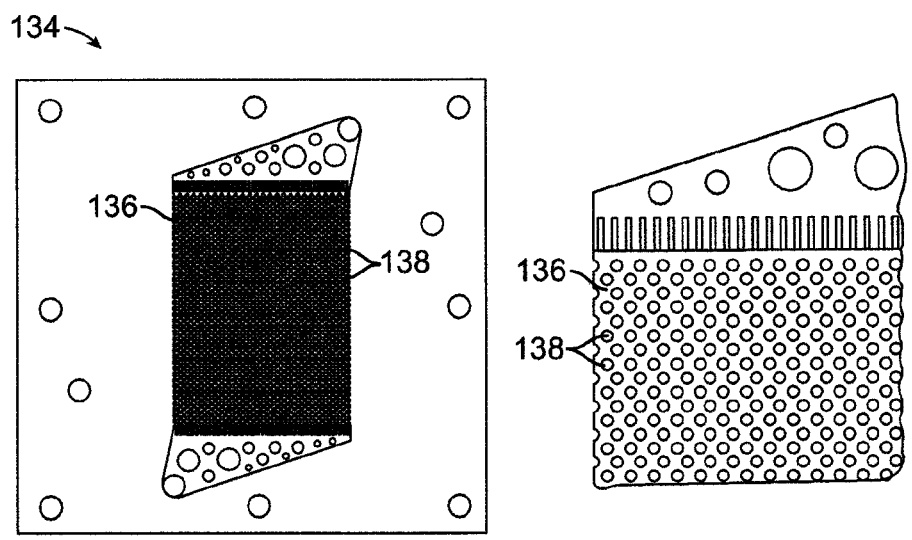
FIG. 26A is a plan view of a microfluidic flow field with cylindrical supports.
Figure 26B:
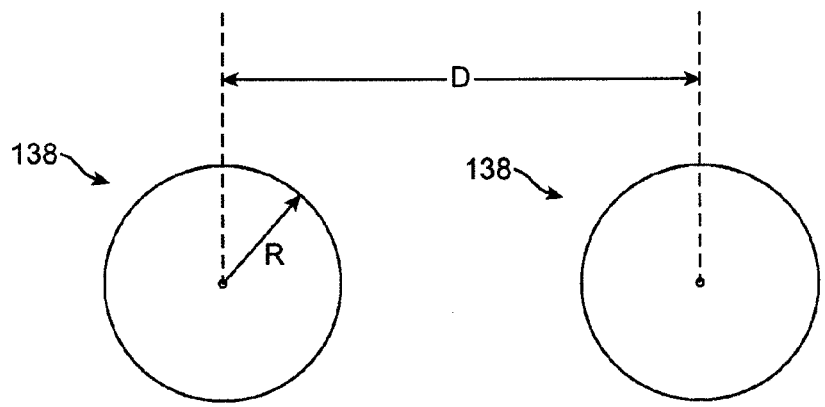
FIG. 26B shows a top view of a pair of cylindrical supports.
Figure 26C:
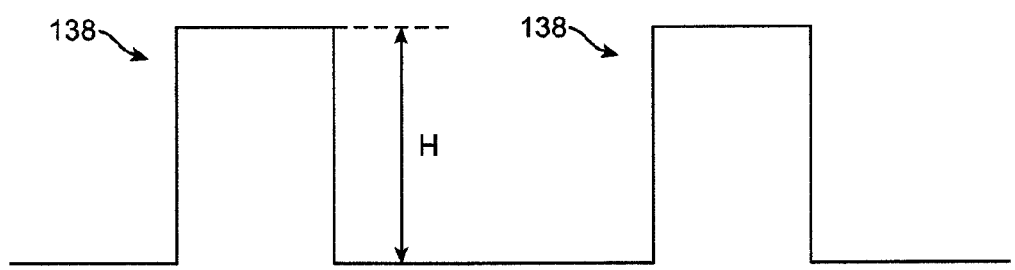
FIG. 26C shows a side view of a pair of cylindrical supports.
Figure 27:
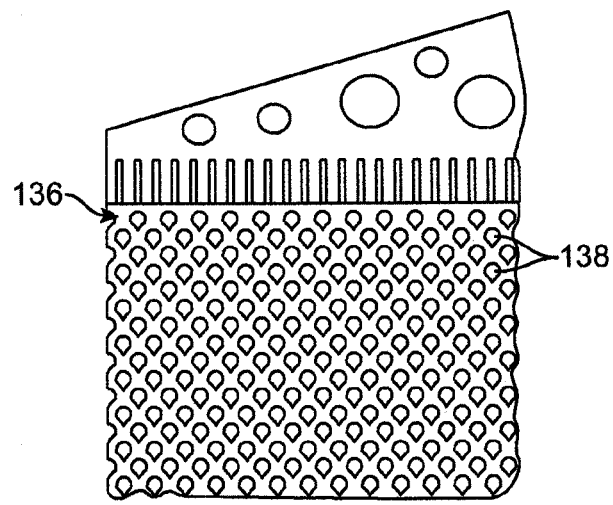
FIG. 27 is a plan close-up view of a microfluidic flow field with tear-drop shaped support structures.

FIG. 26A discloses a laminate 134 having a flow field 136 wherein the support structures comprise plural cylindrical support posts 138. Similar to the wall segments 128 (FIG. 23), the plural support posts 138 increase the surface area of the transfer layer (not shown) exposed for transfer. Additionally, fluid is not confined to narrow channels as in microchannels 106 (FIG. 22), thereby allowing fluid to traverse laterally around flow occlusions such as air bubbles or contaminant. FIG. 26B shows a plan view of a pair of support structures comprised of the cylindrical support posts 138. FIG. 26C shows a schematic side view of a pair of cylindrical support posts 138. The dimensions of the cylindrical support posts 138 may vary as may the relative spacing between adjacent cylindrical support posts 138 to provide the flow field with desired flow characteristics. For example, the radius R of each support post 138 may be predetermined, as may the distance S between adjacent support posts 138. The height H of each support post may also vary. The support posts 138 may be prisms with circular bases, such as a cylinder. However the bases of the prism may be any shape, such as a rectangle, triangle, ellipse, polygon, or other geometric shape. For instance, FIG. 27 discloses a flow field 136 having support structures formed of tear-drop shaped support posts 138. This embodiment is configured for streamlining fluid flow through the flow field 136.

In an embodiment, the size of the support posts is the minimum possible—measured in diameter for cylindrical posts, width of rectangular posts, or twice the average distance to the geometric center for irregular shapes—without puncturing the transfer layer and large enough to allow alignment of posts of adjacent layers. The support structures are typically greater that zero µm and less than 1000 µm. More typically the support structures are greater than zero µm and less than 500 µm, such as about 100 µm to about 400 µm. A person of ordinary skill in the art will recognize that the desired shape and size of the support structures will depend on various factors such as the transfer layer material and thickness, the fluids involved, manufacturing alignment tolerances, and transfer layer efficiency.

Figure 28:
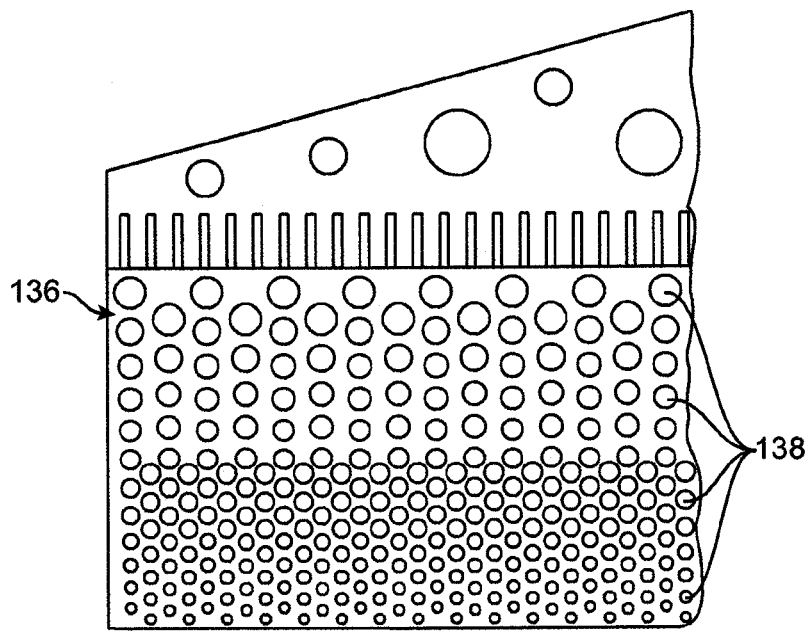
FIG. 28 is a plan close-up view of a microfluidic flow field having gradient support structure density and size.
Figure 29:
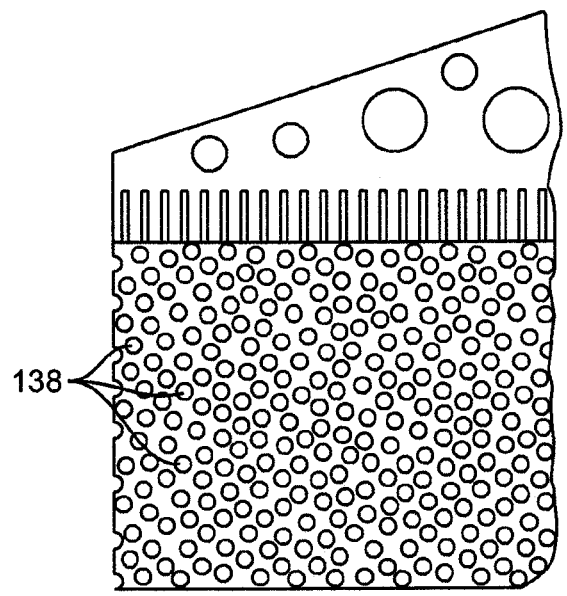
FIG. 29 is a plan close-up view of a microfluidic, flow field with randomly distributed support structures.

The flow field 136 may define an array of support structures 138 having gradient densities and varying sizes as shown in FIG. 28. For instance, one end of the flow field 136 may have larger and sparse support structures 138, gradually decreasing in size and increasing in density approaching the opposite end. Additionally some or all of the flow field may be treated with a surface treatment to enhance flow dynamics. For instance the surface may be treated to render it hydrophilic to reduce air entrapment. Alternatively, it may be treated selectively to be hydrophobic in a low support-density area and hydrophilic in a high support-density area, encouraging entrapped air to move through the sparse area to the dense area where wicking and mechanical forces can force the gas out. Also, the support structures 138 may be randomly distributed throughout the flow field subject to design constraints as shown in FIG. 29.

The distance S between the support structures 138 may be the widest possible considering operating parameters and construction requirements, such as to substantially prevent the transfer layer 110 (FIG. 21) from sagging into the flow field 136. The actual width will vary depending on certain factors, such as the rigidity of the transfer layer 110 (FIG. 21) and the operating pressure differential across the transfer layer. Typical widths are between 100 µm and 500 µm, and more typically between about 200 µm and about 400 µm.

Microchannel or flow field depth creates a transfer efficiency advantage. Micron scale dimensions reduce mass transfer limitations by reducing diffusion or conduction lengths through the bulk fluid, thereby increasing the mass rate per unit area of transfer layer 110 (FIG. 21), consequently increasing efficiency and reducing device size. Microchannel or flow field depth is typically greater that zero and less than 1000 µm. More typically the depth is greater than zero and less than 400 µm. Even more typically, the depth is greater than zero and less than about 100 µm, such as from about 10 µm to 90 µm.

2. Mass Transfer Devices for use as Dialyzers

Figure 30:
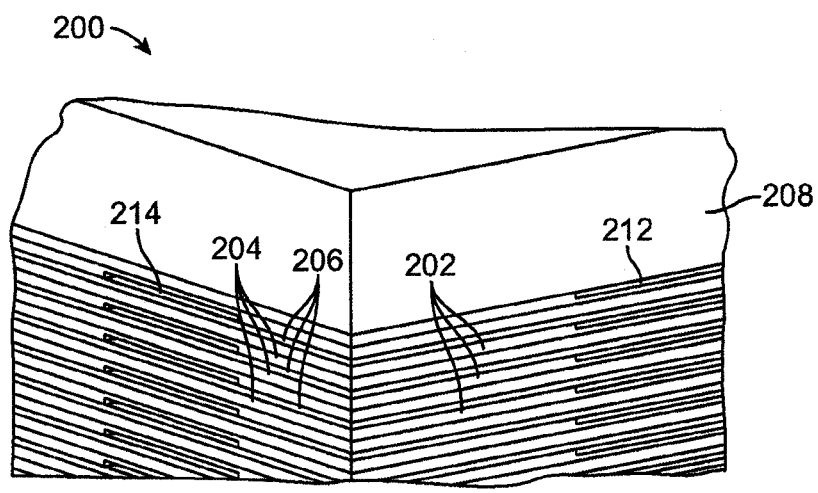
FIG. 30 is a partial perspective view of an assembled device showing fluid inlets and outlets.
Figure 31:
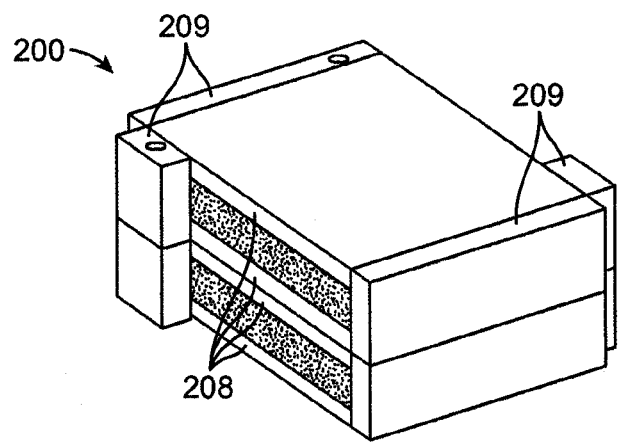
FIG. 31 is a perspective view of two combined assembled devices with fluidic headers attached.

Referring to FIGS. 30 and 31, assembled mass transfer device 200, which can serve as a dialyzer, is comprised of laminae 202, laminae 204, and transfer layers 206. Compression plates 208 are provided to apply pressure to the layered plates 202 and 204 and transfer layers 206 to afford substantially sealed fluid microchannels or flow fields. Compression plates 208 apply pressure using, for example, fasteners connecting the compression plates or by placing device 200 in a clamping mechanism. A person of ordinary skill in the art will recognize that various additional methods of applying force to the compression plates exist in the art. Fluidic headers 210 are operably connected to mass-transfer device 200, and are fluidly connected to microchannel inlets 212 and microchannel outlets 214, for delivering fluids to the internal microchannels 106 and 112 (FIG. 21). FIG. 31 shows two microfluidic transfer devices arranged in parallel, however a person of ordinary skill in the art will recognize that any number of devices may be configured in parallel, series, or both.

The compression plates 208 may be made from any material with sufficient rigidity to evenly compress the laminae 202 and 204 and transfer layers 206. Suitable materials include, without limitation, polymer, metals, ceramic, or composites. An exemplary material may be, for instance, acrylic. However, a person of ordinary skill in the art will recognize that the compression plate material and its thickness may depend on various factors, for instance, the number of layers in the stack, the required shape to affect a seal, and the operating temperatures. The compression plates 208 may be flat or may have a curved face, such as a convex face, having a curvature suitable for preferably evenly distributing pressure through the device 200.

Figure 32:
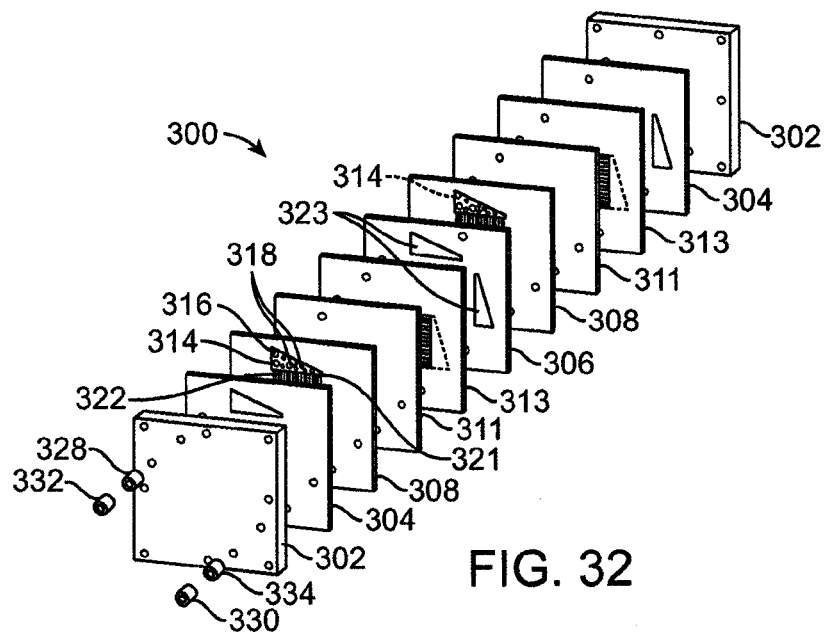
FIG. 32 is an assembly view of one embodiment of a microfluidic transfer device with single-sided lamina.
Figure 33:
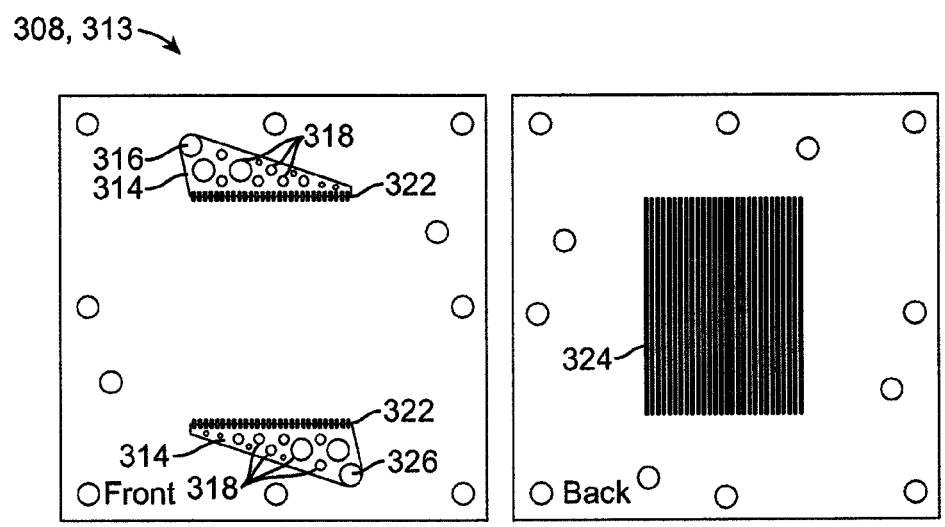
FIG. 33 is a plan view of one embodiment of a lamina.

FIG. 32 shows an assembly view of one embodiment of a microfluidic transfer device 300. Mass transfer device 300 comprises a sequenced stack of lamina held between compression plates 302. The sequenced stack comprises head gaskets 304, and repeating subunits separated by gaskets 306. The repeating subunits comprise, in order, a first lamina 308, a transfer layer 310, and a second lamina 312. The number of subunits will depend on the application and the volumetric throughput and transfer capacity required. Additionally, devices may be connected in parallel as shown in FIG. 31. Laminae 308 and 312 are substantially similar in design. Referring to FIG. 33, laminae 308 and 312 have fluid headers 314, fluid inlet 316, support structures 318, vias 322, microchannels 324 (or flow fields) located on the opposite side, and fluid outlet 326. This can be seen in more detail in the discussion of FIG. 36 below. Referring again to FIG. 32, the gaskets 304 and 306 have cutouts 325 so that the gasket does not cover the fluid headers 314, preventing collapse of the gasket material into the header and impeding fluid flow. The support structures 318 may transfer compression force through the stack to facilitate compression sealing throughout the stack and prevent the adjacent lamina from collapsing into the header. The support structures may also prevent the transfer membrane from blocking fluid flow in and through the header. Operatively connected to compression plate 302 are fluid connectors 328, 330, 332, and 334.

Figure 34:
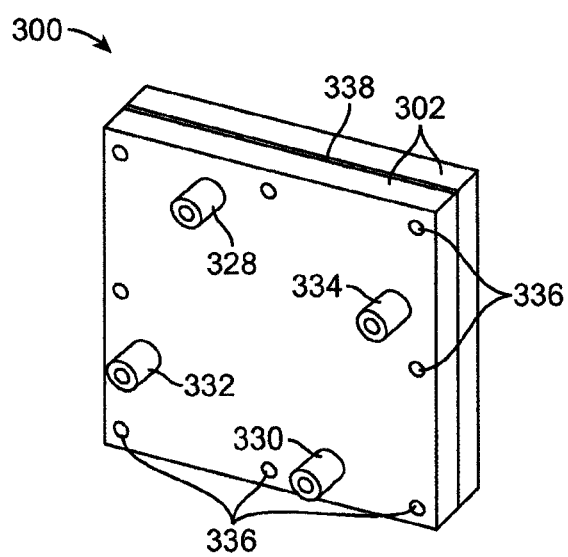
FIG. 34 is a perspective view of the assembled device shown in FIG. 26.

FIG. 34 shows a perspective view of assembled microfluidic transfer device 300. The compression plates 302 have apertures 336 for receiving fasteners for coupling together and compressing the stack 338. A first fluid enters the device 300 through fluid connector 328 and exits the device through fluid connector 330. A second fluid enters the device 300 through fluid connector 332 and exits the device through fluid connector 334.

Figure 35:
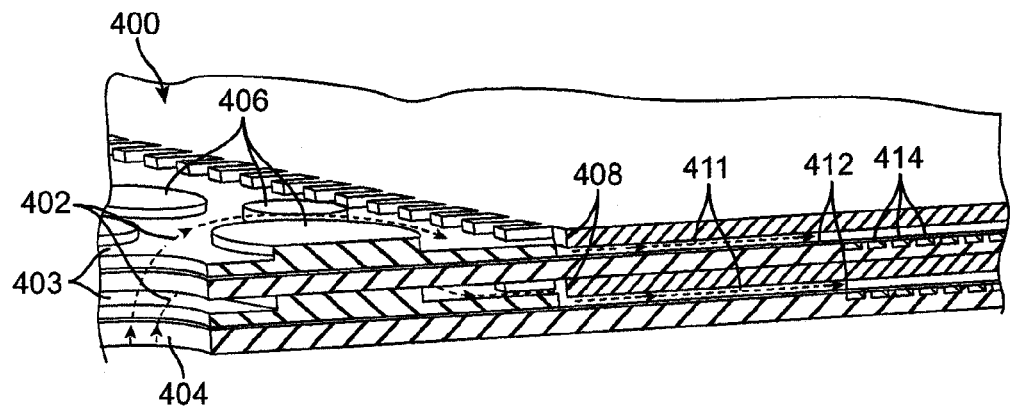
FIG. 35 is a detail view of the internal fluid flow paths in the device of FIG. 26.

FIG. 35 provides a detailed view of the internal flow path of two subunits of stack 400. Fluid flow paths 402 show a first fluid (e.g., blood) entering through fluid inlet 404. Fluid inlet 404 is a through-hole which fluidly connects the first fluid to subunits in the stack. Fluid enters the headers 405, flows around the support structures 406 through the vias 408 to microchannels 410 or flow fields where it contacts transfer layers 412. Transfer layers 412 operatively connect microchannels 410 or flow fields containing the first fluid and microchannels 414 or flow fields containing the second fluid (e.g., dialysate) to allow transfer select substances (such as blood waste products) in the fluids. For instance a mass transfer layer, e.g. a membrane, may allow for membrane permeable components of the first and second fluid to transfer across the membrane from one fluid to the other.

Figure 36:
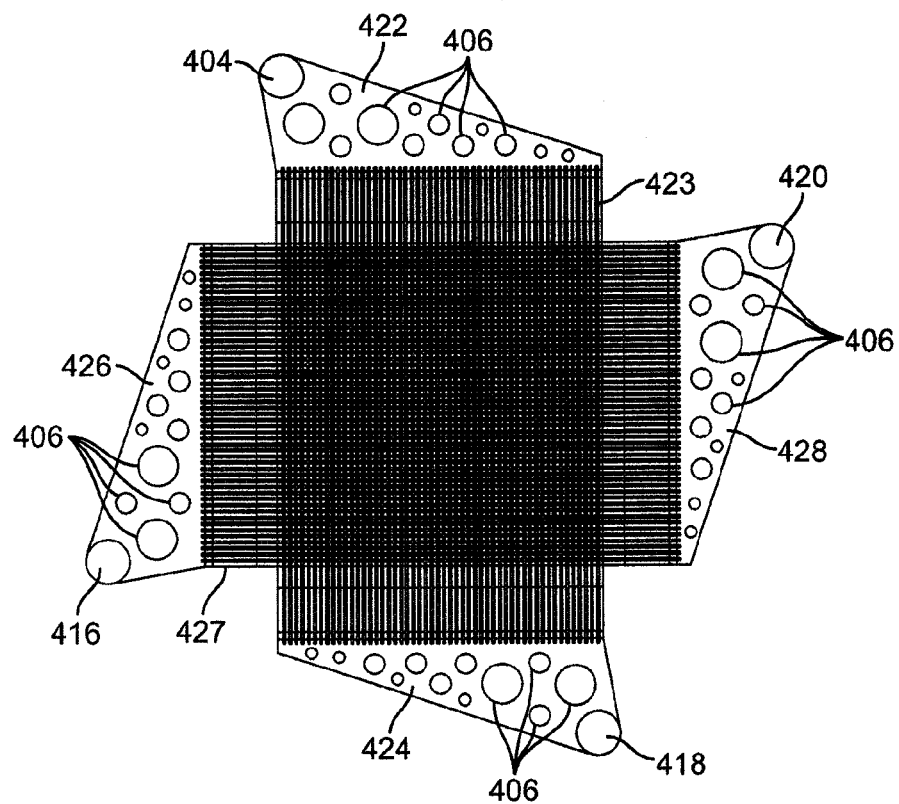
FIG. 36 is a schematic plan view of the juxtaposition of fluid headers and microchannels of adjacent layers, having cross-current flow.

FIG. 36 is a schematic view of the fluid flow patterns of both fluids juxtaposed. Fluid inlet 404 provides the first fluid to inlet header 422, where it flows around support structures 406 to microchannels 423, and is collected at the other end of the microchannels in outlet header 424, then exits through fluid outlet 418. If the embodiment of FIG. 36 included a flow field rather than microchannels 423, then the fluid would flow from the inlet header 422, through the flow field, and toward the outlet header 424. As the fluid flows through the flow field, it would flow around the various support structures positioned within the flow field.

Figure 37:
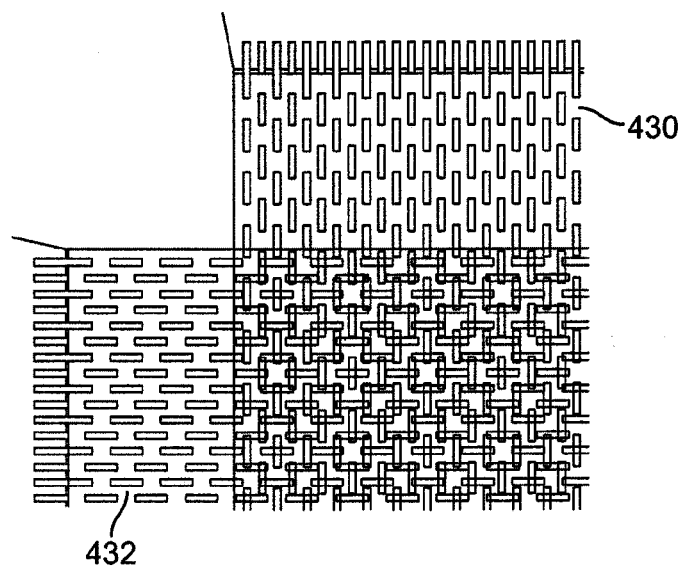
FIG. 37 is a partial schematic plan view of the juxtaposition of adjacent layers having the flow field shown in FIG. 23.

The second fluid enters through fluid inlet 416 into inlet header 426, where it is directed to microchannels 427 or flow field, and is collected in outlet header 428 and exits through outlet 420. FIG. 36 discloses a device having the first and the second fluid flowing orthogonal to each other; however a person of ordinary skill in the art will recognize that one may configure this device for concurrent, countercurrent, or crosscurrent flow. FIG. 37 discloses the juxtaposition of adjacent layers of another embodiment utilizing flow fields 430 and 432 rather than plural parallel microchannels.

In an embodiment, the mass transfer device is a dialyzer such that the first fluid is blood and the second fluid is dialysate. The blood enters the fluid inlet 404 and flows to the inlet header 422. The blood then flows into the flow field or microchannels toward the outlet header 424, and then exits through fluid outlet 418. The dialysate enters the dialyzer through the fluid inlet 416 and flows into the inlet header 426, where it is directed to microchannels 427 or flow field, and is collected in outlet header 428 and exits through outlet 420. As the blood and dialysate flow through their respective flow fields, solutes diffuse across the mass transfer layer. A pressure gradient may be formed between the respective flow fields in order to achieve hemodiafiltration of the blood where fluid periodically passes from the dialysate into the blood and/or from the blood into the dialysate, thereby transferring molecules by means of convective solute movement that otherwise would be slow to cross the membrane barrier by diffusion alone. Ultrafiltration is a process in dialysis where fluid is caused to move across a dialyzer membrane via diffusion from the blood into the dialysate for the purpose of removing excess fluid from the patient's blood stream. Along with water, some solutes are also drawn across the membrane via convection rather than diffusion. Ultrafiltration is a result of a pressure differential between the blood compartment and the dialysate compartment where fluid will move from a higher pressure to a lower pressure.

Figure 38:
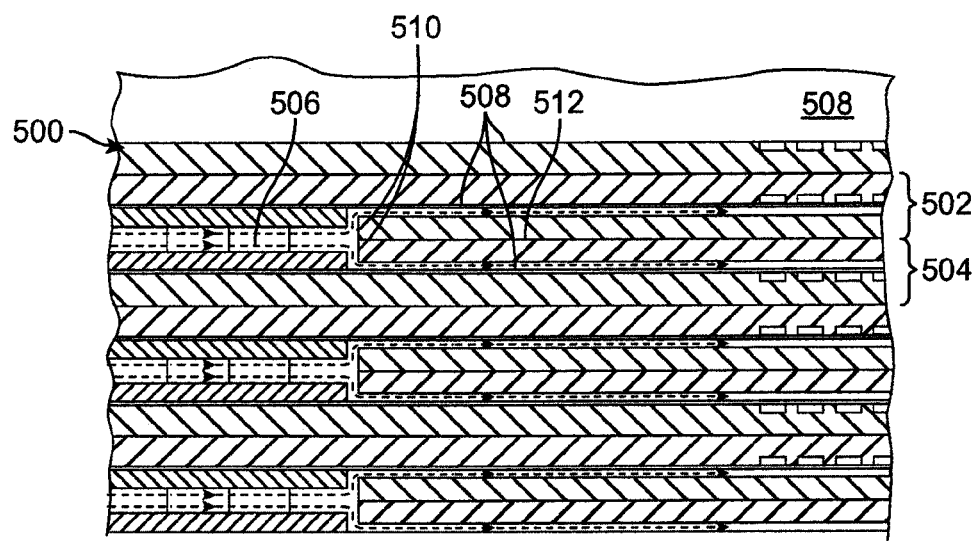
FIG. 38 is a detail view of the internal fluid flow paths of one embodiment having single-sided mirrored design.

FIG. 38 discloses an embodiment of the device 500 having alternating mirror image subunits 502 and 504. This embodiment creates combined fluid header 506, which directs fluid to microchannels 508 (or flow fields) through vias 510. The subunits 502 and 504 are separated by a gasket 512 with a cutout for header 506. This arrangement reduces the fluid cross contamination relative to embodiments having headers with dissimilar fluids facing each other. Moreover, arranging the subunits 502 and 506 in this manner allows for a single, simplified gasket design compared to the two gasket designs shown as 304 and 306 in FIG. 32. This embodiment may be configured for cross flow as shown in FIG. 38 or for concurrent or counter current flow as shown in FIG. 39.

Figure 39:
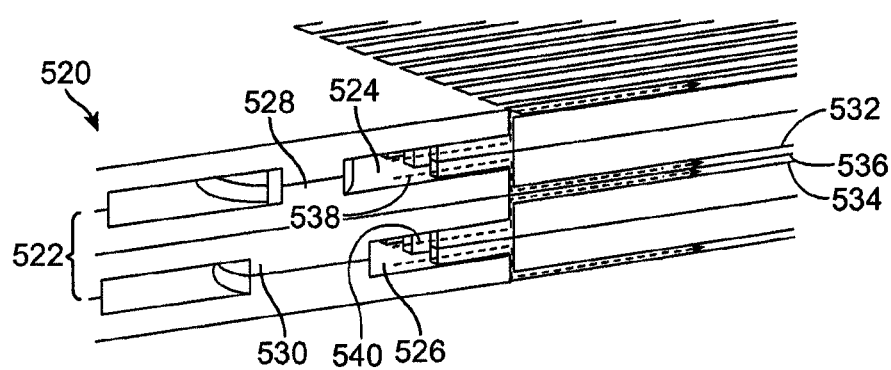
FIG. 39 is a detail perspective view of the fluid flow paths of a one embodiment having a single-sided mirrored design with parallel microchannels.

Referring to FIG. 39, device 520 comprises subunit 522 having combined headers 524 and 526. Laminae 528 and 530 comprise parallel microchannels 532 and 534 (or flow fields) separated by transfer layer 536. Parallel microchannels 532 and 534 allow concurrent flow paths 538 and 540. Alternatively, reversing the direction of either flow path 538 or 540 will achieve countercurrent flow.

Figure 40:
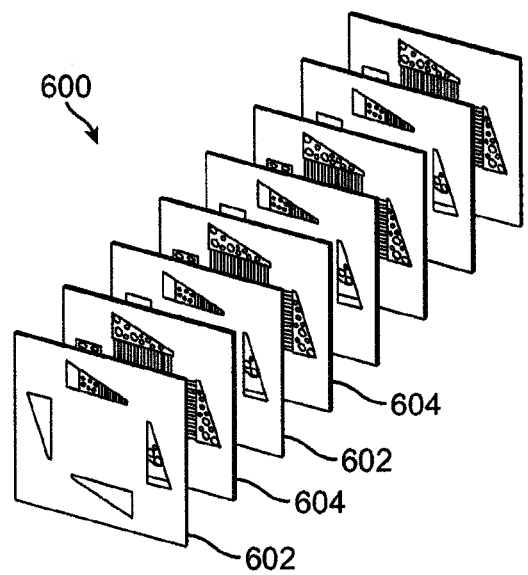
FIG. 40 is a partial assembly view of one embodiment of a microfluidic transfer device having double-sided laminae.
Figure 41:
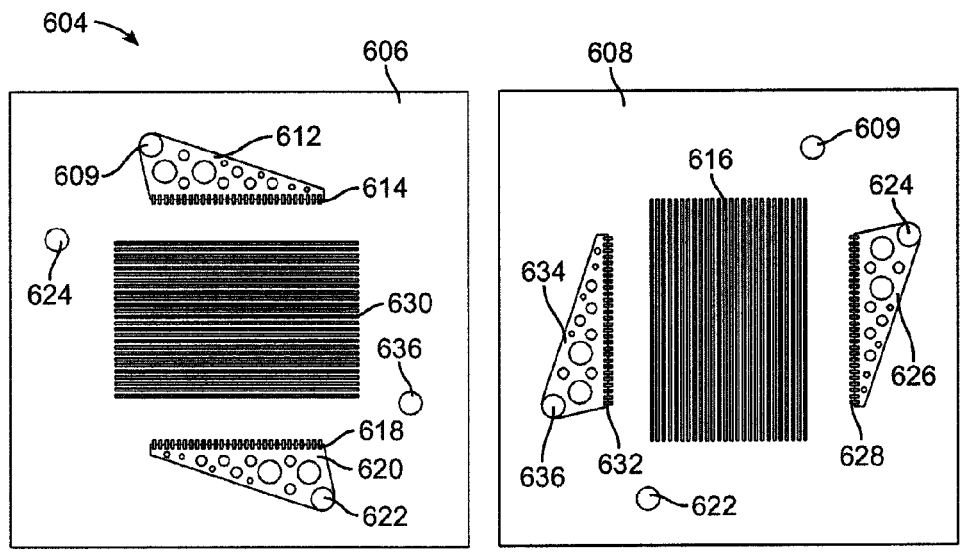
FIG. 41 is a plan view of a double-sided lamina.

In yet another embodiment, the need for gaskets between subunits is eliminated entirely. FIG. 40 discloses a partial assembly view of a mass transfer device 600 where the laminae 604 have microchannels (or flow fields) and headers on both sides. This configuration allows the device 600 to be assembled as alternate layers of identical transfer layers 602 and laminae 604. FIG. 41 is a plan view of the front 606 and back 608 of the lamina 604. The lamina front 606 has a first fluid inlet 610 fluidly connected to first fluid inlet header 612. First fluid inlet header 612 directs fluid through via 614 to first fluid microchannels 616 (or flow field) on lamina back 608. The microchannels 616 direct fluid to via 618 which fluidly connects the microchannels with first fluid outlet header 620 on lamina front 606, where the first fluid exits by first fluid outlet 622. Similarly, the lamina back 608 has second fluid inlet 624 which fluidly connects to second fluid inlet header 626. Second fluid inlet header 626 is fluidly connected to via 628 which fluidly connects the second fluid inlet header to the second fluid microchannels 630 (or flow field) on the lamina front 606. The second fluid microchannels 630 direct the fluid to via 632 which fluidly connects the second fluid microchannels and the second fluid outlet header 634, which is fluidly connected to the second fluid outlet 636.

Figure 42:
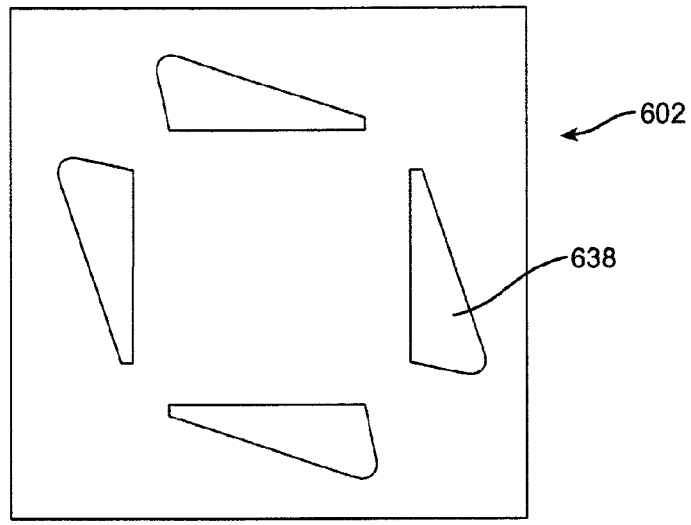
FIG. 42 is a plan view of a transfer layer.

FIG. 42 discloses the transfer layer 602 used in microfluidic transfer device 600 (FIG. 40). The transfer layer 602 has four cutouts 638 associated with the locations of the fluid headers 612, 620, 626, and 634 on plate 604 (FIG. 41). While the double sided lamina 604 allows a device with nearly half the number of lamina compared to previously disclosed embodiments, compression alone may not adequately seal the transfer layer between the headers and microchannels located on the same side of the lamina.

Figure 43:
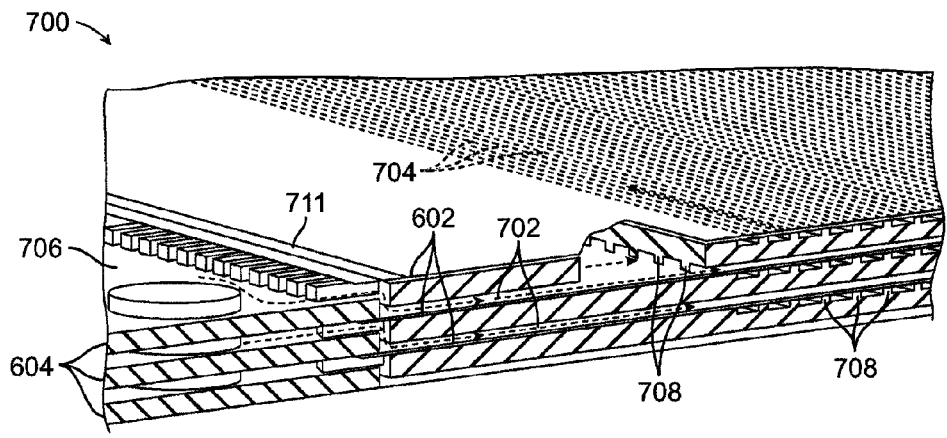
FIG. 43 is a detail view of the flow path of a microfluidic transfer device having double sided laminae.

FIG. 43 shows a detailed view of a microfluidic transfer device 700 employing double sided lamina 604. The first fluid flows from the headers 706 through lamina 604 to microchannels 702 (or flow field). Similarly the second fluid flows from a header, not shown, on lamina 604 to microchannels 704 (or flow field) located on the same side of the plate as header 706. Because the transfer layer 602 is compressed against adjacent layers by microchannel dividers 708 rather than a solid surface, fluid could leak under the transfer layer allowing fluid from header 706 to enter microchannel 704. Transfer layer bond 710 prevents this. Adhesives or laser welding could create the transfer layer bond 710, however a person of skill in the art will recognize that one may employ other methods to create the bond. Such methods include but are not limited to RF welding, ultrasonic welding, and thermal welding.

Figure 44:
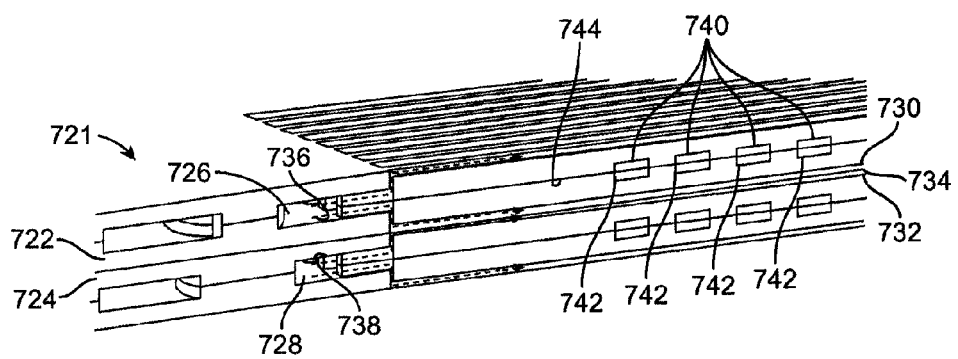
FIG. 44 is a detail view of the flow path of a microfluidic transfer device having double sided laminae with concurrent flow.

While FIG. 43 discloses a double-sided device with crosscurrent flow, it is also possible to configure a double-sided device with concurrent or countercurrent flow. For example, FIG. 44 illustrates device 720 having double-sided laminae 722 and 724 arranged to provide combined headers 726 and 728. Microchannels 730 and 732 are parallel and are separated by transfer layer 734, allowing concurrent flow paths 736 and 738. Likewise microchannels 740 and 742 are parallel to each other and are separated by transfer layer 744, allowing concurrent flow paths not shown. A person of ordinary skill in the art will recognize that this embodiment also allows countercurrent flow.

Figure 45:
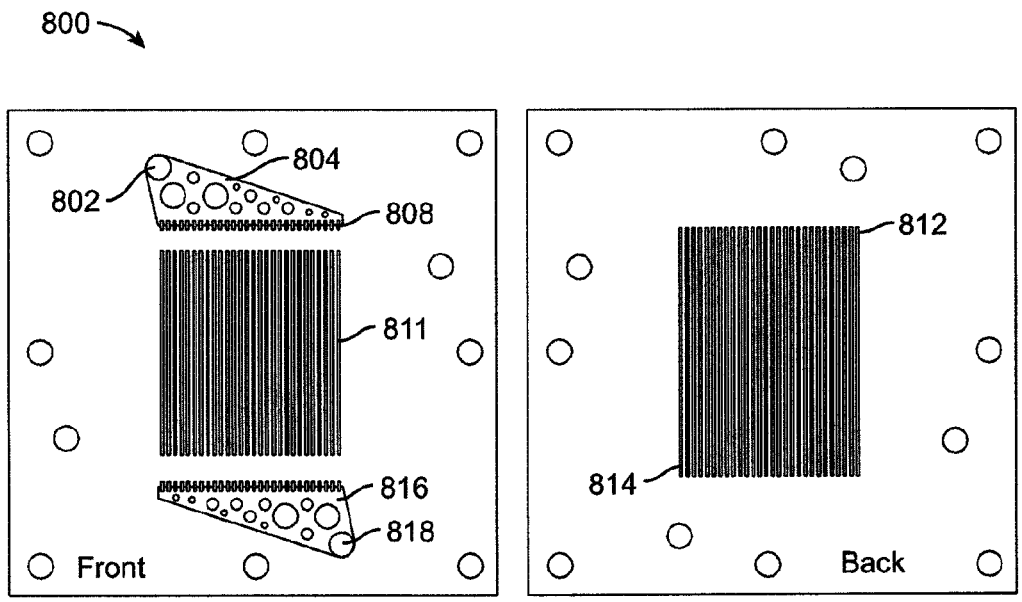
FIG. 45 is a plan view of a lamina having through-cut microchannels.
Figure 46:
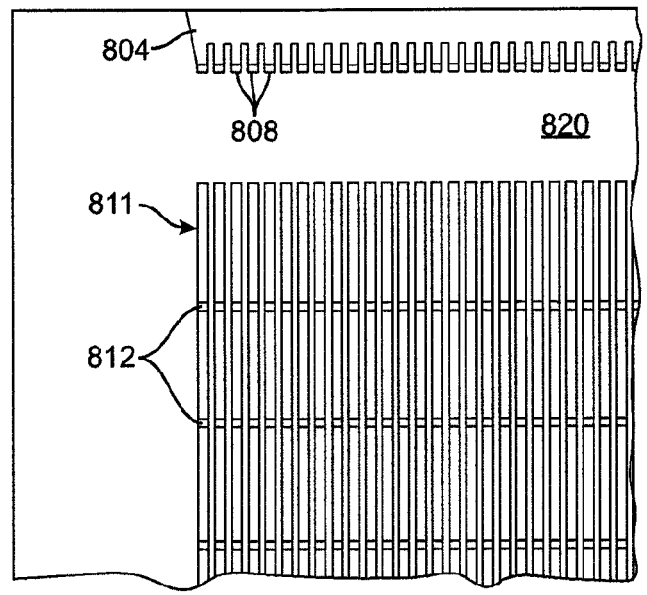
FIG. 46 is a detail plan view of a lamina having through-cut microchannels with lateral supports.

One embodiment of the microfluidic transfer device employs microchannels that are cut through the entire lamina thickness. FIG. 45 is a plan view of a through-cut lamina 800. Lamina 800 has fluid inlet 802, fluidly connected to inlet header 804. Inlet header 804 is fluidly connected to via 808. Through-cut microchannels 811 are fluidly connected to vias 808 by way of microchannels 814. Microchannels 814 fluidly connect through-cut microchannels 811 with outlet header 816, which directs fluid flow to outlet 818. With the microchannels cut through the entire lamina thickness, the microchannel dividers may need structural support. FIG. 46 shows lamina 800 having through-cut microchannels 811 supported by partial thickness dividers 812. To afford a robust compression seal, lamina 800 has a compression seal face 820 for compressing the transfer layer against the adjacent layer. Another embodiment of a through-cut microchannel lamina is shown in FIG. 47.

Figure 47:
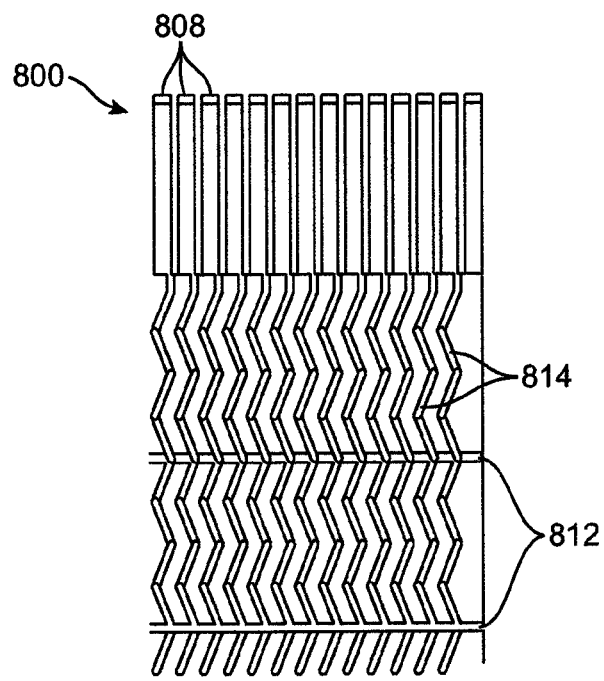
FIG. 47 is a detail plan view of a lamina having through-cut microchannels with a herringbone pattern.
Figure 48:
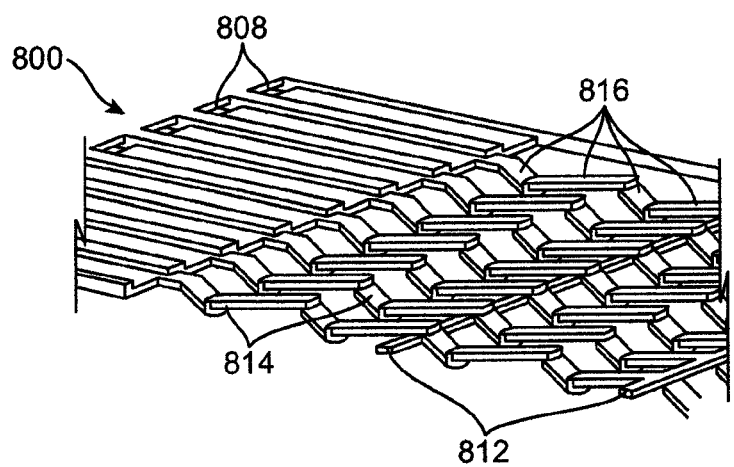
FIG. 48 is a detail perspective view of a lamina having through-cut microchannels with a herringbone pattern.

FIG. 47 shows a plan view of lamina 800 having microchannel dividers forming a herringbone pattern. Referring to FIG. 48, microchannel dividers 814 comprise plural partial thickness wall segments 816 arranged in a herringbone pattern. Partial thickness wall segments 816 alternate in the herringbone pattern such that adjacent wall segments are flush with opposite sides of the lamina 800. This design increases device efficiency by exposing a greater surface area of the transfer layer (not shown). The partial thickness wall segments 816 may essentially form a flow field rather than microchannels, as the partial thickness wall segments 816 do not necessarily constrain the fluid flow into a single channel.

Figure 49:
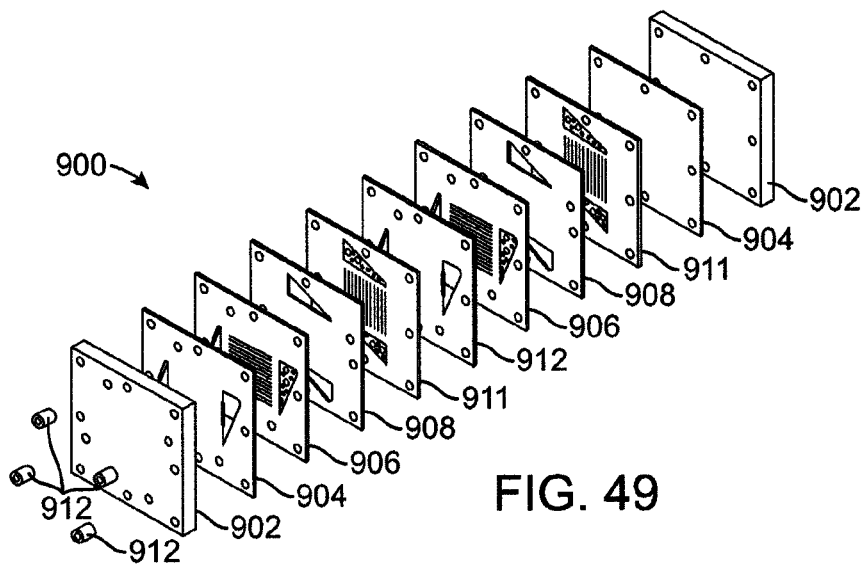
FIG. 49 is an assembly view of a microfluidic transfer device having through-cut laminae.

FIG. 49 shows an assembly view of microfluidic transfer device 900 using through-cut laminae 906. Compression plates 902, operatively connected to gaskets 904, hold and compress repeating subunits comprising, in order, first fluid lamina 906, transfer layer 908, and second fluid lamina 910. The subunits are separated by transfer layers 912. One advantage of this embodiment is the increased transfer layer exposure per microchannel. Since the through-cut microchannels are bound on two sides by transfer layers 908 and 912, which operatively connect them to adjacent plates, the transfer layer surface area per lamina is almost doubled. This allows for fewer layers, and allows reduced costs and smaller devices.

Figure 50:
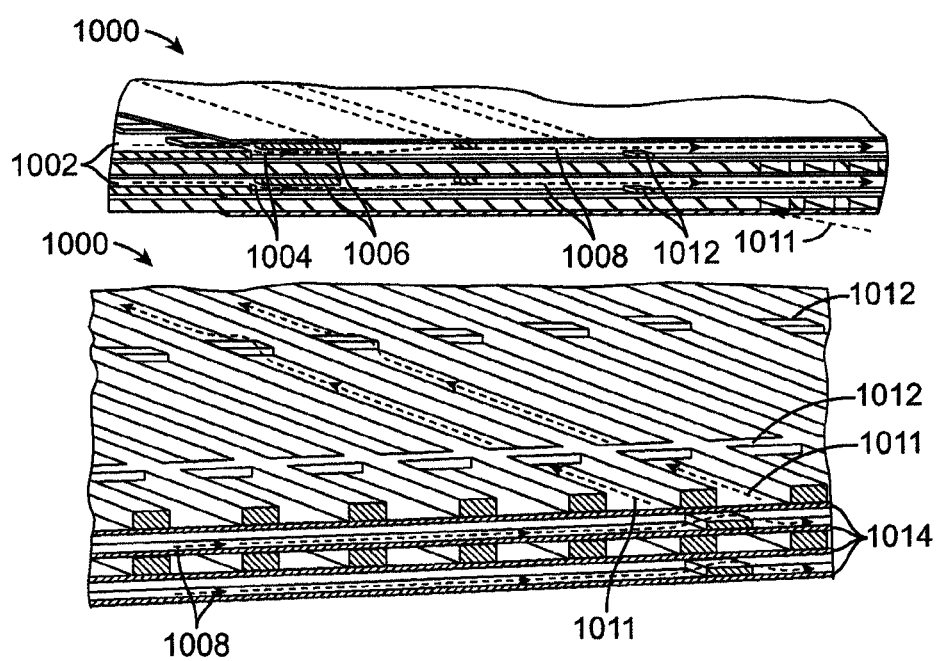
FIG. 50 is a detail view of the fluid flow path of a device having through-cut laminae.

FIG. 50 provides a detail of the fluid flow path 1000. Fluid enters the inlet header 1002, which directs the fluid to via 1004. The fluid travels through via 1004 to microchannel 1006, then to through-cut microchannel 1008. Through-cut microchannel 1008 is oriented orthogonal to through-cut microchannel 1010. Through-cut microchannels 1008 and 1010 have partial thickness dividers 1012 for structural support. Additionally, dividers 1012 provide mixing without substantially impeding fluid flow. Transfer layers 1014 separate and operably connect through-cut microchannels 1008 and 1010 to afford heat or mass transfer from one fluid to another.

Figure 51:
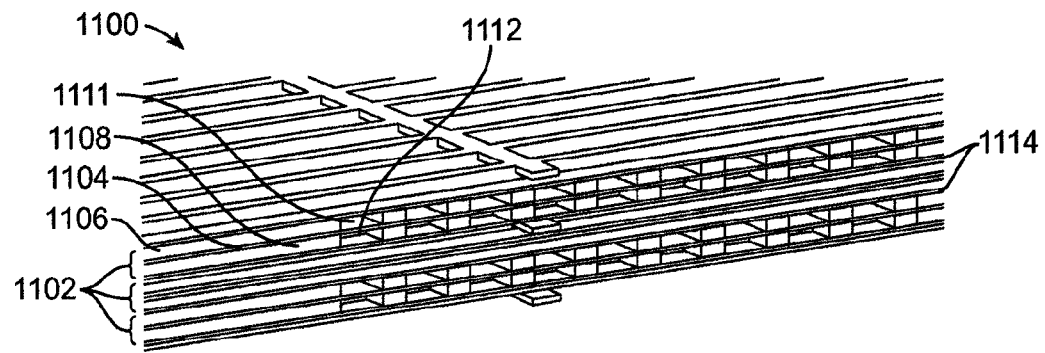
FIG. 51 is a perspective view of a device having alternating parallel and orthogonal through-cut microchannels.

FIG. 51 discloses a detail of a through cut device 1100 having both concurrent and cross current flow. Device 1100 comprises plural subunits 1102. Subunit 1102 comprises a transfer layer 1104 between a first lamina 1106 and a second lamina 1108. Laminae 1106 and 1108 have through-cut microchannels 1110 and 1112, respectively. Microchannels 1110 and 1112 are parallel to each other and orthogonal to microchannels of adjacent subunits 1102. The subunits 1102 are separated by transfer layers 1114. Consequently, subunits 1102 have concurrent or countercurrent flow between laminae 1106 and 1108 within subunit 1102, and crosscurrent flow between subunits.

Figure 52:
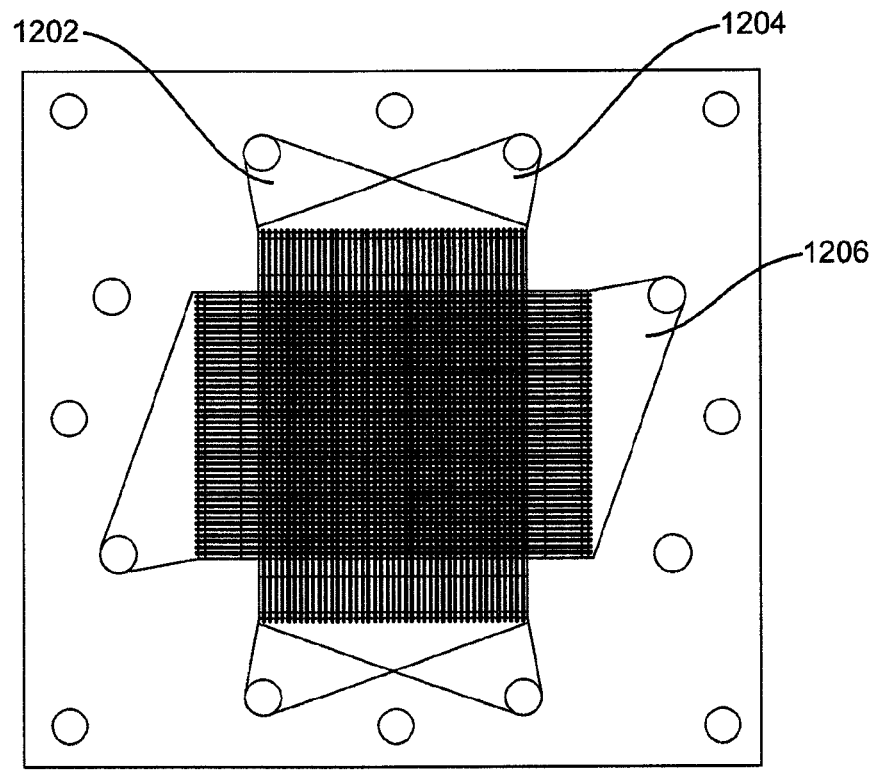
FIG. 52 is a plan view of the juxtaposition of the layers of a subunit incorporating a fluid membrane.
Figure 53:
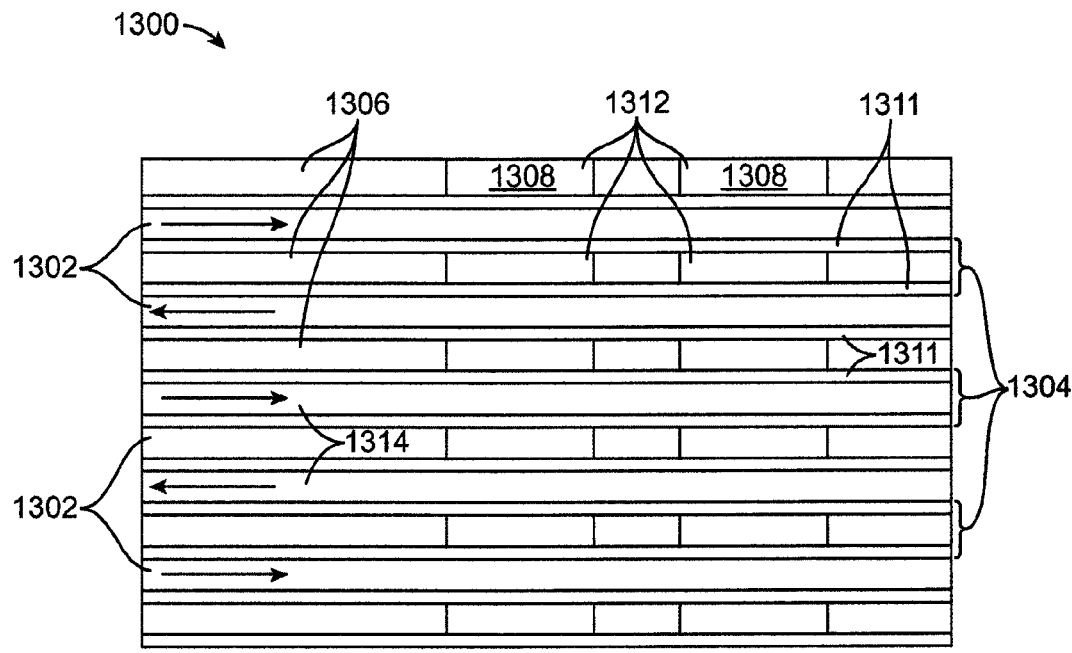
FIG. 53 is a schematic view of a device having fluid membranes.

The disclosed device may utilize fluid membranes. FIG. 52 discloses a plan view of the juxtaposition of the process fluid flow paths 1202 and 1204 and the fluid membrane channels 1206. Fluid flow paths 1202 and 1204 are substantially parallel to each other and substantially orthogonal to the fluid membrane channels 1206. Referring now to FIG. 53, fluid membrane device 1300 comprises through-cut laminae separated by fluid membranes 1304. Fluid membranes 1304 comprise through-cut lamina 1306 containing fluid and membrane supports 1311. Through-cut lamina 1308 has microchannels 1312 substantially orthogonal to microchannels 1314 of through-cut laminae 1302. A person of ordinary skill in the art will recognize that the membrane supports may be any material suitable for liquid membrane applications. For example and without limitation, a microporous polyethylene film may be used as a membrane support. A person of ordinary skill in the art will recognize that the need for, composition and positioning of membranes support will depend on, for example, the fluid used in the fluid membrane, the process fluids, and the operating temperatures and pressures.

Figure 54:
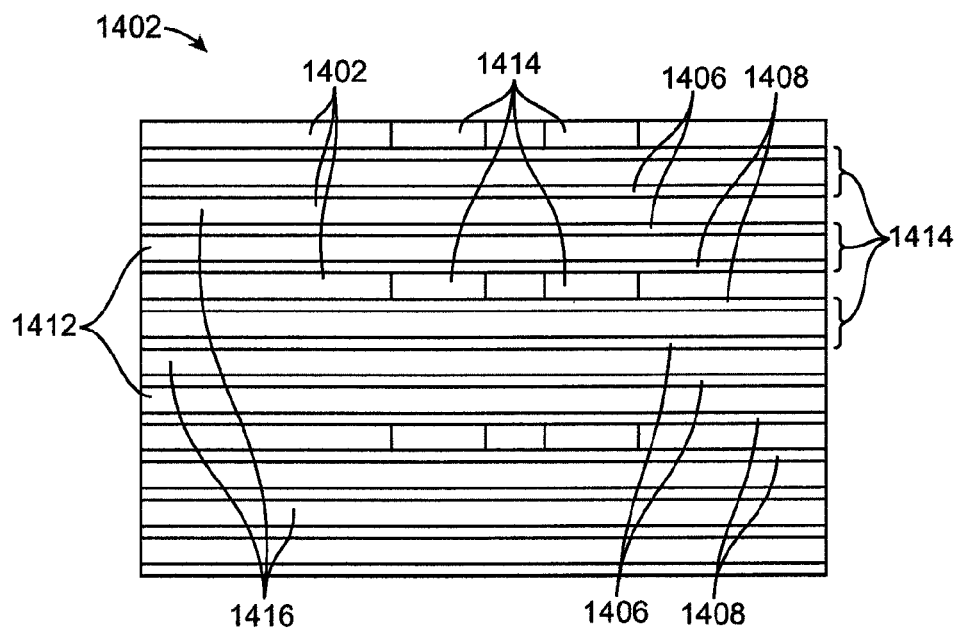
FIG. 54 is a schematic view of a device having fuel cells.

The mass transfer device may also be configured as a fuel cell. FIG. 54 discloses a fuel cell device 1400 comprising plural through-cut lamina 1402 separated by a transfer layer 1404 comprising a cathode 1406, an anode 1408, and a polymer electrolyte membrane 1412 therebetween. The device of FIG. 54 may contain, for instance, hydrogen in microchannels 1414, and oxygen in microchannels 1416. Transfer layers 1404 are oriented such that the anode 1408 is adjacent to the microchannels 1414 and the cathode is adjacent to the microchannels 1416. A person of ordinary skill in the art will recognize that this device may be used with any fuel cell and the transfer layer configuration will depend on, for instance, the fuels used and the operating temperature and pressure. A person of ordinary skill in the art will also recognize that the device may also be configured for concurrent or countercurrent flow.

FIG. 55 shows a plan view of an embodiment of a lamina of a flow field dialyzer without header regions. In this embodiment, the flow field has a polygonal shape with an inlet 1505 positioned at an upper point of the flow field and an outlet 1510 positioned at a lower point of the flow field. A plurality of support structures, such as pins, is located within the flow field. For clarity of illustration, the support structures are not shown in the flow field of FIG. 55. The configuration of the support structures within the flow field may vary as described above with reference to FIGS. 23-29.

The flow field is defined by opposed walls 1517 with a space therebetween for fluid flow. The walls 1517 diverge from the inlet 1505 such that the flow field has relatively small transverse size in the region of the inlet 1505 and a widened transverse size in a central region 1520. The central region 1520 is approximately represented with an oval shape in FIG. 55, although the shape of the central region may vary. From the central region 1520, the walls 1517 converge toward the outlet 1510 such that the flow field has a smaller transverse size at the outlet 1510 relative to the central region 1510. The inlet 1505 supplies fluid into the flow field without any particular flow region for the fluid to attain a relatively even distribution before entering the flow field.

The relatively constrained size at the inlet 1505 relative to the central region 1520 results in a pressure differential between fluid flowing at the inlet relative to fluid flowing at the central region 1520. That is, the pressure drops as the fluid flows into the widened central region. The pressure then rises as the fluid flows toward the smaller region of the outlet 1510. This results in an increase in fluid velocity as the fluid flows from the inlet 1505 toward the central region 1520, and then a decrease in velocity as the fluid flows from the central region 1520 toward the outlet 1510. The flow field may vary in shape and can have any of a variety of shapes that achieve the size differential between the regions of the inlet/outlet and the central region. For example, FIG. 56 shows a circular flow field that achieves size differentials between the regions of the inlet/outlet and the central region. Other shapes are possible, such as oval, diamond, etc.

In such an embodiment, no header may be required as a result of the flow field itself acting as its own header region and attaining a relatively even flow distribution simply through the effect of the pressure drop between the relatively higher pressure, higher fluid velocity region associated with the incoming fluid stream immediately adjacent the inlet 1505, and the relatively lower pressure, lower velocity region 1520 towards the center region 1520 of the flow field, combined with the various supports structures such as pins that the fluid impinges upon and flows around to create an even flow distribution. As more fluid enters the flow field through the inlet 1505, the fluid already in the flow field is pushed towards and out of the outlet 1510. Moreover, the reduction in fluid velocity as the fluid flows into the central region 1520 results in an increase in the residence time for fluid in the flow field. The increased residence time may result in an increased amount of diffusion across the dialyzer membrane and increased efficiency of the dialyzer.

In an embodiment, the pins 1512 are arranged in a series of rows such that the pins essentially form channels through the flow field. Using known techniques, channels of a certain depth between the rows of pins can be achieved as follows. First a master lamina may be created, for example, by machining a suitable material, such as aluminum, to the desired dimensions or by laser etching a sheet of suitable material, such as a polyimide sheet. In an embodiment, a sufficient amount of laminae are used to form a rectangular flow field having dimensions of about 10 centimeters by about 10 centimeters although variations are possible. An embossing master is then created from the master lamina either by embossing a polyetherimide sheet with the previously created master, or by a combination of laser etching and embossing with the previously created master. Finally, each lamina is created from the embossing master. It should be appreciated that variations are possible in the method of manufacture.

In creating the master using laser etching, the paths of the laser beams cut pathways of relatively even depth into the substrate. This is represented schematically in FIG. 57, where the lines 1610 represent successive pathways of laser beams that form the channels. A channel of relatively even depth into the lamina is formed along the length of each laser pathway. However, where the laser pathways cross one another, such as at junction 1615, the lamina is cut about twice as deep as where the laser pathways don't cross. The increased depth at the junctions 1615 is at least partially a result of the laser energy multiplying where the two lasers crossing one another. This results in an undulating path for each channel wherein each channel has a relatively uniform depth along a portion of its length and increased depth at the junctions 1615.

Figure 58:
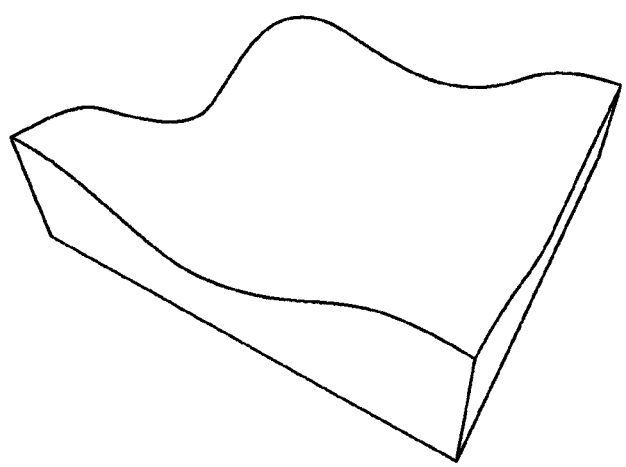
FIG. 58 is an enlarged view of a portion of a lamina where laser-formed channels intersect.
Figure 59:
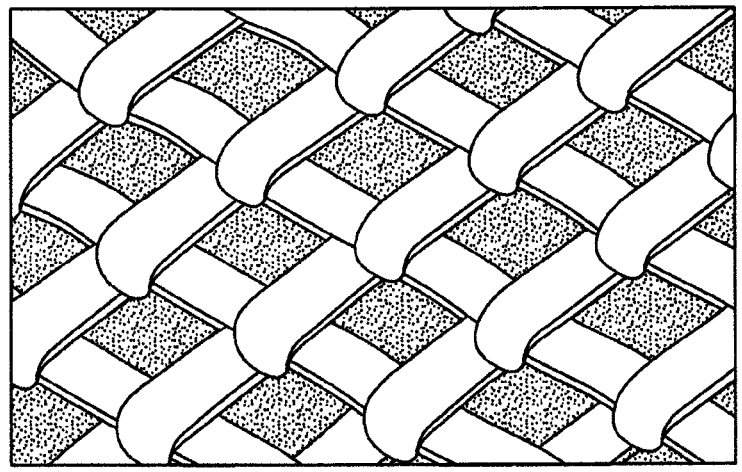
FIG. 59 is an enlarged view of a lamina surface showing undulating channels and pins formed between the channels.

FIG. 58 shows an enlarged view of a portion of lamina where the laser-formed channels intersect and have this type of undulating-floor channel resulting from a laser-etched cut. FIG. 59 shows an enlarged view of the lamina surface showing the undulating channels and pins formed between the channels. The embodiment shown in FIG. 59 has raised surfaces that are generally flat on the sides and top. In another embodiment, the raised surfaces are rounded on the sides and top. The undulating channel pathway floor results in more mixing conditions in the flow than would otherwise be achieved with a pathway floor between all pins of relatively equal depth, such as is typically creating when machining aluminum, for example. That is, the undulating channel pathway floor results in localized variations in flow velocity and flow direction in each region of increased depth. This causes localized mixing of the fluid as it flows along the regions of increased depth. The mixing tends to increase the efficiency of the device by repeatedly bringing fresh dialysate closer to the surface of the transfer membrane.

Figure 60:
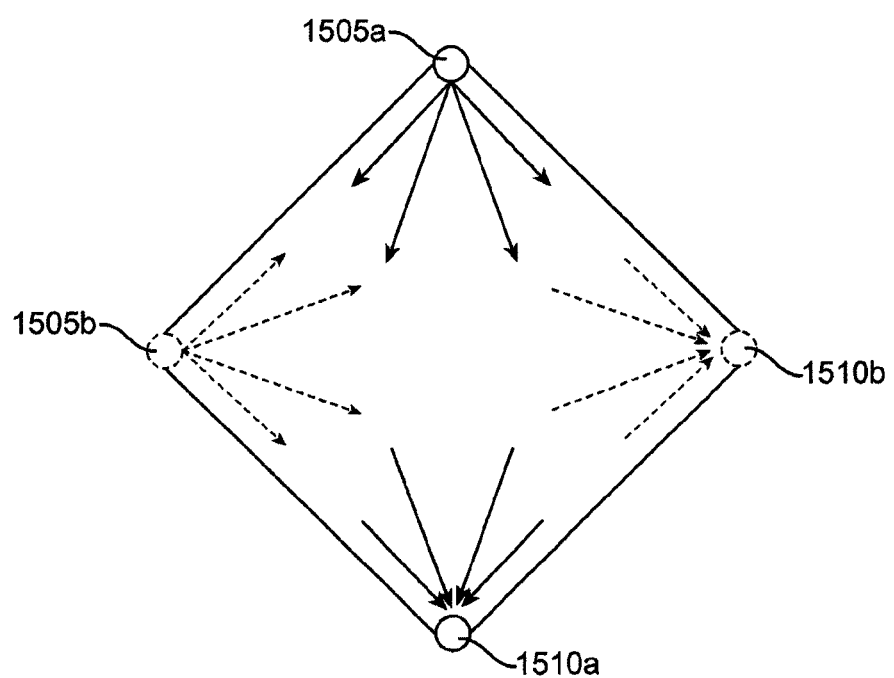
FIG. 60 is an embodiment where alternating headerless laminae are stacked in a cross-current manner.

FIG. 60 shows an embodiment where alternating symmetrical laminae are stacked in a cross-current manner for separation of the inlets 1505a and outlets 1510a of the laminae handling the fluid to be dialyzed, for example, from the inlets 1505b and outlets 1510b of the interleaved laminae handling the dialysate. For such an embodiment, each lamina may be substantially symmetrical about a central axis, such as square- or circle-shaped, so that even stacking may be achieved. Almost any degree of counter-current or cross-current or con-current flow with a headerless flow field and appropriately located inlets and outlets may be configured and would fall within the scope of the present invention.

To determine the feasibility of using the disclosed device for hemodialysis, one-, three-, and five-layer microchannel-based devices and a single-layer flow-field device were fabricated. The microchannel-based device contained microchannels that were 100 deep and 400 µm wide with 200 µm wide dividers. There are 51 channels in the array, giving a relatively small membrane transfer area of 4.2 cm² per layer (or transfer unit). The flow-field design had 6.3 cm² of membrane transfer area with a flow field depth of 60 µm. The laminae were prepared and patterned using a hot emboss technique. All devices were configured for cross flow and sealed using compression. The transfer layers were AN69 flat sheet membranes available from Gambro Medical.

Flow rates of fluids across the various microfluidic embodiments disclosed depend on the flow rate across an individual lamina and the number of lamina in a stack. In a microfluidic device that is being used for dialysis within a dialysis system, the flow rate across the microfluidic dialyzer may be substantially matched with the flow rate of dialysate being produced up-stream of the dialyzer. In this manner flow rates of up to 1000 ml/min may be achieved, though lower flow rates, such as 100 ml/min across either side of the membrane may be preferred for dialysis applications outside of the clinical setting, such as home or nocturnal dialysis.

B. Making Microfluidic Transfer Devices

Devices disclosed herein may be produced by a many of the techniques involved in a fabrication approach known as microlamination. Microlamination methods are described in several patents and pending applications commonly assigned to Oregon State University, including U.S. Pat. Nos. 6,793,831, 6,672,502, and U.S. Publication, Nos. 2007/0029365, entitled High Volume Microlamination Production of MECS Devices, and 2008/0108122, entitled Microchemical Nanofactories, all of which are incorporated herein by reference.

Microlamination consists of patterning and bonding thin layers of material, called laminae, to generate a monolithic device with embedded features. Microlamination typically involves at least three levels of production technology: 1) lamina patterning, 2) laminae registration, and 3) laminae bonding. Thus, the method of the present invention for making devices comprises providing plural laminae, registering the laminae, and bonding the laminae. Laminae bonding is not required for all disclosed embodiments, as the registered lamina are held between compression plates affording a compression seal. As yet another alternative, certain embodiments may have at least some laminae bonded together in combination with compression. The method also may include dissociating components (i.e., substructures from structures) to make the device. Component dissociation can be performed prior to, subsequent to, or simultaneously with bonding the laminae.

In one aspect of the invention, laminae are formed from a variety of materials, particularly metals; alloys, including intermetallic metals and super alloys; polymeric materials, including solely by way of example and without limitation, polycarbonate, polyethylene terephthalate (PET), polyether imide (PEI), poly(methyl methacrylate) (PMMA), and halogenated polyethylene such as poly(tetrafluoroethylene) (PTFE); ceramics; and combinations of such materials. The proper selection of a material for a particular application will be determined by various factors, such as the physical properties of the metal or metal alloy and cost. Examples of metals and alloys particularly useful for metal microlamination include stainless steels, copper, titanium, nickel, and aluminum. Laminae useful for the microlamination method of the present invention can have a variety of sizes. Generally, the laminae have thicknesses of from about 25 µM to about 1000 µm thick, preferably from about 25 µm to about 500 µm thick, and even more preferably from about 25 µm to 250 µm thick. Individual lamina within a stack also can have different thicknesses.

1. Lamina Patterns

Lamina patterning may comprise machining or etching a pattern in the lamina. Lamina patterning may also comprise embossing, roll embossing, and/or stamping. The pattern produced depends on the device being made. Without limitation, techniques for machining or etching include laser-beam, electron-beam, ion-beam, electrochemical, electrodischarge, chemical and mechanical material deposition or removal. The lamina can be patterned by combinations of techniques, such as both lithographic and non-lithographic processes. Lithographic processes include micromolding and electroplating methods, such as LIGA, and other net-shape fabrication techniques. Some additional examples of lithographic techniques include chemical micromachining (i.e., wet etching), photochemical machining, through-mask electrochemical micromachining (EMM), plasma etching, as well as deposition techniques, such as chemical vaporization deposition, sputtering, evaporation, and electroplating. Non-lithographic techniques include electrodischarge machining (EDM), mechanical micromachining and laser micromachining (i.e., laser photoablation). Photochemical and electrochemical micromachining likely are preferred for mass-producing devices.

One method for patterning lamina for disclosed device embodiments is microembossing. For instance, certain embodiments of the present disclosure were made using the following techniques. An Obducat Nano Imprint Lithography system was used to transfer microscale patterns from masters to polymeric parts. Master fabrication was accomplished by micromilling masters in metal, such as aluminum. A double transfer process using another material, such as polyether imide (PEI), as the intermediate was also used. A triple transfer process using patterned photoresist as the starting master was also used. The pattern was transferred from the photoresist, typically SU-8, to polydimethylsiloxane (PDMS), then to a thermoset epoxy (e.g., Conapoxy FR-1080) which then was used as the embossing master in the Obducat tool, transferring the pattern to a lower melting temperature polymer, such as polyethylene terephthalate (PET). The SU-8 can be deposited and patterned in multiple layers, allowing creation of precision multiplane masters. These planes can be both above and below the plane with the compression seal, allowing, for example, formation of protruding features such as sealing bosses as well as channels with multiple depths. Laminae also can be embossed on both sides simultaneously used two masters. Alignment techniques such as marks and pins were used during prototyping. It is anticipated that volume production will be accomplished using roll embossing and lamination techniques, also known as conversion processes, which will include automated alignment using vision systems.

Another method used for making disclosed embodiments was photochemical etching of metal laminae, e.g., 316/316L stainless steel. Patterned photoresist was used to mask both the front and back side of the laminae, with different masking patterns for each side. Partial etching from each side created intricate flow channels, including vias from one side to the other and channels open to both sides. Small support structures used to stabilize the channel dividers were also created. Such structures can be used to create segmented channel divider architectures, thereby increasing the active surface area of the transfer layer.

Laser machining was also used to cut vias, inlet and outlet ports, and alignment pin holes in laminae as well as embossing masters. An ESI 5330 with a 355 nm wavelength laser was used for laser machining. In volume production a laser may be also used to cut vias and other penetrations. To create the vias, the angle of the laser will preferably be non-orthogonal to create a non-orthogonal via, thereby reducing dead volumes in the flow channel. Alternatively, the vias and other penetrations may be created using a stamping operation. The stamping operation may be accomplished as part of the embossing operation through design of appropriate embossing/stamping masters. Non-orthogonal vias in particular are also created by designing appropriate embossing/stamping masters.

Laser micromachining has been accomplished with pulsed or continuous laser action. Machining systems based on Nd:YAG and excimer lasers are typically pulsed, while $CO_2$ laser systems are continuous. Electro Scientific Industries model 4420 is a typical system for Nd:YAG. This micromachining system uses two degrees of freedom by moving the focused laser flux across a part in a digitally controlled X-Y motion. The cutting action is either thermally or chemically ablative, depending on the material being machined and the wavelength used. The drive mechanism for the Nd:YAG laser may be a digitally controlled servo actuator that provides a resolution of approximately 2 µm. The width of the through cut, however, depends on the diameter of the focused beam.

Laminae also have been machined with $CO_2$ laser systems. Most of the commercial $CO_2$ lasers semi-ablate or liquefy the material being cut. A high-velocity gas jet often is used to help remove debris. As with the Nd:YAG systems, the laser (or workpiece) is translated in the X-Y directions to obtain a desired pattern in the material.

An Nd:YAG pulse laser has been used to cut through, for example, 90-µm-thick steel shims. The line widths for these cuts were approximately 35 µm wide, although with steel, some tapering was observed. Some debris and ridging may occur along the edge of the cut on the front side. This material may be removed easily from the surface during lamina preparation, such as by surface polishing.

Laminae also may be patterned using a $CO_2$ laser. The $CO_2$ through-cuts were approximately 200 µm wide and also exhibited a slight taper. The width of the $CO_2$ laser cut was the minimum achievable with the system used. The part may be cleaned in a lamina preparation step using surface polishing to remove debris.

Pulsed Nd:YAG lasers also are capable of micromachining laminae made from polymeric materials, such as laminae made from polyimides. Pulsed Nd:YAG lasers are capable of micromachining these materials with high resolution and no recast debris. Ultraviolet wavelengths appear best for this type of work where chemical ablation apparently is the mechanism involved in removing material. Clean, sharp-edged holes in the 25-50 μm diameter range have been produced.

2. Lamina Preparation

Depending on the lamina and patterning technique used, lamina patterning may include lamina preparation. The laminae can be prepared by a variety of techniques. For example, surface polishing of a lamina following pattern formation may be beneficial. Moreover, acid etching can be used to remove any oxides from a metal or alloy lamina. Lamina preparation may also include applying an oxide-free coating to some or all of the laminae. An example of this would be electroplating gold onto the lamina to prevent oxidation at ambient conditions.

3. Registration

Laminae registration comprises (1) stacking the laminae so that each of the plural laminae in a stack used to make a device is in its proper location within the stack, and (2) placing adjacent laminae with respect to each other so that they are properly aligned as determined by the design of the device. It should be recognized that a variety of methods can be used to properly align laminae, including manually and visually aligning laminae.

The precision to which laminae can be positioned with respect to one another may determine whether a final device will function. The complexity may range from structures such as microchannel arrays, which are tolerant to a certain degree of misalignment, to more sophisticated devices requiring highly precise alignment. A person of ordinary skill in the art will recognize that microchannels on adjacent laminae that are parallel to each other require a greater precision of alignment that embodiments having cross current flow. Several alignment methods can be used to achieve the desired precision. Registration can be accomplished, for example, using an alignment jig that accepts the stack of laminae and aligns each using some embedded feature, e.g., corners and edges, which work best if such features are common to all laminae. Another approach incorporates alignment features, such as holes, into each lamina at the same time other features are being machined. Alignment jigs are then used that incorporate pins that pass through the alignment holes. The edge alignment approach can register laminae to within 10 microns, assuming the laminae edges are accurate to this precision. With alignment pins and a highly accurate lamina machining technique, micron-level positioning is feasible.

Vision systems and thermally assisted lamina registration also can be used as desired. Additional detail concerning thermally assisted lamina registration is provided by Patent Publication No. 2007/0029365, which is incorporated herein by reference. A person of ordinary skill in the art also will recognize that the registration process can be automated.

4. Manufacture of Microfluidic Devices

Laminae bonding comprises bonding at least some of plural laminae one to another to produce a monolithic device (also referred to as a laminate). Laminae bonding can be accomplished by a number of methods including, without limitation, diffusion soldering/bonding, thermal brazing, adhesive bonding, thermal adhesive bonding, curative adhesive bonding, electrostatic bonding, resistance welding, microprojection welding, and combinations thereof. In addition to or as an alternative to bonding the registered lamina, the disclosed device may be assembled between compression plates. However, for some applications, bonding the lamina to the transfer layer may be preferable. Additionally, a bond or weld, such as a laser tack weld, may be used to facilitate assembly during manufacture.

A preferred method of device fabrication involves high through-put, low cost fabrication techniques. Laminae patterning is accomplished using several techniques, including embossing, stamping, and photochemical etching, among others. In one preferred embodiment, assembly is accomplished using roll techniques, such as those used in web processing or conversion industries. Polymer films are roll embossed and stamped, then laminated to form a subassembly. Metal laminae are patterned using photochemical etching. Abrasive waterjet techniques under development now may also be used for patterning metal laminae in the future. The subassemblies are separated, stacked, and assembled in compression frames. The primary sealing method is by compression from an external frame, however, bonding techniques such as laser welding and adhesives may be used for portions of some embodiments. A sealant or sealing method may be applied to the edges to prevent external seepage through the membrane.

C. Heat Transfer Operations

In other embodiments, the microfluidic transfer devices disclosed herein can be used in various heat transfer operations. As with the mass transfer devices disclosed herein, heat transfer devices can comprise a stack of plural subunits to scale the device to the desired volumetric capacity. Thermally conductive layers can be incorporated into such devices (e.g., positioned between the subunits) to allow heat to transfer from one fluid to another.

For example, referring to FIG. 21, in a heat transfer embodiment, transfer layer 109 can be a heat transfer layer for allowing heat to transfer from the fluid in microchannel 106 to the fluid in microchannel 112, or visa-versa. In this embodiment, transfer layer 110 can be any material capable of conducting heat from one fluid to another at a sufficient rate for the desired application. Relevant factors include, without limitation, the thermal conductivity of the heat transfer layer 09, the thickness of the heat transfer layer, and the desired rate of heat transfer. Suitable materials include, without limitation, metal, metal alloy, ceramic, polymer, or composites thereof. Suitable metals include, without limitation, iron, copper, aluminum, nickel, titanium, gold, silver, or tin. Copper may be a particularly desirable material.

Similar to the mass transfer devices described herein, the micron scale dimensions of a microfluidic heat transfer device reduces heat transfer limitations by reducing diffusion or conduction lengths through the bulk fluid, thereby increasing the heat transfer rate per unit area of transfer layer 109 (FIG. 21), consequently increasing efficiency and reducing device size.

Disclosed embodiments also may incorporate both heat and mass transfer components. A person of ordinary skill in the art will recognize that a number of configurations are possible and the desired application will dictate optimal configurations.

While this specification contains many specifics, these should not be construed as limitations on the scope of an invention that is claimed or of what may be claimed, but rather as descriptions of features specific to particular embodiments. Certain features that are described in this specification in the context of separate embodiments can also be implemented in combination in a single embodiment. Conversely, various features that are described in the context of a single embodiment can also be implemented in multiple embodiments separately or in any suitable sub-combination. Moreover, although features may be described above as acting in certain combinations and even initially claimed as such, one or more features from a claimed combination can in some cases be excised from the combination, and the claimed combination may be directed to a sub-combination or a variation of a sub-combination. Similarly, while operations are depicted in the drawings in a particular order, this should not be understood as requiring that such operations be performed in the particular order shown or in sequential order, or that all illustrated operations be performed, to achieve desirable results.

Although embodiments of various methods and devices are described herein in detail with reference to certain versions, it should be appreciated that other versions, embodiments, methods of use, and combinations thereof are also possible. Therefore the spirit and scope of the appended claims should not be limited to the description of the embodiments contained herein.

TABLE 1

| Temperature | Time | Pasteurization Type |
| --- | --- | --- |
| 63° C. (145° F.) | 30 minutes | Vat Pasteurization |
| 72° C. (161° F.) | 15 seconds | High Temperature Short Time Pasteurization (HTST) |
| 89° C. (191° F.) | 1.0 second | Higher-Heat Shorter Time Pasteurization (HHST) |
| 90° C. (194° F.) | 0.5 second | Higher-Heat Shorter Time Pasteurization (HHST) |
| 94° C. (201° F.) | 0.1 second | Higher-Heat Shorter Time Pasteurization (HHST) |
| 96° C. (204° F.) | 0.05 second | Higher-Heat Shorter Time Pasteurization (HHST) |
| 100° C. (212° F.) | 0.01 second | Higher-Heat Shorter Time Pasteurization (HHST) |
| 138° C. (280° F.) | 2.0 seconds | Ultra High Temperature Pasteurization (UHT) |

We claim:

1. A medical system, comprising:
    a filtration system capable of filtering a water stream;
    a water purification system capable of purifying said water stream in a non-batch process, comprising a microfluidic heat exchange system comprising a dwell chamber, wherein the water stream is maintained in the dwell chamber at a pasteurization temperature for a period of time effective to pasteurize the water stream;
    a mixing system capable of producing a stream of dialysate from mixing one or more dialysate components with the water stream in a non-batch process; and
    a dialyzer system, comprising
        a microfluidic or flow field dialyzer capable of being fluidly coupled to the stream of dialysate and a blood stream, the dialyzer having a membrane separating the stream of dialysate from the blood stream, the membrane facilitating dialysis of the blood stream;
        a plurality of pumps capable of pumping the stream of dialysate across the dialyzer; and
        a controller operatively coupled to the plurality of pumps, the controller capable of controlling a flow rate of the dialysate stream through one or more of the plurality of pumps so as to perform one or both of the processes of ultrafiltration and hemodiafiltration on the blood stream while the blood stream is undergoing dialysis.

2. The system of claim 1, wherein the purification system produces an ultra high temperature pasteurized water stream.

3. The system of claim 1, wherein the microfluidic heat exchange system further comprises:
    a fluid pathway having a water inlet and a water outlet, the fluid pathway further having:
        (a) a first region where water flows in a first direction at a first temperature;
        (b) a heater region downstream of the first region, the heater region including at least one heater that transfers heat into water flowing through the heater region to increase the temperature of water flowing in the heater region to a second temperature greater than the first temperature;
        (c) a second region downstream of the heater region where water flows in a second direction at a temperature greater than the first temperature, wherein water flowing in the second region thermally communicates with water flowing in the first region such that heat transfers from water flowing in the second region to water flowing in the first region resulting in a temperature reduction in the water as it flows through the second region, wherein water flows out of the pathway through the outlet at a temperature less than the second temperature.

4. The system of claim 3, wherein at least a portion of the fluid pathway is at least one microchannel.

5. The system of claim 3, wherein the dwell chamber is downstream of the heater region and upstream of the second region, and wherein the water remains within the dwell chamber at or above the second temperature for at least a predetermined amount of time relative to the fluid flow rate through the dwell chamber, prior to flowing into the second region.

6. The system of claim 3, wherein the second temperature is at least 138 degrees Celsius.

7. The system of claim 3, further comprising a pump upstream of the inlet and a throttling valve downstream of the outlet, wherein the pump and throttling valve are arranged in a closed loop control arrangement for maintaining water in the fluid pathway above a saturation pressure such that the water does not change state at any point while present in the system.

8. The system of claim 3, wherein the first region, heater region, dwell chamber and second region are contained within a single laminar body.

9. The system of claim 1, wherein the dialyzer comprises a first flow field comprising a first set of support structures around which the blood stream flows during operation, a second flow field comprising a second set of support structures around which the dialysate stream flows during operation, and wherein the membrane comprises a mass transfer layer interleaved between the first and second flow fields, across which layer dialysis of the blood occurs when in operation.

10. The system of claim 1, wherein the plurality of pumps include:
    a first pump fluidly coupled to the stream of dialysate and configured to pump the stream of dialysate through a fluid inlet pathway toward the dialyzer;
    a second pump coupled to a fluid outlet pathway from the dialyzer and configured to pump the fluid through the fluid outlet pathway away from the dialyzer; and
    a third pump coupled to the fluid outlet pathway.

11. The system of claim 10, wherein the controller operates the first, second and third pumps to maintain balance between the fluid flow rates in the inlet pathway and outlet pathway such that substantially no fluid is added to or removed from the blood during operation.

12. The system of claim 10, wherein the controller operates the first, second and third pumps to maintain balance between the fluid flow rates in the inlet pathway and outlet pathway such that a desired amount of fluid is removed from the blood during operation.

13. The system of claim 10, wherein the controller operates the first, second and third pumps to maintain balance between the fluid flow rates in the inlet pathway and outlet pathway such that a desired amount of fluid is added to the blood during a time span of operation.

14. The system of claim 10, wherein the controller operates the first, second and third pumps to achieve a desired level of hemodiafiltration by cycling the third pump between a lower speed and a higher speed substantially without a net addition of fluid to the blood.

15. The system of claim 10, wherein the controller operates the first, second and third pumps to achieve a desired level of hemodiafiltration and a desired rate of fluid addition to the blood by cycling the third pump between a lower speed and a higher speed.

16. The system of claim 10, wherein the controller operates the first, second and third pumps to achieve a desired level of hemodiafiltration and a desired rate of fluid removal from the blood by cycling the third pump between a lower speed and a higher speed.

17. A medical system, comprising:
 a filtration system capable of filtering a water stream;
 a water purification system, capable of purifying the water stream in a non-batch process comprising a microfluidic heat exchange system having a fluid pathway comprising
  (a) a first region comprising a water inlet where water flows in a first direction at a first temperature;
  (b) a heater region downstream of the first region, comprising at least one heater to heat water flowing through the heater region to a second temperature greater than the first temperature and at least 138° C.;
  (c) a dwell chamber downstream of the heater region wherein the water remains within the dwell chamber at or above the second temperature for a predetermined amount of time effective to produce a concentration of less than $10^{-6}$ colony forming units per milliliter;
  (d) a second region downstream of the dwell chamber where water flows in a second direction at a temperature greater than the first temperature, wherein water flowing in the second region thermally communicates with water flowing in the first region such that heat transfers from water flowing in the second region to water flowing in the first region resulting in a temperature reduction in the water as it flows through the second region, so that water flowing out of the pathway through a water outlet is at a temperature less than the second temperature;
 a mixing system capable of producing a stream of dialysate from mixing one or more dialysate components with purified water from the water stream in a non-batch process; and
 a dialyzer system, comprising
  a microfluidic or flow field dialyzer fluidly coupled to the stream of dialysate and a blood stream, the dialyzer comprising a membrane separating the stream of dialysate from the blood stream, the membrane facilitating dialysis of the blood stream;
  at least one pump capable of pumping the stream of dialysate across the dialyzer; and
  a controller operatively coupled to at least one pump, the controller capable of controlling a flow rate of the dialysate stream through at least one pump to perform water ultrafiltration, hemodiafiltration on the blood stream while the blood stream is undergoing dialysis, or both.

* * * * *